United States Patent
Herold et al.

(10) Patent No.: US 8,071,651 B2
(45) Date of Patent: *Dec. 6, 2011

(54) 5-AMINO-4-HYDROXY-7-(IMIDAZO [1,2-A] PYRIDIN-6-YLMETHYL)-8-METHYL-NONAMIDE DERIVATIVES AND RELATED COMPOUNDS AS RENIN INHIBITORS FOR THE TREATMENT OF HYPERTENSION

(75) Inventors: Peter Herold, Allschwil (CH); Robert Mah, Allschwil (CH); Vincenzo Tschinke, Allschwil (CH); Stefan Stutz, Allschwil (CH); Aleksandar Stojanovic, Allschwil (CH); Christiane Marti, Allschwil (CH); Dirk Behnke, Allschwil (CH); Stjepan Jelakovic, Allschwil (CH)

(73) Assignee: Novartis AG, Basel (CH)

( * ) Notice: Subject to any disclaimer, the term of this patent is extended or adjusted under 35 U.S.C. 154(b) by 670 days.

This patent is subject to a terminal disclaimer.

(21) Appl. No.: 11/992,132

(22) PCT Filed: Sep. 14, 2006

(86) PCT No.: PCT/EP2006/066369
§ 371 (c)(1),
(2), (4) Date: Mar. 17, 2008

(87) PCT Pub. No.: WO2007/031558
PCT Pub. Date: Mar. 22, 2007

(65) Prior Publication Data
US 2010/0063087 A1    Mar. 11, 2010

(30) Foreign Application Priority Data
Sep. 17, 2005 (CH) ....................... 1526/05

(51) Int. Cl.
*A01N 43/42* (2006.01)
*A01N 43/40* (2006.01)
*A01N 43/58* (2006.01)
*A01N 43/00* (2006.01)
*A01N 43/64* (2006.01)
*A01N 37/18* (2006.01)
*A01N 35/00* (2006.01)
*A01N 33/18* (2006.01)
*A01N 33/24* (2006.01)
*C07C 233/00* (2006.01)
*C07C 235/00* (2006.01)
*C07C 237/00* (2006.01)
*C07C 239/00* (2006.01)
*A61K 31/16* (2006.01)
*A61K 31/12* (2006.01)

(52) U.S. Cl. ........ 514/630; 514/336; 514/613; 514/242; 514/247; 514/183; 514/381; 514/676; 514/300; 548/250; 548/255; 548/300.1; 564/123

(58) Field of Classification Search ............... 514/300, 514/336, 613, 242, 247, 183, 381, 630, 676; 548/250, 255, 300.1; 564/123
See application file for complete search history.

(56) References Cited

U.S. PATENT DOCUMENTS
5,559,111 A    9/1996  Göschke et al.
2008/0280895 A1* 11/2008 Herold et al. .......... 514/230.5

FOREIGN PATENT DOCUMENTS
EP    0 678 503    10/1995
WO    2005/090305    9/2005

OTHER PUBLICATIONS
International Search Report issued Feb. 22, 2007 in the International (PCT) Application PCT/EP2006/066369 of which the present application is the U.S. National Stage. Written Opinion in the International (PCT) Application PCT/EP2006/066369 of which the present application is the U.S. National Stage.

* cited by examiner

*Primary Examiner* — Sreeni Padmanabhan
*Assistant Examiner* — Kendra D Carter
(74) *Attorney, Agent, or Firm* — Wenderoth, Lind & Ponack, L.L.P.

(57) ABSTRACT

Compounds of the general formula (I) or its salt or a compound in which one or more atoms are replaced by their stable, nonradio-active isotopes, in particular its pharmaceutically acceptable salt; in which X is —$CH_2$—; R is a mono- to tetra-substituted, mono- or bicyclic, unsaturated heterocyclic radical having 1 to 4 nitrogen atoms, $R^2$ is $C_{1-6}$alkyl or $C_{3-6}$cycloalkyl; $R^3$ is independently of one another H, $C_{1-6}$alkyl, $C_{1-6}$alkoxycarbonyl or $C_{1-6}$alkanoyl; $R^4$ is $C_{2-6}$alkenyl, $C_{1-6}$alkyl, unsubstituted or substituted aryl-$C_{1-6}$alkyl or $C_{3-8}$cycloalkyl; $R^5$ is -$L_m$-$R^6$; L is $C_{1-6}$alkylene which is optionally substituted by 1-4 halogen, or a linker: formula (II) n=0, 1 or 2; m=0 or 1; $R^6$ is a radical composed of 2 cyclic systems selected from bicyclo[x.y.z]alkyl, spiro[o.p]alkyl, mono- or bioxabicyclo[x.y.z]alkyl or mono- or bioxaspiro [o.p]alkyl, all of which may be substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino, or if m=0: is also saturated $C_{3-8}$heterocyclyl which comprises 1-2 oxygen atoms, substituted by 1-3 substituents selected from $C_{1-6}$alkyl, $C_{1-6}$alkoxy, cyano, halogen, $C_{1-6}$alkoxy-$C_{1-6}$ alkyl, hydroxy-$C_{1-6}$alkyl or dialkylamino, or if m=1: is also saturated $C_{3-8}$heterocyclyl which comprises 1-2 oxygen atoms, optionally substituted by 1-3 substituents selected from $C_{1-6}$alkyl, $C_{1-6}$alkoxy, cyano, halogen, $C_{1-6}$-alkoxy-$C_{1-6}$ alkyl, hydroxy-$C_{1-6}$alkyl or dialkylamino; have renin-inhibiting properties and can be used as medicines for the treatment of hypertension.

(I)

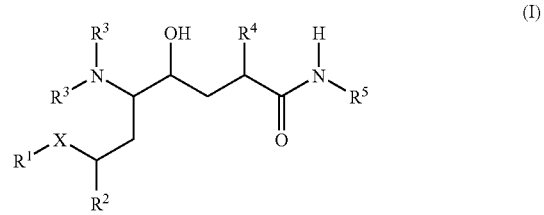

11 Claims, No Drawings

5-AMINO-4-HYDROXY-7-(IMIDAZO [1,2-A] PYRIDIN-6-YLMETHYL)-8-METHYL-NONAMIDE DERIVATIVES AND RELATED COMPOUNDS AS RENIN INHIBITORS FOR THE TREATMENT OF HYPERTENSION

The present invention relates to novel alkanamides, processes for their preparation and the use of the compounds as medicines, in particular as renin inhibitors.

Alkanamides for use as medicines are disclosed for example in EP 678503. In relation especially to the renin inhibition, however, there is still a need for active ingredients of high potency. The priority in this is to improve the pharmacokinetic properties. These properties, which aim at better bioavailability, are for example absorption, metabolic stability, solubility or lipophilicity.

The invention therefore provides compounds of the general formula

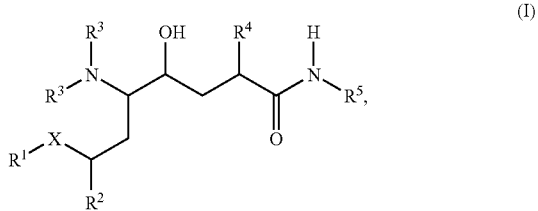

(I)

in which

X is —$CH_2$—;

$R^1$ is a mono- to tetrasubstituted, mono- or bicyclic, unsaturated heterocyclic radical having 1 to 4 nitrogen atoms, where the substituents of the said radicals are selected independently of one another from the group consisting of acetamidinyl-$C_{1-6}$alkyl, 3-acetamidomethylpyrrolidinyl, acyl-$C_{1-6}$alkoxy-$C_{1-6}$alkyl, (N-acyl)-$C_{1-6}$alkoxy-$C_{1-6}$alkyl-amino, $C_{1-6}$-alkanoyl, $C_{1-6}$alkanoyloxy, $C_{2-6}$alkenyl, $C_{2-6}$alkenyloxy, $C_{2-6}$alkenyloxy-$C_{1-6}$alkyl, $C_{1-6}$alkoxy, $C_{1-4}$alkoxy-$C_{1-6}$alkoxy, $C_{1-6}$alkoxy-$C_{1-6}$alkoxy-$C_{1-6}$alkyl, $C_{1-6}$alkoxy-$C_{1-6}$-alkyl, (N—$C_{1-6}$alkoxy)-$C_{1-6}$alkylaminocarbonyl-$C_{1-6}$alkoxy, (N—$C_{1-6}$alkoxy)-$C_{1-6}$alkyl-aminocarbonyl-$C_{1-6}$alkyl, $C_{1-6}$alkoxy-$C_{1-6}$-alkylcarbamoyl, $C_{1-6}$alkoxy-$C_{1-6}$alkylcarbonyl, $C_{1-6}$alkoxy-$C_{1-6}$alkylcarbonylamino, 2-$C_{1-6}$alkoxy-$C_{1-6}$alkyl-4-oxoimidazol-1-yl, 3-$C_{1-6}$alkoxy-$C_{1-6}$alkylpyrrolidinyl, 1-$C_{1-6}$alkoxy-$C_{1-6}$alkyl-tetrazol-5-yl, 5-$C_{1-6}$alkoxy-$C_{1-6}$alkyltetrazol-1-yl, $C_{1-6}$alkoxyaminocarbonyl-$C_{1-6}$alkoxy, $C_{1-6}$alkoxyaminocarbonyl-$C_{1-6}$alkyl, $C_{1-6}$-alkoxycarbonyl, $C_{1-6}$alkoxycarbonyl-$C_{1-6}$alkoxy, $C_{1-6}$alkoxycarbonyl-$C_{1-6}$alkyl, $C_{1-6}$alkoxycarbonylamino, $C_{1-6}$alkoxycarbonylamino-$C_{1-6}$alkoxy, $C_{1-6}$alkoxycarbonylamino-$C_{1-6}$alkyl, $C_{1-6}$alkyl, (N—$C_{1-6}$alkyl)-$C_{1-4}$alkoxy-$C_{1-6}$alkylcarbamoyl, (N—$C_{1-6}$alkyl)-$C_{1-6}$alkoxy-$C_{1-6}$alkylcarbonylamino, (N—$C_{1-6}$alkyl)-$C_{1-6}$alkoxycarbonylamino, (N—$C_{1-6}$alkyl)-$C_{0-6}$alkylcarbonylamino-$C_{1-6}$alkoxy, (N—$C_{1-6}$alky)-$C_{0-6}$alkylcarbonylamino-$C_{1-6}$alkyl, (N—$C_{1-6}$alkyl)-$C_{1-6}$alkylsulphonylamino-$C_{1-6}$alkoxy, (N—$C_{1-6}$alkyl)-$C_{1-6}$alkylsulphonylamino-$C_{1-6}$alkyl, $C_{1-6}$alkylamidinyl, $C_{1-6}$alkylamino, di-$C_{1-6}$alkylamino, $C_{1-6}$alkylamino-$C_{2-6}$alkoxy, di-$C_{1-6}$alkylamino-$C_{2-6}$alkoxy, $C_{1-6}$alkylamino-$C_{1-6}$alkyl, $C_{1-6}$alkylaminocarbonyl, $C_{1-6}$alkylaminocarbonyl-$C_{1-6}$alkoxy, di-$C_{1-6}$ alkylaminocarbonyl-$C_{1-6}$alkoxy, $C_{1-6}$alkylaminocarbonyl-$C_{1-6}$alkoxy-$C_{1-6}$alkyl, $C_{1-6}$alkylaminocarbonyl-$C_{1-6}$alkyl, $C_{1-6}$alkylaminocarbonylamino-$C_{1-6}$alkoxy, $C_{1-6}$alkylaminocarbonylamino-$C_{1-6}$alkyl, di-$C_{1-6}$alkylaminocarbonyl-$C_{1-6}$alkyl, di-$C_{1-6}$alkylamino-$C_{1-6}$alkyl, $C_{1-6}$alkylcarbamoyl, di-$C_{1-6}$alkylcarbamoyl, $C_{0-6}$alkylcarbonyl-amino, $C_{0-6}$alkylcarbonylamino-$C_{1-6}$alkoxy, $C_{0-6}$alkylcarbonylamino-$C_{1-6}$alkyl, $C_{1-6}$alkylcarbonyloxy-$C_{1-6}$alkoxy, $C_{1-6}$alkylcarbonyloxy-$C_{1-6}$alkyl, $C_{1-6}$alkylenedioxy, $C_{1-6}$alkylsulphonyl, $C_{1-6}$alkylsulphonyl-$C_{1-6}$alkoxy, $C_{1-6}$alkylsulphonyl-$C_{1-6}$alkyl, $C_{1-6}$alkylsulphonylamino-$C_{1-6}$alkoxy, $C_{1-6}$alkylsulphonylamino-$C_{1-6}$alkyl, amino, amino-$C_{2-7}$alkoxy, amino-$C_{1-6}$alkyl, aryl-$C_{1-6}$alkanoyl, benzoyloxy-$C_{2-6}$alkoxy, carbamoyl, carbamoyl-$C_{1-6}$alkoxy, carbamoyl-$C_{1-6}$ alkyl, carboxy, carboxy-$C_{1-6}$alkoxy, carboxy-$C_{1-6}$ alkoxy-$C_{1-6}$alkyl, carboxy-$C_{1-6}$alkyl, cyano, cyano-$C_{1-6}$a lkoxy, cyano-$C_{1-6}$alkyl, $C_{3-8}$cycloalkyl-$C_{1-6}$alkanoyl, $C_{3-4}$cycloalkyl-$C_{0-6}$alkoxy, $C_{3-8}$cycloalkyl-$C_{0-6}$alkyl, $C_{3-8}$cycloalkyl-carbonylamino, $C_{3-8}$cycloalkylcarbonylamino-$C_{1-6}$alkoxy, $C_{3-8}$cyclo-alkylcarbonylamino-$C_{1-6}$ alkyl, 3,4-dihydroxypyrrolidinyl, O,N-dimethylhydroxylamino-$C_{1-6}$alkyl, 2,6-dimethylmorpholinyl, 3,5-dimethylmorpholinyl, dioxanyl, dioxolanyl, dioxolanyl-$C_{1-6}$alkoxy, 4,4-dioxothiomorpholinyl, dithianyl, dithiolanyl, optionally $C_{1-6}$alkoxy-, $C_{1-6}$alkyl-, dihydroxy-$C_{1-6}$alkylaminocarbonyl- or halogen-substituted furyl, furyl-$C_{1-6}$ alkoxy, furyl-$C_{1-6}$ alkyl, pyridyl-$C_{1-6}$alkoxy, pyridyl-$C_{1-6}$alkyl, pyridyl-amino, pyridyloxy, pyridylthio, pyrimidinyl, pyrimidinyl-$C_{1-6}$alkoxy, pyrimidinylamino, pyrimidinyloxy, pyrimidinylthio, thienyl, thienyl-$C_{1-6}$alkoxy or thienyl-$C_{1-6}$alkyl, halogen, heterocyclyl-$C_{1-6}$alkanoyl, hydroxy, hydroxy-$C_{2-6}$alkoxy, hydroxy-$C_{2-6}$alkoxy-$C_{1-6}$alkoxy, hydroxy-$C_{2-6}$alkoxy-$C_{1-6}$alkyl, hydroxy-$C_{1-6}$alkyl, (N-hydroxy)-$C_{1-6}$alkylaminocarbonyl-$C_{1-6}$alkoxy, (N-hydroxy)-$C_{1-6}$alkylaminocarbonyl-$C_{1-6}$alkyl, (N-hydroxy)aminocarbonyl-$C_{1-6}$alkoxy, (N-hydroxy)aminocarbonyl-$C_{1-6}$alkyl, hydroxy-benzyloxy, 2-hydroxymethylpyrrolidinyl, 4-hydroxypiperidinyl, 3-hydroxypyrrolidinyl, imidazolyl-$C_{1-6}$alkoxy, imidazolyl-$C_{1-6}$alkyl, methoxybenzyloxy, methylenedioxy-benzyloxy, 2-methylimidazolyl-$C_{1-6}$alkoxy, 2-methylimidazolyl-$C_{1-6}$alkyl, 3-methyl-[1,2,4]-oxadiazol-5-yl-$C_{1-6}$alkoxy, 5-methyl-[1,2,4]-oxadiazol-3-yl-$C_{1-6}$ alkoxy, 3-methyl-[1,2,4]-oxadiazol-5-yl-$C_{1-6}$ alkyl, 5-methyl-[1,2,4]-oxadiazol-3-yl-$C_{1-6}$alkyl, O-methyl-oximyl-$C_{1-6}$alkyl, 4-methylpiperazinyl, N-methylpiperazino-$C_{1-6}$alkoxy, N-methyl-piperazino-$C_{1-6}$alkoxy-$C_{1-6}$alkyl, N-methylpiperazino-$C_{1-6}$alkyl, 5-methyltetrazol-1-yl-$C_{1-6}$alkoxy, 5-methyltetrazol-1-yl-$C_{1-6}$alkyl, morpholinyl, morpholino-$C_{1-6}$alkoxy, morpholino-$C_{1-6}$alkoxy-$C_{1-6}$alkyl, morpholino-$C_{1-6}$ alkyl, nitro, [1,2,4]-oxadiazol-5-yl-$C_{1-6}$alkoxy, [1,2,4]-oxadiazol-5-yl-$C_{1-6}$alkyl, oxazol-4-yl-$C_{1-6}$alkoxy, oxazol-4-yl-$C_{1-6}$alkyl, oxide, oxo, 2-oxoimidazolidinyl, 2-oxo-[1,3]oxazinyl, 2-oxooxazolidinyl, 2-oxooxazolidinyl-$C_{1-6}$alkoxy, 2-oxooxazolidinyl-$C_{1-6}$alkyl, 4-oxopiperidinyl, 2-oxopyrrolidinyl, 2-oxopyrrolidinyl-$C_{1-6}$ alkoxy, 2-oxopyrrolidinyl-$C_{1-6}$alkyl, 2-oxotetrahydro-pyrimidinyl, 4-oxothiomorpholinyl, optionally $C_{1-6}$alkoxy-, $C_{1-6}$alkoxycarbonyl-, $C_{1-6}$alkyl-, $C_{1-6}$alkylamino-, di-$C_{1-6}$alkylamino-, halogen-, hydroxy-, hydroxy-$C_{1-6}$alkyl-, or trifluoromethyl-substituted phenoxy, phenyl, phenyl-$C_{1-6}$alkoxy, phenyl-$C_{1-6}$alkyl or phenylthio, piperazinyl, piperazino-$C_{1-6}$ alkoxy, piperazino-$C_{1-6}$ alkoxy-$C_{1-6}$alkyl, piperazino-$C_{1-6}$alkyl, piperidinyl, piperidino-$C_{1-6}$alkoxy, piperidino-$C_{1-6}$alkoxy-$C_{1-6}$alkyl, polyhalogen-$C_{1-6}$alkoxy, polyhalogen-$C_{1-6}$ alkyl, pyridylcarbamoyloxy-$C_{1-6}$alkoxy, pyridylcarbonylamino-$C_{1-6}$alkyl, pyrrolidinyl, pyrrolyl, tetrazol-1-yl-$C_{1-6}$alkoxy, tetrazol-2-yl-$C_{1-6}$alkoxy, tetrazol-5-yl-$C_{1-6}$alkoxy, tetrazol-1-yl-$C_{1-6}$alkyl, tetrazol-2-yl-$C_{1-6}$ alkyl, tetrazol-5-yl-$C_{1-6}$alkyl, thiazol-4-yl-$C_{1-6}$ alkoxy, thiomorpholinyl, [1,2,4]-triazol-1-yl-$C_{1-6}$ alkoxy, [1,2,4]-triazol-1-yl-$C_{1-6}$alkyl, [1,2,4]-triazol-4-yl-$C_{1-6}$alkyl and the radical —O—CH$_2$CH(OH)CH$_2$NRx, where NRx is a mono- or di-$C_{1-6}$alkylamino, N-methylpiperazino, morpholino, piperazino or piperidino radical, and where in the case where $R^1$ is a bicyclic heterocyclic ring system, at least the ring not directly bonded to X is substituted as indicated;

$R^2$ is $C_{1-6}$alkyl or $C_{3-6}$cycloalkyl;

$R^3$ is independently of one another H, $C_{1-6}$alkyl, $C_{1-6}$alkoxycarbonyl or $C_{1-6}$alkanoyl;

$R^4$ is $C_{2-6}$alkenyl, $C_{1-6}$alkyl, unsubstituted or substituted aryl-$C_{1-6}$alkyl or $C_{3-8}$cycloalkyl;

$R^5$ is -$L_m$-$R^6$;

L is $C_{1-8}$alkylene which is optionally substituted by 1-4 halogen, or a linker:

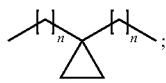

n=0, 1 or 2;
m=0 or 1;

$R^6$ is a radical composed of 2 cyclic systems selected from bicyclo[x.y.z]alkyl, spiro[o.p]alkyl, mono- or bioxabicyclo[x.y.z]alkyl or mono- or bioxaspiro[o.p]alkyl, all of which may be substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino, or
  if m=0: is also saturated $C_{3-8}$heterocyclylwhich comprises 1-2 oxygen atoms, substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino, or
  if m=1: is also saturated $C_{3-8}$heterocyclyl which comprises 1-2 oxygen atoms, optionally substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$ alkyl or dialkylamino;

o=2, 3, 4, 5 or 6
p=2, 3, 4, 5 or 6
x=1, 2, 3, 4 or 5;
y=1, 2, 3, 4 or 5;
z=0, 1, 2, 3, 4 or 5; where x≧y≧z;

and salts, especially pharmaceutically useable salts thereof.

$R^2$ and $R^4$ as alkyl may be linear or branched and preferably comprise 1 to 4 C atoms. Examples are methyl, ethyl, n- and i-propyl, n-, i- and t-butyl, pentyl and hexyl. In a preferred embodiment, $R^2$ and $R^4$ in compounds of the formula (I) are each isopropyl.

L as alkylene may be linear or branched and preferably comprise 1 to 4 C atoms. Examples of alkylene are methylene, ethylene, n- and i-propylene, n-, i- and t-butylene, pentylene and hexylene. Methylene, 1,2-ethylene, n- and i-propylene, n-, i- and t-butylene are preferred.

Mono- or bicyclic, unsaturated heterocyclic radicals having 1 to 4 nitrogen atoms may be substituted one or more times, in particular once, twice or three times. The heterocyclyl radicals are preferably bonded via a C atom to the remainder of the molecule. Examples of such mono- or bicyclic, unsaturated heterocyclic radicals having 1 to 4 nitrogen atoms are benzoimidazolyl, quinazolinyl, quinolyl, quinoxalinyl, imidazolyl, imidazo[1,5-a]pyridinyl, imidazo[1,2-a]pyrimidinyl, indazolyl, indolyl, isoquinolyl, 1-oxidopyridyl, phthalazinyl, pyrazinyl, pyrazolyl, pyridyl, pyrimidinyl, pyrrolo[2,3-b]pyridinyl, pyrrolo[3,2-c]pyridinyl, pyrrolo[2,3-c]pyridinyl, pyrrolo[3,2-b]pyridinyl, 1H-pyrrolo[2,3-b]pyridyl, pyrrolyl, triazinyl, triazolyl, [1,2,3]-triazolo[1,5-a]pyridinyl or [1,2,4]-triazolo[4,3-a]pyridinyl. Examples of substituents on such heterocyclyl radicals are acetamidinyl-$C_{1-6}$alkyl, 3-acetamidomethylpyrrolidinyl, acyl-$C_{1-6}$alkoxy-$C_{1-6}$alkyl, (N-acyl)-$C_{1-6}$alkoxy-$C_{1-6}$alkylamino, $C_{1-6}$alkanoyl, $C_{1-6}$alkanoyloxy, $C_{2-6}$alkenyl, $C_{2-6}$alkenyloxy, $C_{2-6}$alkenyloxy-$C_{1-6}$alkyl, $C_{1-6}$alkoxy, $C_{1-6}$alkoxy-$C_{1-6}$ alkoxy, $C_{1-6}$alkoxy-$C_{1-6}$alkoxy-$C_{1-6}$alkyl, $C_{1-6}$-alkoxy-$C_{1-6}$ alkyl, (N—$C_{1-6}$alkoxy)-$C_{1-6}$alkylaminocarbonyl-$C_{1-6}$alkoxy, (N—$C_{1-6}$alkoxy)-$C_{1-6}$alkylaminocarbonyl-$C_{1-6}$alkyl, $C_{1-6}$alkoxy-$C_{1-6}$alkylcarbamoyl, $C_{1-6}$alkoxy-$C_{1-6}$alkylcarbonyl, $C_{1-6}$alkoxy-$C_{1-6}$alkylcarbonyl-amino, 1-$C_{1-6}$alkoxy-$C_{1-6}$alkylimidazol-2-yl, 2-$C_{1-6}$alkoxy-$C_{1-6}$alkyl-4-oxoimidazol-1-yl, 3-$C_{1-6}$alkoxy-$C_{1-6}$alkylpyrrolidinyl, 1-$C_{1-6}$ alkoxy-$C_{1-6}$alkyltetrazol-5-yl, 5-$C_{1-6}$alkoxy-$C_{1-6}$alkyl-tetrazol-1-yl, $C_{1-6}$alkoxyaminocarbonyl-$C_{1-6}$alkoxy, $C_{1-6}$alkoxyaminocarbonyl-$C_{1-6}$alkyl, $C_{1-6}$alkoxycarbonyl, $C_{1-6}$alkoxycarbonyl-$C_{1-6}$alkoxy, $C_{1-6}$alkoxycarbonyl-$C_{1-6}$ alkyl, $C_{1-6}$alkoxy-carbonylamino, $C_{1-6}$alkoxycarbonylamino-$C_{1-6}$alkoxy, $C_{1-6}$alkoxycarbonylamino-$C_{1-6}$alkyl, $C_{1-6}$alkyl, (N—$C_{1-6}$alkyl)-$C_{1-6}$alkoxy-$C_{1-6}$alkylcarbamoyl, (N—$C_{1-6}$alkyl)-$C_{1-6}$alkoxy-$C_{1-6}$alkyl-carbonylamino, (N—$C_{1-6}$alkyl)-$C_{1-6}$alkoxycarbonylamino, (N—$C_{1-6}$alkyl)-$C_{0-6}$alkylcarbonylamino-$C_{1-6}$alkoxy, (N—$C_{1-6}$alkyl)-$C_{0-6}$alkylcarbonylamino-$C_{1-6}$alkyl, (N—$C_{1-6}$alkyl)-$C_{1-6}$alkylsulphonyl-amino-$C_{1-6}$alkoxy, (N—$C_{1-6}$alkyl)-$C_{1-6}$ alkylsulphonylamino-$C_{1-6}$alkyl, $C_{1-6}$alkylamidinyl, $C_{1-6}$alkylamino, di-$C_{1-6}$alkylamino, $C_{1-6}$alkylamino-$C_{2-6}$ alkoxy, di-$C_{1-6}$alkylamino-$C_{2-6}$alkoxy, $C_{1-6}$alkylamino-$C_{1-6}$ alkyl, $C_{1-6}$alkylaminocarbonyl, $C_{1-6}$alkylaminocarbonyl-$C_{1-6}$alkoxy, di-$C_{1-6}$ alkylaminocarbonyl-$C_{1-6}$alkoxy, $C_{1-6}$alkylaminocarbonyl-$C_{1-6}$alkoxy-$C_{1-6}$alkyl, $C_{1-6}$alkyl-aminocarbonyl-$C_{1-6}$ alkyl, $C_{1-6}$alkylaminocarbonylamino-$C_{1-6}$alkoxy, $C_{1-6}$alkylaminocarbonyl-amino-$C_{1-6}$alkyl, di-$C_{1-6}$ alkylaminocarbonyl-$C_{1-6}$alkyl, $C_{1-6}$alkyl-carbamoyl, di-$C_{1-6}$ alkylcarbamoyl, $C_{0-6}$alkylcarbonylamino, $C_{0-6}$alkylcarbonylamino-$C_{1-6}$ alkoxy, $C_{0-6}$alkylcarbonylamino-$C_{1-6}$ alkyl, $C_{1-6}$alkylcarbonyloxy-$C_{1-6}$alkoxy, $C_{1-6}$alkylcarbonyloxy-$C_{1-6}$alkyl, $C_{1-6}$alkylenedioxy, $C_{1-6}$alkylsulphonyl, $C_{1-6}$alkylsulphonyl-$C_{1-6}$alkoxy, $C_{1-6}$alkyl-sulphonyl-$C_{1-6}$ alkyl, $C_{1-6}$alkylsulphonylamino-$C_{1-6}$alkoxy, $C_{1-6}$alkylsulphonylamino-$C_{1-6}$alkyl, amino, amino-$C_{2-7}$alkoxy, amino-$C_{1-6}$alkyl, aryl-$C_{1-6}$alkanoyl, benzoyloxy-$C_{2-6}$alkoxy, carbamoyl, carbamoyl-$C_{1-6}$alkoxy, carbamoyl-$C_{1-6}$alkyl, carboxy, carboxy-$C_{1-6}$alkoxy, carboxy-$C_{1-6}$alkoxy-$C_{1-6}$ alkyl, carboxy-$C_{1-6}$alkyl, cyano, cyano-$C_{1-6}$ alkoxy, cyano-$C_{1-6}$alkyl, $C_{3-8}$cyclo-alkyl-$C_{1-6}$alkanoyl, $C_{3-8}$cycloalkyl-$C_{0-6}$ alkoxy, $C_{3-8}$cycloalkyl-$C_{0-6}$ alkyl, $C_{3-8}$cycloalkylcarbonyl-amino, $C_{3-8}$cycloalkylcarbonylamino-$C_{1-6}$alkoxy, $C_{3-8}$cycloalkylcarbonylamino-$C_{1-6}$ alkyl, 3,4-dihydroxypyrrolidinyl, O,N-dimethylhydroxylamino-$C_{1-6}$alkyl, 2,6-dimethylmorpholinyl, 3,5-dimethylmorpholinyl, dioxanyl, dioxolanyl, dioxolanyl-$C_{1-6}$alkoxy, 4,4-dioxothiomorpholinyl, dithianyl, dithiolanyl, optionally $C_{1-6}$alkoxy-, $C_{1-6}$alkyl-, dihydroxy-$C_{1-6}$alkylaminocarbonyl- or halogen-substituted furyl, furyl-$C_{1-6}$alkoxy, furyl- $C_{1-6}$ alkyl, pyridyl, pyridyl-$C_{1-6}$alkoxy, pyridyl-$C_{1-6}$ alkyl, pyridylamino, pyridyloxy, pyridylthio, pyrimidinyl, pyrimidinyl-$C_{1-6}$alkoxy, pyrimidinyl-$C_{1-6}$alkyl, pyrimidinylamino, pyrimidinyloxy, pyrimidinylthio, thienyl, thienyl-$C_{1-6}$alkoxy or thienyl-$C_{1-6}$alkyl, halogen, heterocyclyl-$C_{1-6}$alkanoyl, hydroxy, hydroxy-$C_{2-6}$ alkoxy, hydroxy-$C_{2-6}$alkoxy-$C_{1-6}$ alkoxy, hydroxy-$C_{2-6}$ alkoxy-$C_{1-6}$alkyl, hydroxy-$C_{1-6}$alkyl, (N-hydroxy)-$C_{1-6}$ alkyl-aminocarbonyl-$C_{1-6}$alkoxy, (N-hydroxy)-$C_{1-6}$ alkylaminocarbonyl-$C_{1-6}$alkyl, (N-hydroxy) amino-carbonyl-$C_{1-6}$alkoxy, (N-hydroxy)aminocarbonyl-$C_{1-6}$alkyl, hydroxybenzyloxy, 2-hydroxymethylpyrrolidinyl, 4-hydroxypiperidinyl, 3-hydroxypyrrolidinyl, imidazolyl-$C_{1-6}$ alkoxy, imidazolyl-$C_{1-6}$alkyl, methoxybenzyloxy, methylenedioxybenzyloxy, 2-methylimidazolyl-$C_{1-6}$alkoxy, 2-methylimidazolyl-$C_{1-6}$ alkyl, 3-methyl-[1,2,4]-oxadiazol-5-yl-$C_{1-6}$alkoxy, 5-methyl-[1,2,4]-oxadiazol-3-yl-$C_{1-6}$ alkoxy, 3-methyl-[1,2,4]-oxadiazol-5-yl-$C_{1-6}$alkyl, 5-methyl-[1,2,4]-oxadiazol-3-yl-$C_{1-6}$alkyl, O-methyloximyl-$C_{1-6}$ alkyl, 4-methylpiperazinyl, N-methylpiperazino-$C_{1-6}$ alkoxy, N-methylpiperazino-$C_{1-6}$ alkoxy-$C_{1-6}$alkyl, N-methylpiperazino-$C_{1-6}$alkyl, 5-methyltetrazol-1-yl-$C_{1-6}$ alkoxy, 5-methyltetrazol-1-yl-$C_{1-6}$alkyl, morpholinyl, morpholino-$C_{1-6}$alkoxy, morpholino-$C_{1-6}$alkoxy-$C_{1-6}$alkyl, morpholino-$C_{1-6}$alkyl, nitro, [1,2,4]-oxadiazol-5-yl-$C_{1-6}$alkoxy, [1,2,4]-oxadiazol-5-yl-$C_{1-6}$alkyl, oxazol-4-yl-$C_{1-6}$alkoxy, oxazol-4-yl-$C_{1-6}$alkyl, oxide, oxo, 2-oxoimidazolidinyl, 2-oxo-[1,3]oxazinyl, 2-oxooxazolidinyl, 2-oxooxazolidinyl-$C_{1-6}$alkoxy, 2-oxooxazolidinyl-$C_{1-6}$ alkyl, 4-oxopiperidinyl, 2-oxopyrrolidinyl, 2-oxopyrrolidinyl-$C_{1-6}$alkoxy, 2-oxopyrrolidinyl-$C_{1-6}$ alkyl, 2-oxotetrahydropyrimidinyl, 4-oxothiomorpholinyl, optionally $C_{1-6}$alkoxy-, $C_{1-6}$-alkoxycarbonyl-, $C_{1-6}$alkyl-, $C_{1-6}$alkylamino-, di-$C_{1,6}$alkylamino-, halogen-, hydroxy-, hydroxy-$C_{1-6}$alkyl- or trifluoromethyl-substituted phenoxy, phenyl, phenyl-$C_{1-6}$alkoxy, phenyl-$C_{1-6}$alkyl or phenylthio, piperazinyl, piperazino-$C_{1-6}$alkoxy, piperazino-$C_{1-6}$alkoxy-$C_{1-6}$ alkyl, piperazino-$C_{1-6}$alkyl, piperidinyl, piperidino-$C_{1-6}$ alkoxy, piperidino-$C_{1-6}$alkoxy-$C_{1-6}$alkyl, polyhalogen-$C_{1-6}$ alkoxy, polyhalogen-$C_{1-6}$alkyl, pyridylcarbamoyloxy-$C_{1-6}$ alkoxy, pyridylcarbonylamino-$C_{1-6}$alkyl, pyrrolidinyl, pyrrolyl, tetrazol-1-yl-$C_{1-6}$alkoxy, tetrazol-2-yl-$C_{1-6}$alkoxy, tetrazol-5-yl-$C_{1-6}$alkoxy, tetrazol-2-yl-$C_{1-6}$alkyl, tetrazol-5-yl-$C_{1-6}$alkyl, thiazol-4-yl-$C_{1-6}$ alkoxy, thiazol-4-yl-$C_{1-6}$ alkyl, thiomorpholinyl, [1,2,4]-triazol-1-yl-$C_{1-6}$alkoxy, [1,2,4]-triazol-4-yl-$C_{1-6}$alkoxy, [1,2,4]-triazol-1-yl-$C_{1-6}$alkyl, [1,2,4]-triazol-4-yl-$C_{1-6}$alkyl and the radical —O—$CH_2CH(OH)CH_2NRx$, where NRx is a mono- or di-$C_{1-6}$alkylamino, N-methylpiperazino, morpholino, piperazino or piperidino radical.

$R^6$ as bicyclo[x.y.z]alkyl is for example bicyclo[3.1.0]-hexanyl, bicyclo[2.1.1]-hexyl, bicyclo[4.1.0]-heptyl, bicyclo[2.2.1]heptyl, bicyclo[3.2.0]-heptyl and bicyclo[4.2.0]octyl, with preference for bicyclo[3.1.0]hex-6-yl and bicyclo[3.1.0]hex-3-yl.

$R^6$ as spiro[o.p]alkyl is for example spiro[2.4]heptyl, spiro[2.5]octyl and spiro[3.4]octyl.

$R^6$ as mono- or bioxabicyclo[x.y.z]alkyl is for example 2-oxabicyclo[3.1.0]hexyl, 3-oxa-bicyclo[3.1.0]hexyl, 2-oxabicyclo[4.1.0]heptyl, 3-oxabicyclo[4.1.0]heptyl, 2,5-dioxabicyclo[4.1.0]heptyl, 3-oxabicyclo[3.3.1]nonyl, 2-oxabicyclo[2.2.1]heptyl, 7-oxa-bicyclo[2.2.1]heptyl and 2,4-dioxabicyclo[3.1.0]hexyl, with preference for 2-oxa-bicyclo[3.1.0]hex-1-yl, 2-oxabicyclo[3.1.0]hex-6-yl, 3-oxabicyclo[3.1.0]hex-1-yl, 3-oxa-bicyclo[3.1.0]hex-6-yl, 3-oxabicyclo[3.1.0]hex-2-yl, 2,5-dioxabicyclo[4.1.0]hept-7-yl, 2-oxabicyclo[4.1.0]hept-7-yl, 3-oxabicyclo[3.3.1]non-9-yl, 7-oxabicyclo[2.2.1]hept-2-yl, 2-oxa-bicyclo[2.2.1]hept-6-yl.

$R^6$ as mono- or bioxaspiro[o.p]alkyl is for example 1-oxaspiro[2.5]octyl, 6-oxaspiro[2.5]octyl, 5-oxaspiro[2.4]hept, 1-oxaspiro[2.4]heptyl, with preference for 1-oxaspiro[2.5] oct-6-yl and 6-oxaspiro[2.5]oct-1-yl.

Halogen is for example F, Cl, Br or I, preferably F or Cl.

Polyhalogen-$C_{1-6}$alkoxy is for example alkoxy substituted one or more times by fluorine, chlorine, bromine or iodine, also including mixed, e.g. fluorine and chlorine, substitutions, with preference for perfluorinated radicals such as trifluoromethoxy.

Polyhalogen-$C_{1-6}$alkyl is for example alkyl substituted one or more times by fluorine, chlorine, bromine or iodine, also including mixed, e.g. fluorine and chlorine, substitutions, with preference for perfluorinated radicals such as trifluoromethyl.

Examples of $C_{1-6}$alkyl and -alkoxy radicals are methyl, ethyl, n-propyl, isopropyl, n-butyl, isobutyl, sec-butyl, tert-butyl, pentyl, hexyl, and methoxy, ethoxy, propoxy, isopropoxy, butoxy, isobutoxy, sec-butoxy and tert-butoxy.

$C_{1-6}$Alkylenedioxy radicals are preferably methylenedioxy, ethylenedioxy and propylenedioxy. Examples of $C_{1-6}$-alkanoyl radicals are acetyl, propionyl and butyryl.

Cycloalkyl is a saturated, cyclic hydrocarbon radical having 3-8 carbon atoms, e.g. cyclopropyl, cyclobutyl, cyclopentyl and cyclohexyl.

Examples of $C_{1-6}$alkylene radicals are methylene, ethylene, propylene, 2-methylpropylene, tetra-, penta- and hexamethylene; examples of $C_{2-6}$alkenylene radicals are vinylene and propenylene; an example of $C_{2-6}$alkynylene radicals is ethynylene; and acyl radicals are alkanoyl radicals, preferably $C_{1-6}$alkanoyl radicals, or aroyl radicals such as benzoyl. Aryl designates mono- or polynuclear aromatic radicals which may be substituted one or more times, such as, for example, phenyl, substituted phenyl, naphthyl, substituted naphthyl, tetrahydronaphthyl or substituted tetrahydronaphthyl.

The compounds of the formula (I) have at least four asymmetric carbon atoms and can therefore exist in the form of optically pure diastereomers, mixtures of diastereomers, diastereomeric racemates, mixtures of diastereomeric racemates or as meso compounds. The invention includes all these forms. Mixtures of diastereomers, diastereomeric racemates or mixtures of diastereomeric racemates can be fractionated by conventional methods, e.g. by column chromatography, thin-layer chromatography, HPLC and the like.

Salts of compounds with salt-forming groups are in particular acid addition salts, salts with bases or, if a plurality of salt-forming groups is present, optionally also mixed salts or inner salts.

Salts are primarily the pharmaceutically acceptable or non-toxic salts of compounds of the formula (I).

Such salts are formed for example by compounds of the formula (I) having an acidic group, e.g. a carboxy or sulpho group, and are for example their salts with suitable bases, such as non-toxic metal salts derived from metals of group Ia, Ib, IIa and IIb of the Periodic Table of the Elements, e.g. alkali metal, in particular lithium, sodium or potassium, salts, alkaline earth metal salts, for example magnesium or calcium salts, furthermore zinc salts or ammonium salts, also salts formed with organic amines such as optionally hydroxy-substituted mono-, di- or trialkylamines, especially mono-, di- or tri-lower-alkylamines, or with quaternary ammonium bases, e.g. methyl-, ethyl-, diethyl- or triethylamine, mono-, bis- or tris(2-hydroxy-lower-alkyl)amines such as ethanol-, diethanol- or triethanolamine, tris(hydroxy-methyl)methylamine or 2-hydroxy-tertiary-butylamine, N,N-di-lower-alkyl-N-(hydroxy-lower-alkyl)amine, such as N,N-dimethyl-N-(2-hydroxyethyl)amine, or N-methyl-D-glucamine, or quaternary ammonium hydroxides such as tetrabutylammonium hydroxide. Under lower-alkyl is understood an alkyl group having 1 to 6 C-atoms. The compounds of the formula I having a basic group, e.g. an amino group, can form acid addition salts, e.g. with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, furthermore amino acids such as, for example, the α-amino acids mentioned hereinbelow, and methanesulphonic acid, ethanesulphonic acid, 2-hydroxyethanesulphonic acid, ethane-1,2-disulphonic acid, benzene-sulphonic acid, 4-toluenesulphonic acid, naphthalene-2-sulphonic acid, 2- or 3-phosphoglycerate, glucose 6-phosphate, N-cyclohexylsulphamic acid (to form cyclamates) or with other acidic organic compounds such as ascorbic acid. Compounds of the formula (I) having acidic and basic groups may also form inner salts.

Pharmaceutically unsuitable salts may also be used for isolation and purification.

The groups of compounds mentioned hereinafter are not to be regarded as closed; on the contrary, it is possible for parts of these groups of compounds to be interchanged or replaced by the definitions given above, or omitted, in a worthwhile manner, e.g. to replace general by more specific definitions.

Preferred compounds according to the invention are those of the general formula (IA)

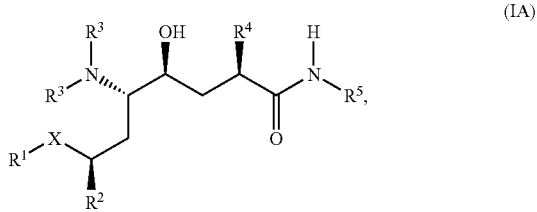

in which $R^1$, $R^2$, $R^3$, $R^4$, $R^5$ and X have the meaning indicated above for compounds of the formula (I).

A further preferred group of compounds of the formula (I), or particularly preferably of the formula (IA), are compounds in which at least one, very particularly preferably all, substituent(s) is (are) defined as follows:
X is $CH_2$;
$R^1$ has the meaning as indicated above;
$R^2$ is $C_{1-6}$alkyl;
$R^3$ is H;
$R^4$ is $C_{1-6}$alkyl;
$R^5$ has the meaning as indicated above;
L, n, m have the meanings as indicated above;
$R^6$ is a radical composed of 2 cyclic systems and selected from bicyclo[x.y.z]alkyl, spiro[o.p]alkyl, mono- or bioxabicyclo[x.y.z]alkyl or mono- or bioxaspiro[o.p] alkyl, all of which may be substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino;
o, p, x, y and z have the meanings as indicated above;
and pharmaceutically useable salts thereof.

Particularly preferred radicals $R^1$ are benzoimidazolyl, quinazolinyl, quinolyl, quinoxalinyl, imidazolyl, imidazo[1,5-a]pyridinyl, imidazo[1,2-a]pyrimidinyl, indazolyl, indolyl, isoquinolyl, pyrimidinyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl and [1,2,4]triazolo[4,3-a]pyridinyl, which are substituted by one to four radicals independently of one another selected from acetamidinyl-$C_{1-6}$alkyl, 3-acetamidomethylpyrrolidinyl, acyl-$C_{1-6}$ alkoxy-$C_{1-6}$alkyl, (N-acyl)-$C_{1-6}$alkoxy-$C_{1-6}$alkylamino, $C_{1-6}$alkanoyl, $C_{1-6}$alkanoyloxy, $C_{2-6}$alkenyl, $C_{2-6}$alkenyloxy, $C_{2-6}$alkenyloxy-$C_{1-6}$alkyl, $C_{1-6}$alkoxy, $C_{1-6}$alkoxy-$C_{1-6}$ alkoxy, $C_{1-6}$-alkoxy-$C_{1-6}$alkoxy-$C_{1-6}$alkyl, $C_{1-6}$alkoxy-$C_{1-6}$ alkyl, (N—$C_{1-6}$alkoxy)-$C_{1-6}$alkylaminocarbonyl-$C_{1-6}$ alkoxy, (N—$C_{1-6}$alkoxy)-$C_{1-6}$alkylaminocarbonyl-$C_{1-6}$ alkyl, $C_{1-6}$alkoxy-$C_{1-6}$alkylcarbamoyl, $C_{1-6}$alkoxy-$C_{1-6}$ alkylcarbonyl, $C_{1-6}$alkoxy-$C_{1-6}$alkylcarbonylamino, 1-$C_{1-6}$ alkoxy-$C_{1-6}$alkylimidazol-2-yl, 2-$C_{1-6}$alkoxy-$C_{1-6}$alkyl-4-oxoimidazol-1-yl, 3-$C_{1-6}$alkoxy-$C_{1-6}$alkylpyrrolidinyl, 1-$C_{1-6}$ alkoxy-$C_{1-6}$alkyltetrazol-5-yl, 5-$C_{1-6}$alkoxy-$C_{1-6}$ alkyltetrazol-1-yl, $C_{1-6}$alkoxyaminocarbonyl-$C_{1-6}$alkoxy, $C_{1-6}$alkoxyamino-carbonyl-$C_{1-6}$alkyl, $C_{1-6}$alkoxycarbonyl, $C_{1-6}$alkoxycarbonyl-$C_{1-6}$alkoxy, $C_{1-6}$alkoxycarbonyl-$C_{1-6}$ alkyl, $C_{1-6}$alkoxycarbonylamino, $C_{1-6}$alkoxycarbonylamino-$C_{1-6}$alkoxy, $C_{1-6}$alkoxycarbonyl-amino-$C_{1-6}$alkyl, $C_{1-6}$alkyl, (N—$C_{1-6}$alkyl)-$C_{1-6}$alkoxy-$C_{1-6}$alkylcarbamoyl, (N—$C_{1-6}$ alkyl)-$C_{1-6}$alkoxy-$C_{1-6}$alkylcarbonylamino, (N—$C_{1-6}$ alkyl)-$C_{1-6}$alkoxycarbonylamino, (N—$C_{1-6}$alkyl)-$C_{0-6}$alkyl-carbonylamino-$C_{1-6}$alkoxy, (N—$C_{1-6}$alkyl)-$C_{0-6}$ alkylcarbonylamino-$C_{1-6}$alkyl, (N—$C_{1-6}$alkyl)-$C_{1-6}$alkylsulphonylamino-$C_{1-6}$alkoxy, (N—$C_{1-6}$alkyl)-$C_{1-6}$ alkylsulphonylamino-$C_{1-6}$alkyl, $C_{1-6}$alkylamidinyl, $C_{1-6}$alkylamino, di-$C_{1-6}$alkylamino, $C_{1-6}$alkylamino-$C_{2-6}$ alkoxy, di-$C_{1-6}$alkylamino-$C_{2-6}$alkoxy, $C_{1-6}$alkylamino-$C_{1-6}$ alkyl, $C_{1-6}$alkylaminocarbonyl, $C_{1-6}$alkyl-aminocarbonyl-$C_{1-6}$alkoxy, di-$C_{1-6}$alkylaminocarbonyl-$C_{1-6}$alkoxy, $C_{1-6}$alkylaminocarbonyl-$C_{1-6}$alkoxy-$C_{1-6}$alkyl, $C_{1-6}$alkylaminocarbonyl-$C_{1-6}$ alkyl, $C_{1-6}$alkylaminocarbonylamino-$C_{1-6}$alkoxy, $C_{1-6}$alkylaminocarbonylamino-$C_{1-6}$alkyl, di-$C_{1-6}$ alkylaminocarbonyl-$C_{1-6}$alkyl, di-$C_{1-6}$alkylamino-$C_{1-6}$ alkyl, $C_{1-6}$alkylcarbamoyl, di-$C_{1-6}$alkylcarbamoyl, $C_{0-6}$alkylcarbonylamino, $C_{0-6}$alkylcarbonylamino-$C_{1-6}$ alkoxy, $C_{0-6}$alkylcarbonylamino-$C_{1-6}$alkyl, $C_{1-6}$alkylcarbonyloxy-$C_{1-6}$alkoxy, $C_{1-6}$alkylcarbonyloxy-$C_{1-6}$alkyl, $C_{1-6}$alkylenedioxy, $C_{1-6}$alkylsulphonyl, $C_{1-6}$alkyl-sulphonyl-$C_{1-6}$alkoxy, $C_{1-6}$alkylsulphonyl-$C_{1-6}$alkyl, $C_{1-6}$alkylsulphonylamino-$C_{1-6}$ alkoxy, $C_{1-6}$alkylsulphonylamino-$C_{1-6}$alkyl, amino, amino-$C_{2-7}$alkoxy, amino-$C_{1-6}$alkyl, aryl-$C_{1-6}$alkanoyl, benzoyloxy-$C_{2-6}$alkoxy, carbamoyl, carbamoyl-$C_{1-6}$ alkoxy, carbamoyl-$C_{1-6}$alkyl, carboxy, carboxy-$C_{1-6}$alkoxy, carboxy-$C_{1-6}$alkoxy-$C_{1-6}$alkyl, carboxy-$C_{1-6}$alkyl, cyano, cyano-$C_{1-6}$alkoxy, cyano-$C_{1-6}$alkyl, $C_{3-6}$cycloalkyl-$C_{1-6}$alkanoyl, $C_{3-6}$cycloalkyl-$C_{0-6}$alkoxy, $C_{3-8}$cyclo-alkyl-$_{0-6}$alkyl, $C_{3-8}$cycloalkylcarbonylamino, $C_{3-8}$cycloalkylcarbonylamino-$C_{1-6}$alkoxy, $C_{3-8}$cycloalkylcarbonylamino-$C_{1-6}$alkyl, 3,4-dihydroxypyrrolidinyl, O,N-dimethylhydroxylamino-$C_{1-6}$alkyl, 2,6-dimethylmorpholinyl, 3,5-dimethylmorpholinyl, dioxanyl, dioxolanyl, dioxolanyl-$C_{1-6}$alkoxy, 4,4-dioxothiomorpholinyl, dithianyl, dithiolanyl, optionally $C_{1-6}$alkoxy-, dihydroxy-$C_{1-6}$alkylaminocarbonyl- or halogen-substituted furyl, furyl-$C_{1-6}$alkoxy, furyl-$C_{1-6}$alkyl, pyridyl, pyridyl-$C_{1-6}$alkoxy, pyridyl-$C_{1-6}$alkyl, pyridylamino, pyridyloxy, pyridylthio, pyrimidinyl, pyrimidinyl-$C_{1-6}$alkoxy, pyrimidinylamino, pyrimidinyloxy, pyrimidinylthio, thienyl, thienyl-$C_{1-6}$alkoxy or thienyl-$C_{1-6}$alkyl, halogen, heterocyclyl-$C_{1-6}$alkanoyl, hydroxy, hydroxy-$C_{2-6}$ alkoxy, hydroxy-$C_{2-6}$alkoxy-$C_{1-6}$alkoxy, hydroxy-$C_{2-6}$alkoxy-$C_{1-6}$alkyl, hydroxy-$C_{1-6}$alkyl, (N-hydroxy)-$C_{1-6}$alkylaminocarbonyl-$C_{1-6}$alkoxy, (N-hydroxy)-$C_{1-6}$ alkylaminocarbonyl-$C_{1-6}$alkyl, (N-hydroxy)aminocarbonyl-$C_{1-6}$ alkoxy, (N-hydroxy)amino-carbonyl-$C_{1-6}$alkyl, hydroxylbenzyloxy, 2-hydroxymethylpyrrolidinyl, 4-hydroxypiperidinyl, 3-hydroxypyrrolidinyl, imidazolyl-$C_{1-6}$alkoxy, imidazolyl-$C_{1-6}$ alkyl, methoxybenzyloxy, methylenedioxybenzyloxy, 2-methylimidazolyl-$C_{1-6}$alkoxy, 2-methylimidazolyl-$C_{1-6}$alkyl, 3-methyl-[1,2,4]-oxadiazol-5-yl-$C_{1-6}$alkoxy, 5-methyl-[1,2,4]-oxadiazol-3-yl-$C_{1-6}$alkoxy, 3-methyl-[1,2,4]-oxadiazol-5-yl-$C_{1-6}$alkyl, 5-methyl-[1,2,4]-oxadiazol-3-yl-$C_{1-6}$alkyl, O-methyl-oximyl-$C_{1-6}$ alkyl, 4-methylpiperazinyl, N-methylpiperazino-$C_{1-6}$ alkoxy, N-methylpiperazino-$C_{1-6}$ alkoxy-$C_{1-6}$alkyl, N-methylpiperazinyl-$C_{1-6}$alkyl, 5-methyltetrazol-1-yl-$C_{1-6}$ alkoxy, 5-methyl-tetrazol-1-yl-$C_{1-6}$alkyl, morpholinyl, morpholino-$C_{1-6}$alkoxy, morpholino-$C_{1-6}$ alkoxy-$C_{1-6}$alkyl, morpholino-$C_{1-6}$alkyl, nitro, [1,2,4]-oxadiazol-5-yl-$C_{1-6}$ alkoxy, [1,2,4]-oxadiazol-5-yl-$C_{1-6}$alkyl, oxazol-4-yl-$C_{1-6}$ alkoxy, oxazol-4-yl-$C_{1-6}$alkyl, oxide, oxo, 2-oxoimidazolidinyl, 2-oxo-[1,3]-oxazinyl, 2-oxooxazolidinyl, 2-oxooxazolidinyl-$C_{1-6}$alkoxy, 2-oxooxazolidinyl-$C_{1-6}$alkyl, 4-oxopiperidinyl, 2-oxopyrrolidinyl, 2-oxopyrrolidinyl-$C_{1-6}$ alkoxy, 2-oxopyrrolidinyl-$C_{1-6}$alkyl, 2-oxotetrahydropyrimidinyl, 4-oxothiomorpholinyl, optionally $C_{1-6}$alkoxy-, $C_{1-6}$alkoxycarbonyl-, $C_{1-6}$alkyl-, $C_{1-6}$alkylamino-, di-$C_{1,6}$alkylamino-, halogen-, hydroxyl-, hydroxy-$C_{1-6}$alkyl- or trifluoromethyl-substituted phenoxy, phenyl, phenyl-$C_{1-6}$ alkoxy, phenyl-$C_{1-6}$alkyl or phenylthio, piperazinyl, piperazino-$C_{1-6}$alkoxy, piperazino-$C_{1-6}$alkoxy-$C_{1-6}$ alkyl, piperazino-$C_{1-6}$alkyl, piperidinyl, piperidino-$C_{1-6}$ alkoxy, piperidino-$C_{1-6}$alkoxy-$C_{1-6}$alkyl, polyhalogen-$C_{1-6}$ alkoxy, polyhalogen-$C_{1-6}$alkyl, pyridylcarbamoyloxy-$C_{1-6}$ alkoxy, pyridylcarbonylamino-$C_{1-6}$alkyl, pyrrolidinyl, pyrrolyl, tetrazol-1-yl-$C_{1-6}$alkoxy, tetrazol-2-yl-$C_{1-6}$alkoxy, tetrazol-5-yl-$C_{1-6}$alkoxy, tetrazol-1-yl-$C_{1-6}$alkyl, tetrazol-2-yl-$C_{1-6}$ alkyl, tetrazol-5-yl-$C_{1-6}$alkyl, thiazol-4-yl-$C_{1-6}$alkoxy, thiazol-4-yl-$C_{1-6}$alkyl, thiomorpholinyl, [1,2,4]-triazol-1-yl-$C_{1-6}$alkoxy, [1,2,4]-triazol-4-yl-$C_{1-6}$alkoxy, [1,2,4]-triazol-1-yl-$C_{1-6}$alkyl, [1,2,4]-triazol-4-yl-$C_{1-6}$alkyl and the radical —O—$CH_2CH(OH)CH_2NRx$, where NRx is a mono- or di-$C_{1-6}$alkylamino, N-methylpiperazino, morpholino, piperazino or piperidino radical, and where in the case where $R^1$ is a bicyclic heterocyclic ring system, at least the ring not bonded to X is substituted as indicated.

Further particularly preferred radicals $R^1$ are benzoimidazolyl, imidazo[1,2-a]pyrimidinyl, imidazo[1,2-a]pyridinyl, imidazo[1,5-a]pyridinyl, indazolyl, indolyl, pyridinyl, pyrrolo[2,3-b]pyridinyl, pyrrolo[3,2-c]pyridinyl, pyrrolo[2,3-c] pyridinyl, pyrrolo[3,2-b]pyridinyl, [1,2,3]-triazolo[1,5-a]pyridinyl and [1,2,4]-triazolo[4,3-a]pyridinyl, where the said radicals are substituted by one to four radicals independently of one another selected from $C_{1-6}$alkanoyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino-$C_{1-6}$alkoxy, $C_{1-6}$alkoxycarbonylamino-$C_{1-6}$ alkyl, $C_{1-6}$alkyl, $C_{0-6}$alkylcarbonylamino-$C_{1-6}$alkoxy, $C_{0-6}$alkyl-carbonylamino-$C_{1-6}$alkyl, carbamoyl, carboxyl, cyano, halogen, hydroxy, hydroxy-$C_{2-6}$alkoxy, hydroxy-$C_{1-6}$ alkyl, oxide, polyhalo-$C_{1-6}$alkoxy, polyhalo-$C_{1-6}$alkyl and trifluoromethyl, where in the case where $R^1$ is a bicyclic heterocyclic ring system, at least the ring not bonded to X is substituted as indicated.

$R^6$ is preferably,
if m is 0, a saturated $C_{3-8}$heterocyclyl which comprises 1-2 oxygen atoms, substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino, or
if m is 1, a saturated $C_{3-8}$heterocyclyl which comprises 1-2 oxygen atoms, optionally substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino.

$R^6$ is particularly preferably a radical composed of 2 cyclic systems selected from bicyclo[x.y.z]alkyl, spiro[o.p]alkyl, mono- or bioxabicyclo[x.y.z]alkyl or mono- or bioxaspiro-[o.p]alkyl, all of which may be substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino.

The compounds of the formula (I) can be prepared in an analogous manner to the preparation process disclosed in the literature. Similar preparation processes are described for example in EP 678503, WO 01/09079, WO 01/09083, WO 02/02487, WO 02/02500, WO 02/02508, WO 02/08172, WO 02/092828 and in Helvetica Chemica Acta 86 (2003), 2848-2870 and in literature cited therein (scheme).

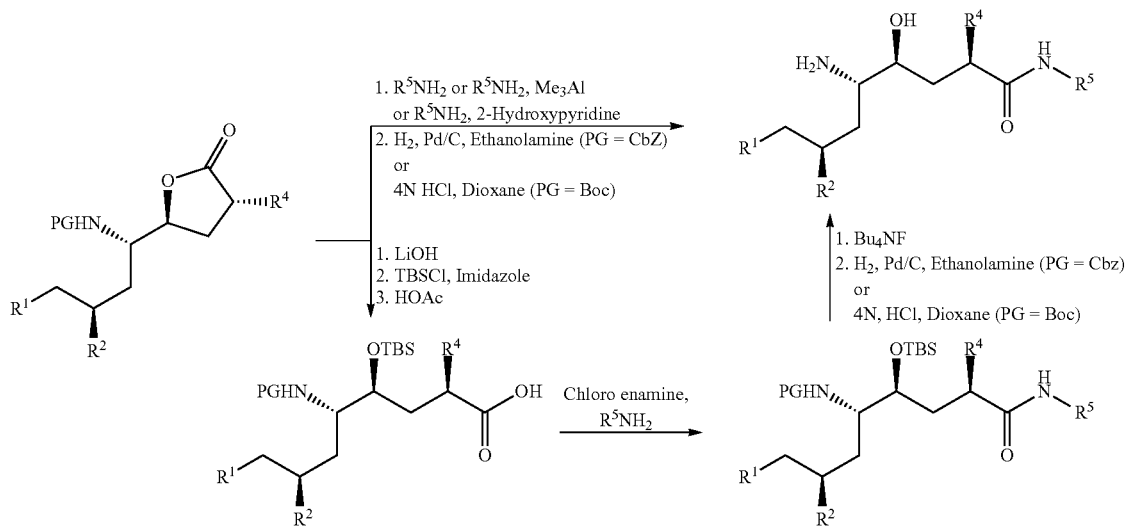

Details of the specific preparation variants can be found in the examples.

The compounds of the formula (I) can also be prepared in optically pure form. Separation into antipodes can take place by methods known per se, either preferably at an early stage in the synthesis by salt formation with an optically active acid such as, for example, (4)- or (−)-mandelic acid and separation of the diastereomeric salts by fractional crystallization or preferably at a rather late stage by derivatizing with a chiral auxiliary component such as, for example, (+)- or (−)-camphanoyl chloride, and separation of the diastereomeric products by chromatography and/or crystallization and subsequent cleavage of the linkage to the chiral auxiliary. The pure diastereomeric salts and derivatives can be analysed to determine the absolute configuration of the contained piperidine by conventional spectroscopic methods, with X-ray spectroscopy on single crystals representing a particularly suitable method.

Prodrug derivatives of the compounds described herein are derivatives thereof which on in vivo use liberate the original compound by a chemical or physiological process. A prodrug may for example be converted into the original compound when a physiological pH is reached or by enzymatic conversion. Possible examples of prodrug derivatives are esters of freely available carboxylic acids, S- and O-acyl derivatives of thiols, alcohols or phenols, the acyl group being defined as above. Preferred derivatives are pharmaceutically acceptable ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters such as lower ω-(amino, mono- or dialkylamino, carboxy, lower alkoxycarbonyl)-alkyl esters or such as lower α-(alkanoyloxy, alkoxycarbonyl or dialkylaminocarbonyl)-alkyl esters; conventionally, pivaloyloxymethyl esters and similar esters are used as such.

Because of the close relationship between a free compound, a prodrug derivative and a salt compound, a particular compound in this invention also includes its prodrug derivative and salt form, where this is possible and appropriate.

The compounds of the formula (I) also include compounds in which one or more atoms are replaced by their stable, non-radioactive isotopes; for example a hydrogen atom by deuterium.

The compounds of the formula (I), and of the formula (IA), and their pharmaceutically acceptable salts have an inhibitory effect on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II raises the blood pressure both directly by arterial constriction, and indirectly by releasing the hormone aldosterone, which retains sodium ions, from the adrenals, which is associated with an increase in the extracellular fluid volume. This increase is attributable to the effect of angiotensin II itself or of the heptapeptide angiotensin III formed therefrom as cleavage product. Inhibitors of the enzymatic activity of renin bring about a reduction in the formation of angiotensin I and, as a consequence thereof, the formation of a smaller amount of angiotensin II. The reduced concentration of this active peptide hormone is the direct cause of the blood pressure-lowering effect of renin inhibitors.

The effect of renin inhibitors is detected inter alia experimentally by means of in vitro tests where the reduction in the formation of angiotensin I is measured in various systems (human plasma, purified human renin together with synthetic or natural renin substrate). The following in vitro test of Nussberger et al. (1987) J. Cardiovascular Pharmacol., Vol. 9, pp. 39-44, is used, inter alia. This test measures the formation of angiotensin I in human plasma. The amount of angiotensin I formed is determined in a subsequent radio-immunoassay. The effect of inhibitors on the formation of angiotensin I is tested in this system by adding various concentrations of these substances. The $IC_{50}$ is defined as the concentration of the particular inhibitor which reduces the formation of angiotensin I by 50%. The compounds of the present invention show inhibitory effects in the in vitro systems at minimal concentrations of about $10^{-6}$ to about $10^{-10}$ mol/l.

Examples of the inhibition:

| Example number | $IC_{50}$ values [nM] |
|---|---|
| 3FFF | 5.3 |
| 7BBBB | 1.3 |
| 7DDDD | 1.7 |
| 32JJJ | 2.6 |
| 36BBBB | 4.8 |

| Example number | $IC_{50}$ values [nM] |
|---|---|
| 36DDDD | 3.1 |
| 36HHHH | 2.9 |
| 36IIII | 3.5 |
| 40DDDD | 0.5 |

Renin inhibitors bring about a fall in blood pressure in salt-depleted animals. Human renin differs from renin of other species. Inhibitors of human renin are tested using primates (marmosets, *Callithrix jacchus*) because human renin and primate renin are substantially homologous in the enzymatically active region. The following in vivo test is employed inter alia: the test compounds are tested on normotensive marmosets of both sexes with a body weight of about 350 g, which are conscious, unrestrained and in their normal cages. Blood pressure and heart rate are measured with a Catheter, in the descending aorta and are recorded radiometrically. Endogenous release of renin is stimulated by combining a low-salt diet for 1 week with a single intramuscular injection of furosemide (5-(aminosulphonyl)-4-chloro-2-[(2-furanylmethyl)amino]benzoic acid) (5 mg/kg). 16 hours after the furosemide injection, the test substances are administered either directly into the femoral artery by means of a hypodermic needle or as suspension or solution by gavage into the stomach, and their effect on blood pressure and heart rate is evaluated. The compounds of the present invention have a blood pressure-lowering effect in the described in vivo test with i.v. doses of about 0.003 to about 0.3 mg/kg and with oral doses of about 0.3 to about 30 mg/kg.

The blood pressure-reducing effect of the compounds described herein can be tested in vivo using the following protocol:

The investigations take place in 5 to 6-week old, male double transgenic rats (dTGR), which overexpress both human angiotensinogen and human renin and consequently develop hypertension (Bohlender J. et al., J Am Soc Nephrol 2000; 11: 2056-2061). This double transgenic rat strain was produced by crossbreeding two transgenic strains, one for human angiotensinogen with the endogenous promoter and one for human renin with the endogenous promoter. Neither single transgenic strain was hypertensive. The double transgenic rats, both males and females, develop severe hypertension (mean systolic pressure, approximately 200 mm Hg) and die after a median of 55 days if untreated. The fact that human renin can be studied in the rat is a unique feature of this model.

Age-matched Sprague-Dawley rats serve as non-hypertensive control animals. The animals are divided into treatment groups and receive test substance or vehicle (control) for various treatment durations. The applied doses for oral administration may range from 0.5 to 100 mg/kg body weight. Throughout the study, the animals receive standard feed and tap water ad libitum. The systolic and diastolic blood pressure, and the heart rate are measured telemetrically by means of transducers implanted in the abdominal aorta, allowing the animals free and unrestricted movement.

The effect of the compounds described herein on kidney damage (proteinuria) can be tested in vivo using the following protocol:

The investigations take place in 4-week old, male double transgenic rats (dTGR), as described above. The animals are divided into treatment groups and receive test substance or vehicle (control) each day for 7 weeks. The applied doses for oral administration may range from 0.5 to 100 mg/kg body weight. Throughout the study, the animals receive standard feed and tap water ad libitum. The animals are placed periodically in metabolism cages in order to determine the 24-hour urinary excretion of albumin, diuresis, natriuresis, and urine osmolality. At the end of the study, the animals are sacrificed and the kidneys and hearts may also be removed for determining the weight and for immunohistological investigations (fibrosis, macrophage/T-cell infiltration, etc.).

The pharmacokinetic properties of the compounds described herein can be tested in vivo using the following protocol:

The investigations take place in pre-catheterized (carotid artery) male rats (300 g±20%) that can move freely throughout the study. The compound is administered intravenously and orally (gavage) in separate sets of animals. The applied doses for oral administration may range from 0.5 to 50 mg/kg body weight; the doses for intravenous administration may range from 0.5 to 20 mg/kg body weight. Blood samples are collected through the catheter before compound administration and over the subsequent 24-hour period using an automated sampling device (AccuSampler, DiLab Europe, Lund, Sweden). Plasma levels of the compound are determined using a validated LC-MS analytical method. The pharmacokinetic analysis is performed on the plasma concentration-time curves after averaging all plasma concentrations across time points for each route of administration. Typical pharmacokinetics parameters to be calculated include: maximum concentration ($C_{max}$), time to maximum concentration ($t_{max}$), area under the curve from 0 hours to the time point of the last quantifiable concentration ($AUC_{0-t}$), area under the curve from time 0 to infinity ($AUC_{0-inf}$), elimination rate constant (K), terminal half-life ($t_{1/2}$), absolute oral bioavailability or fraction absorbed (F), clearance (CL), and Volume of distribution during the terminal phase (Vd).

The compounds of the formula (I), and preferably of the formula (IA), and their pharmaceutically acceptable salts can be used as medicines, e.g. in the form of pharmaceutical products. The pharmaceutical products can be administered enterally, such as orally, e.g. in the form of tablets, lacquered tablets, sugar-coated tablets, hard and soft gelatine capsules, solutions, emulsions or suspensions, nasally, e.g. in the form of nasal sprays, rectally, e.g. in the form of suppositories, or transdermally, e.g. in the form of ointments or patches. However, administration is also possible parenterally, such as intramuscularly or intravenously, e.g. in the form of solutions for injection.

Tablets, lacquered tablets, sugar-coated tablets and hard gelatine capsules can be produced by processing the compounds of the formula (I), or preferably of the formula (IA), and their pharmaceutically acceptable salts with pharmaceutically inert inorganic or organic excipients. Excipients of these types which can be used for example for tablets, sugar-coated tablets and hard gelatine capsules are lactose, maize starch or derivatives thereof, talc, stearic acid or salts thereof etc.

Excipients suitable for soft gelatine capsules are, for example, vegetable oils, waxes, fats, semisolid and liquid polyols etc.

Excipients suitable for producing solutions and syrups are, for example, water, polyols, sucrose, invert sugar, glucose etc.

Excipients suitable for solutions for injection are, for example, water, alcohols, polyols, glycerol, vegetable oils, bile acids, lecithin etc.

Excipients suitable for suppositories are, for example, natural or hardened oils, waxes, fats, semiliquid or liquid polyols etc.

The pharmaceutical products may in addition comprise preservatives, solubilizers, viscosity-increasing substances, stabilizers, wetting agents, emulsifiers, sweeteners, colorants, aromatizers, salts to alter the osmotic pressure, buffers, coating agents or antioxidants. They may also comprise other substances of therapeutic value.

The present invention further provides the use of the compounds of the formula (I), or preferably of the formula (IA), and their pharmaceutically acceptable salts in the treatment or prevention of high blood pressure, heart failure, glaucoma, myocardial infarction, renal failure and restenoses.

The compounds of the formula (I), and preferably of the formula (IA), and their pharmaceutically acceptable salts can also be administered in combination with one or more agents having cardiovascular activity, e.g. α- and β-blockers such as phentolamine, phenoxy-benzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexiline, verapamil, gallopamil, nifedipine etc.; ACE inhibitors such as cilazapril, captopril, enalapril, lisinopril etc.; potassium activators such as pinacidil; antiserotoninergics such as ketanserine; thromboxane synthetase inhibitors; neutral endopeptidase inhibitors (NEP inhibitors); angiotensin II antagonists; and diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyldopa, clonidine, guanabenz, reserpine; and other agents suitable for the treatment of high blood pressure, heart failure or vascular disorders associated with diabetes or renal disorders such as acute or chronic renal failure in humans and animals. Such combinations can be used separately or in products which comprise a plurality of components.

Further substances which can be used in combination with the compounds of the formulae (I) or (IA) are the compounds of classes (i) to (ix) on page 1 of WO 02/40007 (and the preferences and examples detailed further therein) and the substances mentioned on pages 20 and 21 of WO 03/027091.

The dosage may vary within wide limits and must of course be adapted to the individual circumstances in each individual case. In general, a daily dose appropriate for oral administration ought to be from about 3 mg to about 3 g, preferably about 10 mg to about 1 g, e.g. approximately 300 mg per adult person (70 kg), divided into preferably 1-3 single doses, which may be for example of equal size, although the stated upper limit may also be exceeded if this proves to be indicated, and children usually receive a reduced dose appropriate for their age and body weight.

EXAMPLES

The following examples illustrate the present invention. All temperatures are stated in degrees Celsius and pressures in mbar. Unless mentioned otherwise, the reactions take place at room temperature. The abbreviation "Rf=xx (A)" means for example that the Rf is found in solvent system A to be xx. The ratio of amounts of solvents to one another is always stated in parts by volume. Chemical names for final products and intermediates have been generated on the basis of the chemical structural formulae with the aid of the AutoNom 2000 (Automatic Nomenclature) program. Unless mentioned otherwise, the absolute stereochemistry of the "main chain substituents" is (2S, 4S, 5S, 7S) (see formula II).

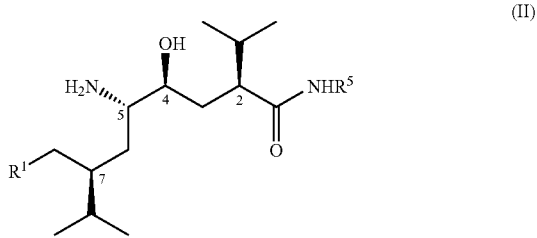

HPLC gradients on Hypersil BDS C-18 (5 um); column: 4×125 mm

I 90% water*/10% acetonitrile* to 0% water*/100% acetonitrile* in 5 minutes+2.5 minutes (1.5 ml/min)

II 95% water*/5% acetonitrile* to 0% water*/100% acetonitrile* in 40 minutes (0.8 ml/min)

* contains 0.1% trifluoroacetic acid

The following abbreviations are used:

B.p. boiling point (temperature)

M.p. melting point (temperature)

Rf ratio of distance migrated by a substance to the distance of the solvent front from the starting point in thin-layer chromatography Rt retention time of a substance in HPLC (in minutes)

General Method A: (Boc Protection of Alcohol)

0.1 mmol of 4-dimethylaminopyridine and 1.2 mmol of di-tert-butyl dicarbonate are added to a solution of 1 mmol of "alcohol" in 22 ml of dichloromethane at room temperature. The reaction mixture is stirred at room temperature for 2 hours. The reaction mixture is poured into 1M sodium bicarbonate solution and then the organic phase is separated off. The aqueous phase is extracted again with dichloromethane (2×)—the combined organic phases are washed with brine, dried with sodium sulphate and evaporated. The title compound is obtained from the residue by flash chromatography ($SiO_2$ 60 F).

General Method B: (Lactone Amidation)

A mixture of 1 mmol of "lactone", "amine" (5-30 equiv.) (methylamine/ethylamine were employed as 10% strength solution in triethylamine) and 1 mmol of 2-hydroxypyridine is stirred at 40-55° C. for 2-72 hours. The reaction mixture is mixed with 30 ml of 1M sodium bicarbonate solution and extracted with tert-butyl methyl ether (2×). The combined organic phases are dried with sodium sulphate and filtered, and the filtrate is evaporated. The title compound is obtained from the residue by flash chromatography ($SiO_2$ 60 F).

General Method C: (Hydrogenation I)

A solution of 1 mmol of "substrate" in 10-20 ml of ethyl acetate is hydrogenated in the presence of 200-400 mg of Pd/C 10% (moist) at room temperature for 1-20 hours. The reaction mixture is clarified by filtration, and the catalyst is washed with ethyl acetate. The filtrate is evaporated. The title compound is obtained from the residue by flash chromatography ($SiO_2$ 60 F).

General Method D: (Boc Protection of Amine)

2 mmol of N,N-diisopropylethylamine and 2 mmol of di-tert-butyl dicarbonate are successively added to a solution of 1 mmol of "amine" in 22 ml of dichloromethane at 0° C. The reaction mixture is warmed to room temperature and stirred at room temperature overnight. The reaction mixture is poured into water and then the organic phase is separated off. The aqueous phase is again extracted with dichloromethane (2×)—the combined organic phases are washed with brine, dried with sodium sulphate and evaporated. The title compound is obtained from the residue by flash chromatography ($SiO_2$ 60 F).

General Method E: (Boc Deprotection of Amine)

50 mmol of trifluoroacetic acid are added to a solution of 1 mmol of "amine" in 20 ml of dichloromethane at 0° C. The reaction mixture is stirred at 0° C. for 1-3 hours. The reaction mixture is neutralized with 1M sodium bicarbonate solution, and the aqueous phase is extracted with tert-butyl methyl ether (3×)—the combined organic phases are washed with brine, dried with sodium sulphate and evaporated. The title compound is obtained from the residue by flash chromatography ($SiO_2$ 60 F).

General Method F: (Hydrogenation II)

A solution of 1 mmol of "substrate" in 25 ml of ethanol and ethanolamine (1 mmol) is hydrogenated in the presence of 600 mg of Pd/C 10% (dry) at room temperature for 2-5 hours. The reaction mixture is clarified by filtration, and the catalyst is washed with ethanol. The filtrate is evaporated. The residue is treated with 1M sodium bicarbonate solution and extracted with tert-butyl methyl ether (3×)—the combined organic phases are dried with sodium sulphate and evaporated. The title compound is obtained from the residue by flash chromatography ($SiO_2$ 60 F).

General Method G: (Alcohol Methoxyacetylation)

2.6 mmol of pyridine, 2.4 mmol of methoxyacetyl chloride and 0.1 mmol of 4-dimethylamino-pyridine are successively added to a solution of 1 mmol of "alcohol" in 13.5 ml of toluene at 0° C. The ice bath is removed and the reaction mixture is stirred at room temperature for 2 hours. The reaction mixture is poured into 0.5M HCl and then the organic phase is separated off. The aqueous phase is extracted again with diethyl ether (3×)—the combined organic phases are washed with brine, dried with sodium sulphate and evaporated. The title compound is obtained from the residue by flash chromatography ($SiO_2$ 60 F).

General Method H: (Grignard Reaction)

A solution of 1 mmol of dibutylmagnesium (1M in heptane) in 3.6 ml of tetrahydrofuran is cooled to 0° C., and 1 mmol of butyllithium solution (1.6M in hexane) is added dropwise at 0° C. The mixture is stirred at 0° C. for 10 minutes. A solution of 1 mmol of "aryl bromide" or "heteroaryl bromide" in 1.4 ml of tetrahydrofuran is added dropwise at 0° C. The reaction mixture is stirred at 0° C. for 15 minutes, then cooled to −78° C., and a solution of 1 mmol of 2-[2-azido-2-(4-isopropyl-5-oxotetrahydrofuran-2-yl)ethyl]-3-methylbutyraldehyde [173154-02-4] in 1.4 ml of tetrahydrofuran is added dropwise at −78° C. The reaction mixture is stirred at −78° C. for 1 hour and quenched with 1M ammonium chloride solution. It is extracted with tert-butyl methyl ether (3×). The combined organic phases are washed with brine, dried with sodium sulphate and evaporated. The title compound is obtained from the residue by flash chromatography ($SiO_2$ 60 F).

General method I: (Heteroaryl Lithium Addition Onto Aldehyde)

A solution of 1 mmol of "aryl bromide" or "heteroaryl bromide" in 2.70 ml of tetrahydrofuran is cooled to −100° C., and 1 mmol of butyllithium solution (1.6M in hexane) is added at −100° C. The reaction mixture is stirred at −100° C. for 1 minute and rapidly added to a solution of 1 mmol of 2-[2-azido-2-(4-isopropyl-5-oxotetrahydrofuran-2-yl)ethyl]-3-methylbutyraldehyde [173154-02-4] in 1 ml of tetrahydrofuran at −100° C. The reaction mixture is stirred at −100° C. for 15 minutes and quenched with 1M ammonium chloride solution. It is extracted with tert-butyl methyl ether (3×). The combined organic phases are washed with brine, dried with sodium sulphate and evaporated. The title compound is obtained from the residue by flash chromatography (SiO$_2$ 60 F).

Building blocks R$^1$:

1
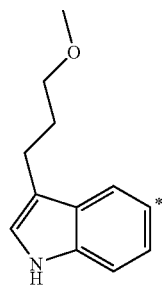

2
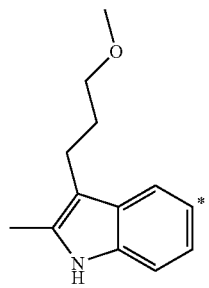

3
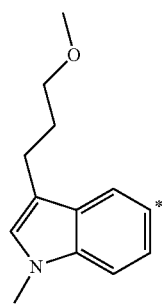

4
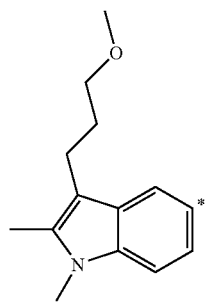

5
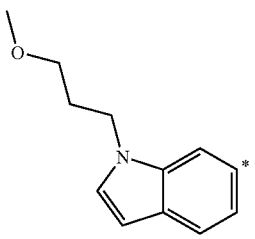

6
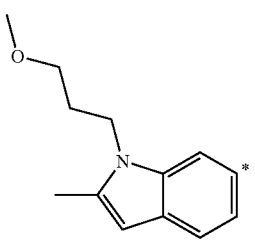

7
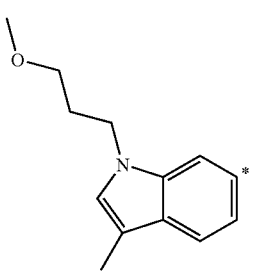

8
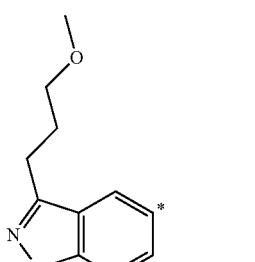

9
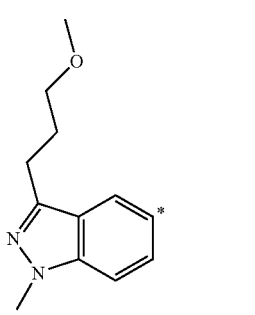

10
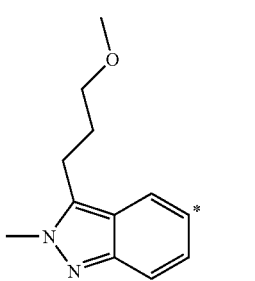

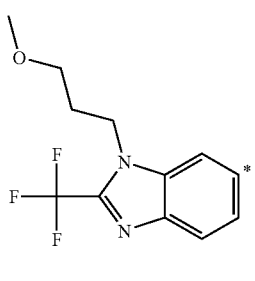
11
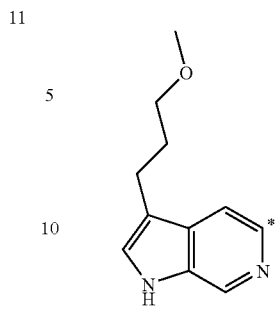
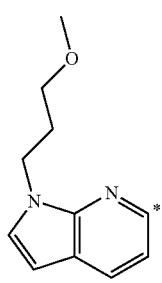
14
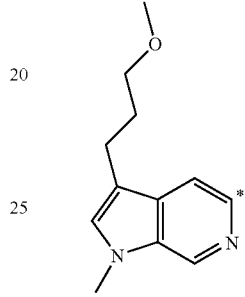
15
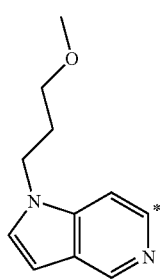
15
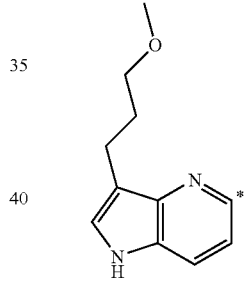
16
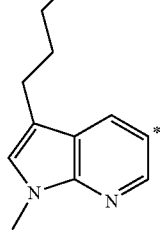
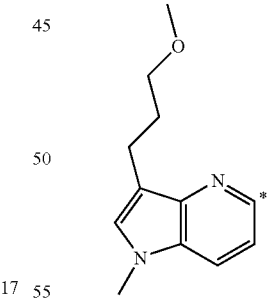
17
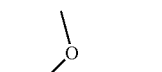
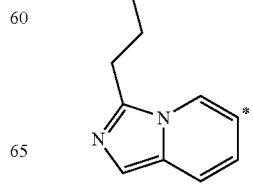

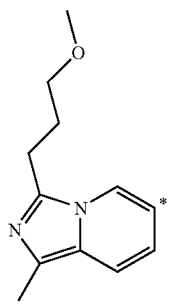
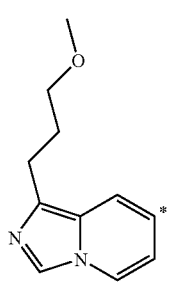
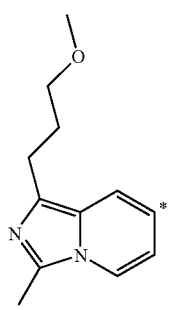
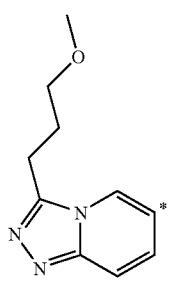
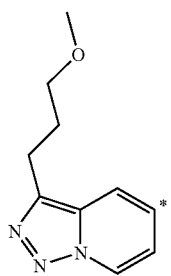
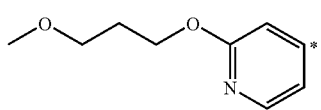
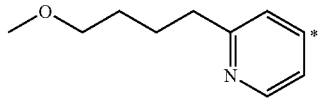
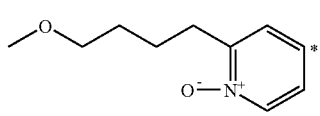
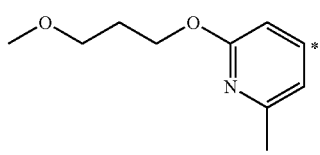
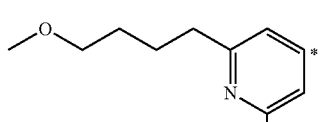
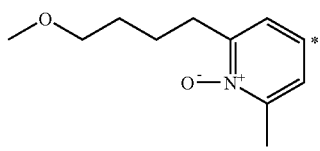
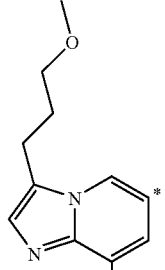
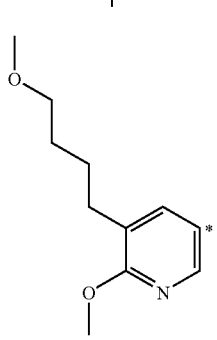
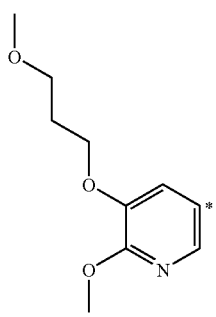

38 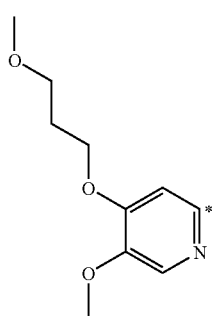
39 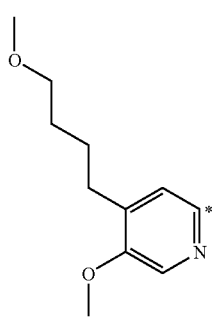
40 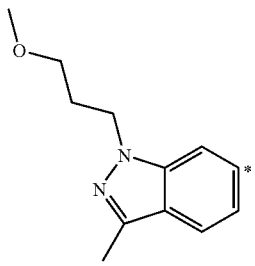
42 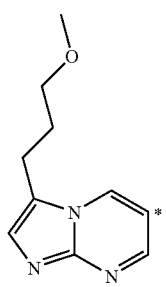
44 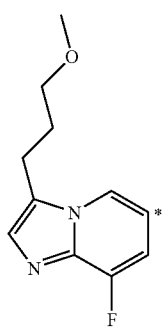
45 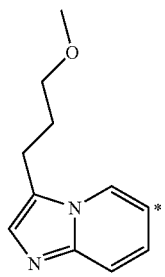
46 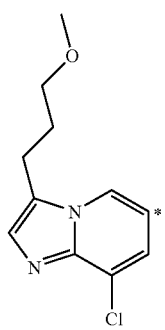
47 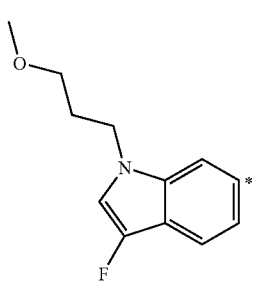
48 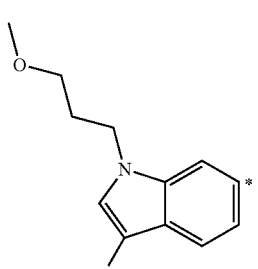
49 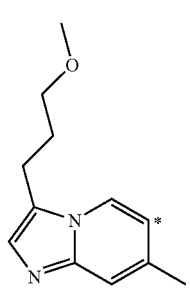

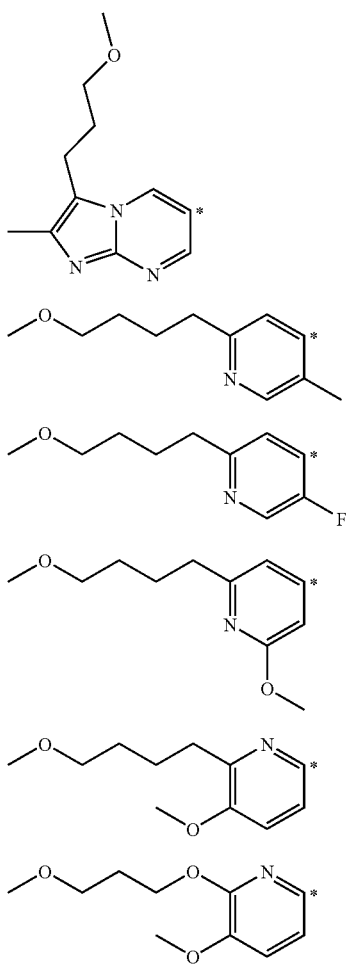

Preparations of the R1 building blocks R1 (1-40), (bromine or iodine derivatives) are described on pages 20-39 of WO 2005/090305, which are incorporated herein, and take place, unless mentioned otherwise, in accordance with the syntheses described therein.

The $R^1$ building blocks (bromine or iodine derivatives) protected where appropriate are prepared as follows:

25 7-Bromo-1-(3-methoxyoropyl)-3-methylimidazo[1,5-a]pyridine

A solution of 12.0 g of N-[1-(4-bromopyridin-2-yl)-4-methoxybutyl]acetamide in 150 ml of benzene is mixed with 9.51 ml of phosphorus oxychloride. The reaction solution is stirred at 50° C. for 3 hours and then diluted with ethyl acetate. It is basified with 1M sodium hydroxide solution, and the phases are separated. The aqueous phase is extracted with ethyl acetate (2×). The combined organic phases are evaporated. The title compound is obtained as a brownish oil from the residue by flash chromatography (SiO$_2$ 60 F). Rf=0.39 (EtOAc-methanol 9:1); Rt=2.76 (Gradient I).

The starting materials are prepared as follows:

a) N-[1-(4-Bromopyridin-2-yl)-4-methoxybutyl]acetamide

A solution of 32.0 g of 1-(4-bromopyridin-2-yl)-4-methoxybutylamine in 150 ml of glacial acetic acid is mixed with 37 ml of acetic anhydride. The reaction solution is stirred at 50° C. for 30 minutes and then diluted with ethyl acetate. It is basified with 2M sodium hydroxide solution, and the phases are separated. The aqueous phase is extracted with ethyl acetate (2×). The combined organic phases are evaporated. The title compound is obtained as a yellowish solid from the residue by flash chromatography (SiO$_2$ 60 F). Rf=0.38 (EtOAc-methanol 9:1); Rt=2.33 (Gradient I).

b) 1-(4-Bromopyridin-2-yl)-4-methoxybutylamine

A solution of 4.3 g of 4-bromopyridine-2-carbonitrile [62150-45-2] in 10 ml of tetrahydrofuran is added to a solution of 8.79 g of 3-methoxypropylmagnesium chloride [14202-12-1] in 10 ml of tetrahydrofuran. The reaction solution is stirred at room temperature for 10 minutes and then 50 ml of methanol are added. 2.7 g of sodium borohydride are added to the solution over the course of 30 minutes, and the mixture is stirred at room temperature for 2.5 hours. It is diluted with ethyl acetate and basified with 1M sodium hydroxide solution. The phases are separated. The aqueous phase is extracted with ethyl acetate (2×). The combined organic phases are evaporated. The crude title compound is obtained as an orange oil from the residue. Rt=2.47 (Gradient I).

36 5-Bromo-2-methoxy-3-(4-methoxybutyl)pyridine 28 g of 5-bromo-2-methoxy-3-(4-methoxybut-1(E,Z)-enyl)pyridine are added to a suspension of 24.86 g of Raney nickel in 200 ml of ethanol and 200 ml of tetrahydrofuran. The reaction mixture is then hydrogenated under atmospheric pressure at room temperature for 2 hours. The catalyst is filtered off through Hyflo, the filter cake is washed with methanol (2×), and the filtrate is concentrated. The title compound is obtained as a colourless oil from the residue by flash chromatography (SiO$_2$ 60 F). Rt=5.17 (Gradient I).

The starting material is prepared as follows:

a) 5-Bromo-2-methoxy-3-(4-methoxybut-1(E,Z)-enyl)pyridine n-Butyllithium (120 ml, 1.6M in hexane) is added to a suspension of 80.74 g of (3-methoxy-propyl)triphenylphosphonium bromide [111088-69-8] in 250 ml of tetrahydrofuran under an argon atmosphere at 0° C. The reaction mixture is stirred at 0° C. for 50 minutes and then 28 g of 5-bromo-2-methoxypyridine-3-carbaldehyde [103058-87-3] are added. The reaction mixture is stirred at 0° C. for 1 hour and then at room temperature for 1 hour and diluted with tert-butyl methyl ether. The solution is washed with 1M sodium bicarbonate solution. The organic phase is dried over sodium sulphate and evaporated. The title compound is obtained as a yellowish oil from the residue by flash chromatography (SiO$_2$ 60 F). Rt=5.03 (Gradient I)

37
5-Bromo-2-methoxy-3-(3-methoxypropoxy)pyridine

A mixture of 113.26 mmol of 5-bromo-3-(3-methoxypropoxy)-1H-pyridin-2-one, 79.28 mmol of silver carbonate and 158.56 mmol of iodomethane in 230 ml of benzene is stirred at 45° C. with exclusion of light for 24 hours. The reaction mixture is cooled to room temperature, and the silver salts are filtered off. The filtrate is washed with 2% sodium bicarbonate solution and water (2×). The organic phase is dried over sodium sulphate and evaporated. The crude title compound is obtained as a beige oil from the residue and is employed without further purification in the next stage. Rf=0.45 (EtOAc-heptane 1:2); Rt=4.34 (Gradient I).

The starting material is prepared as follows:

a) 5-Bromo-3-(3-methoxypropoxy)-1H-pyridin-2-one 350 ml of N,N-dimethylformamide and 358.11 mmol of 5-bromo-3-hydroxy-1H-pyridin-2-one [34206-49-0] are added to 1400 ml of a 1.4M NaOH solution. The mixture is stirred for 45 minutes, and 447.64 mmol of bis(3-methoxypropyl) sulphate are cautiously added. The mixture is stirred at room temperature for 20 hours and then diluted with water. It is extracted with dichloromethane (3×). The combined organic phases are dried over sodium sulphate and evaporated. The title compound is obtained as a yellowish oil from the residue by flash chromatography (SiO$_2$ 60 F). Rf=0.42 (dichloromethane-methanol-conc. ammonia 25% 200:20:1); Rt=2.68 (Gradient I).

b) Bis(3-methoxypropyl) sulphate

A solution of 726.22 mmol of bis(3-methoxypropyl) sulphite in 330 ml of tetrachloromethane, 330 ml of acetonitrile and 830 ml of water is cooled to 15° C., and 18.16 mmol of ruthenium(III) chloride hydrate are added. 1089.34 mmol of sodium periodate are added in small portions, and the reaction mixture is stirred at room temperature overnight. It is diluted with ethyl acetate, and the organic phase is separated off, dried with sodium sulphate and evaporated. The crude title compound is obtained as a beige liquid from the residue and is employed without further purification in the next stage.

c) Bis(3-methoxypropyl) sulphite

A solution of 2225.9 mmol of 3-methoxypropanol in 2 l of dichloromethane is mixed with 4897.0 mmol of triethylamine and cooled to −10° C. 1112.9 mmol of thionyl chloride are added dropwise at −10 −5° C. over the course of 40 minutes. The yellow suspension is stirred at room temperature for 19 hours and then ice-water is added. It is extracted with dichloromethane, and the organic phase is washed with brine, dried with sodium sulphate and evaporated. The crude title compound is obtained as a brownish oil from the residue and is employed without further purification in the next stage.

The following building blocks are prepared in an analogous manner to the process described in WO 2005/090305 for building blocks 1, 5, 9, 11, 32 and 35:
42  6-Bromo-3-(3-methoxypropyl)imidazo[1,2-a]pyrimidine
44  6-Bromo-8-fluoro-3-(3-methoxypropyl)imidazo[1,2-a]pyridine
45 6-Bromo-3(3-methoxypropyl)imidazo[1,2-a]pyridine
46  6-Bromo-8-chloro-3-(3-methoxypropyl)imidazo[1,2-a]pyridine
49  6-Bromo-3-(3-methoxypropyl)-7-methylimidazo[1,2-a]pyridine
51 4-Bromo-2-(4-methoxybutyl)-5-methylpyridine
53 4-Bromo-2-methoxy-6-(4-methoxybutyl)pyridine 6-Bromo-3-fluoro-1-(3-methoxypropyl)-1H-indole A solution of 1.5 mmol of 3,6-dibromo-1-(3-methoxypropyl)-1H-indole in 70 ml of THF is cooled to −78° C., and 1.5 mmol of tert-butyllithium are added. The mixture is stirred at −78° C. for 15 minutes and then quenched with 1.5 mmol of N-fluorodibenzenesulphonamide. The reaction solution is warmed to room temperature. Saturated ammonium chloride solution and ethyl acetate are added, the phases are separated, and the aqueous phase is extracted with ethyl acetate (3×).

The combined organic phases are dried over sodium sulphate and evaporated. The title compound is identified by means of the Rf from the residue by flash chromatography (SiO$_2$ 60 F).

a) 3,6-Dibromo-1-(3-methoxypropyl)-1H-indole

A solution of 10.39 g of 6-bromo-1-(3-methoxypropyl)-1H-indole (building block 5) in 1.5 l of tetrahydrofuran is cooled to −78° C., and 7.05 g of N-bromosuccinimide are added. The mixture is stirred at −78° C. for 1.7 hours and then warmed to room temperature. The reaction mixture is evaporated. The title compound is obtained as an orange oil from the residue by flash chromatography (SiO$_2$ 60 F). Rf=0.31 (EtOAc-heptane 1:4); Rt=5.65 (Gradient I).

48 6-Bromo-1-(3-methoxypropyl)-1H-indole-3-carbonitrile

Compounds which comprise building block 48 are obtained from precursors for those compounds which comprise building block 5. Reaction to give the 3-cyanoindole derivative is carried out in analogy to Example 48H in 2 stages via the primary amide before the last stage of the synthesis to give the final compound.

50 6-Bromo-3-(3-methoxypropyl)-2-methylimidazo[1,2-a]pyrimidine 0.85 mmol of 5-bromopyrimidin-2-ylamine [7752-82-1] and 1.7 mmol of 3-chloro-6-methoxyhexan-2-one are reacted in analogy to building block 35. The title compound is identified by means of the Rf.

The starting material is prepared as follows:

a) 3-Chloro-6-methoxyhexan-2-one 1.5 mol of 6-methoxyhexan-2-one [29006-00-6] are added to a mixture of 3.6 mol of copper(II) chloride hydrate and 1.8 mol of lithium chloride in 900 ml of N,N-dimethylformamide at 80° C. The reaction mixture is stirred at 80-90° C. for 1 hour. 900 g of ice are added, and the precipitate is dissolved by adding N,N-dimethylformamide. Extraction with pentane (6×) is carried out. The combined organic phases are washed with water, dried over sodium sulphate and fractionated in vacuo. The title compound is identified by means of the Rf.

52 4-Bromo-5-fluoro-2-(4-methoxybutyl)pyridine 0.85 g of 2,4-dibromo-5-fluoropyridine is reacted in analogy to building block 32. The title compound is identified by means of the Rf.

The starting material is prepared as follows:

a) 2,4-Dibromo-5-fluoropyridine

A solution of 8 mmol of 5-fluoro-2,4-dihydroxypyridine [41935-70-0] in 36.5 mmol phosphorus oxybromide is heated at 140° C. in a closed Supelco bottle for 4 hours. The reaction mixture is poured onto ice, and the aqueous phase is adjusted to pH 9 with 1M sodium bicarbonate solution. The aqueous phase is extracted with tert-butyl methyl ether (3×). The combined organic phases are washed with brine, dried over sodium sulphate and evaporated. The title compound is identified from the residue by means of the Rf by flash chromatography (SiO$_2$ 60 F).

54 6-Bromo-3-methoxy-2(4-methoxybutyl)pyridine 1.2 mmol of 2,4-dibromo-5-fluoropyridine are reacted in analogy to building block 32a. The title compound is identified by means of the Rf.

The starting material is prepared as follows:

a) 6-Bromo-3-methoxy-2-(4-methoxybut-1-enyl) pyridine 1.5 mmol of 6-bromo-3-methoxypyridine-2-carbaldehyde and (3-methoxypropyl)triphenyl-phosphonium iodide [133622-76-1] are reacted in analogy to building block 24a. The title compound is identified by means of the Rf.

b) 6-Bromo-3-methoxypyridine-2-carbaldehyde 44 mmol of sodium borohydride are added in portions to a solution of 2.2 mmol of methyl 6-bromo-3-methoxypyridine-2-carboxylate in 750 ml of methanol. The mixture is stirred at room temperature for 2 days. Water is added to the reaction mixture, and it is extracted with dichloromethane (3×). The combined organic phases are dried with sodium sulphate and concentrated. The solid resulting after addition of n-hexane is filtered off with suction and dried.

3.3 mmol of oxalyl chloride are added to a solution of 1 ml of dimethyl sulphoxide in 10 ml of dichloromethane at −60° C. The mixture is stirred at −60° C. until the evolution of gas subsides. A solution of the solid in 10 ml of dichloromethane is added dropwise at −60° C. The reaction mixture is stirred at −30° C. for 30 minutes, again cooled to −60° C., and 8.8 mmol of triethyl-amine are added. The mixture is stirred at room temperature for 30 minutes. Water and dichloromethane are added, the phases are separated, and the aqueous phase is extracted with dichloromethane (3×). It is evaporated, mixed with toluene, dried with sodium sulphate and evaporated. The crude title compound is identified by means of the Rf.

c) Methyl 6-bromo-3-methoxypyridine-2-carboxylate

A solution of diazomethane in diethyl ether (about 0.4 M) is added in excess to a solution of 2.3 mmol of methyl 6-bromo-3-hydroxypyridine-2-carboxylate [321601-48-3] in 30 ml of methanol at 0° C. The mixture is stirred at 0° C. for 2 hours, then quenched with magnesium sulphate, filtered and evaporated. The crude title compound is identified by means of the Rf.

55
6-Bromo-3-methoxy-2-(3-methoxypropoxy)pyridine

A solution of 1 mmol of 6-bromo-3-methoxypyridin-2-ol in 2 ml of N,N-dimethylformamide is mixed with 1.5 mmol of potassium carbonate, 1.5 mmol of tetrabutylammoniumbromide and 1.1 mmol of 1-chloro-3-methoxypropane. The reaction mixture is stirred at 100° C. for 11 hours. The reaction mixture is filtered and evaporated. The residue is partitioned between ethyl acetate and water/brine 9:1. The phases are separated, the aqueous phase is extracted with ethyl acetate (2×)—the combined organic phases are washed with brine, dried with sodium sulphate and evaporated. The title compound is identified by means of the Rf from the residue by flash chromatography (SiO₂ 60 F).

a) 6-Bromo-3-methoxypyridin-2-ol 45 ml of hydrogen peroxide (15% strength) are added dropwise to a stirred solution of 152.5 mmol of 3-methoxy-pyridin-2-ol [20928-63-6] in 152 ml of hydrobromic acid (48% strength) at 70° C. over the course of one hour so that the temperature remains at 70° C. The mixture is stirred at this temperature for a further hour. It is then cooled to room temperature, and 1M sodium thiosulphate solution is added to the reaction solution until excess bromine is completely reduced (decolorization). Saturated sodium carbonate solution is then added to the resulting solution until the pH is 4. A solid precipitates and is filtered off. Further saturated sodium carbonate solution is added to the clear filtrate until the pH reaches 11. It is extracted with dichloromethane (3×), and the combined organic phases are dried with sodium sulphate and evaporated. The title compound is identified by means of the Rf from the residue by flash chromatography (SiO₂ 60 F).

Building Blocks NHR⁵

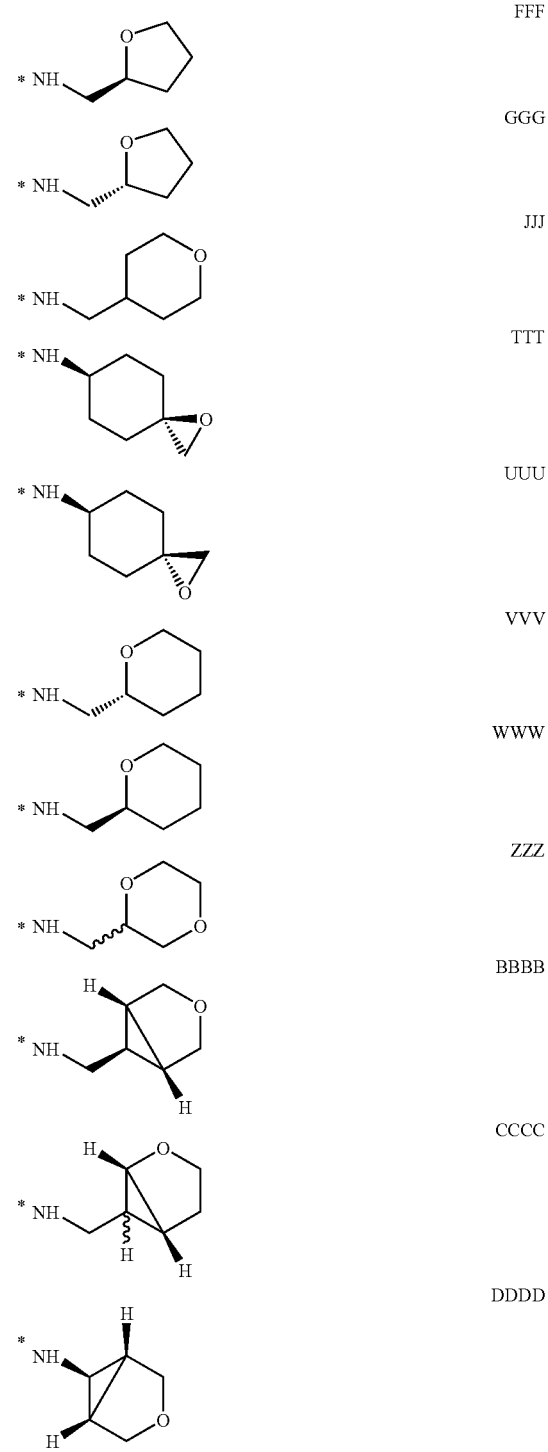

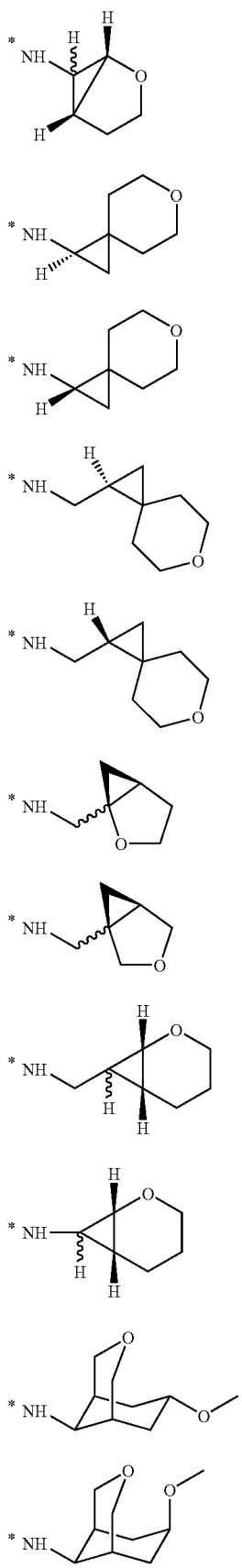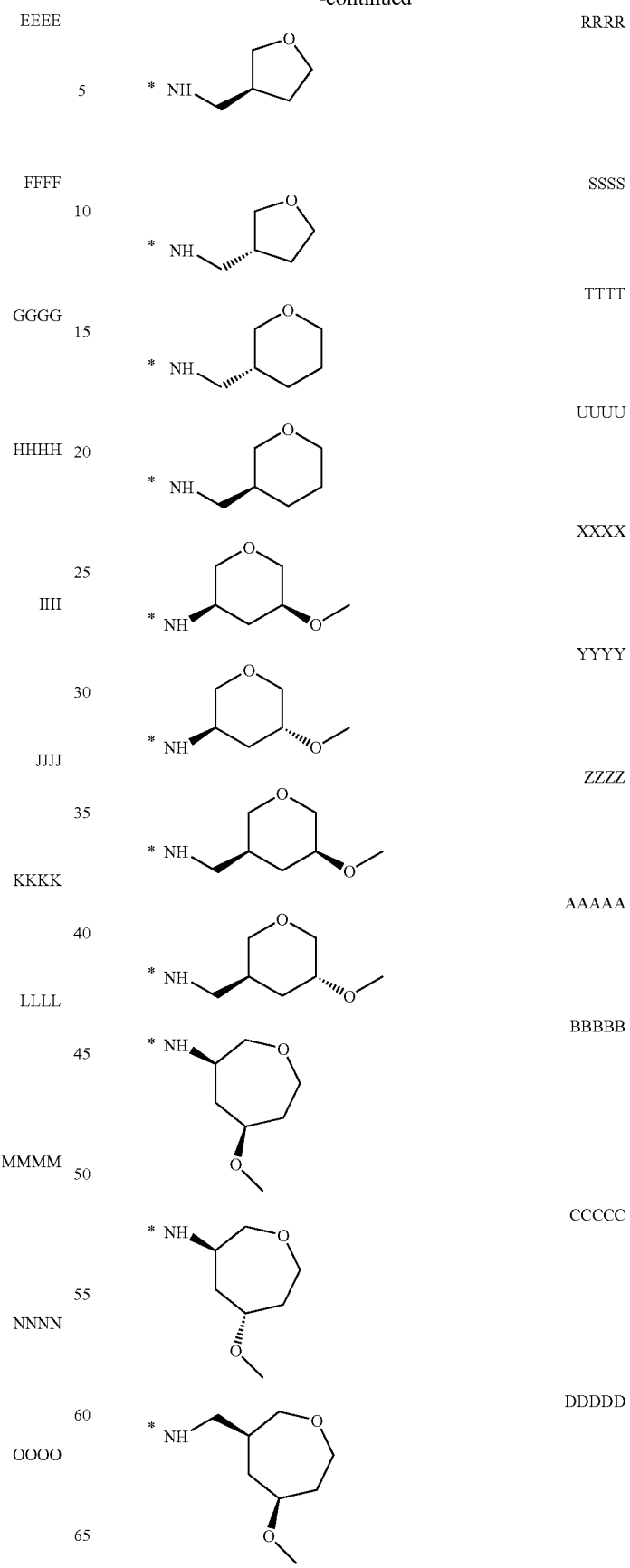

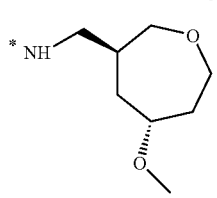 EEEEE
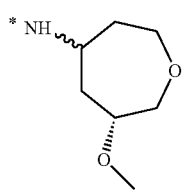 FFFFF
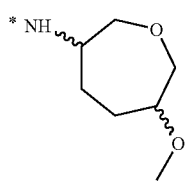 GGGGG
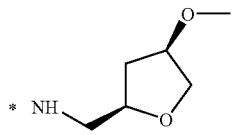 HHHHH
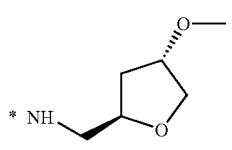 IIIII
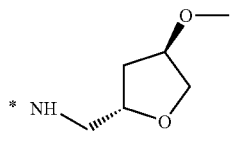 JJJJJ
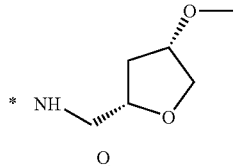 KKKKK
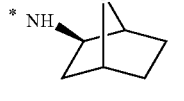 LLLLL
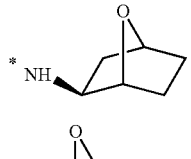 MMMMM
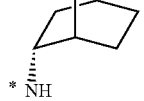 NNNNN
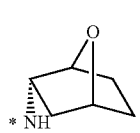 OOOOO
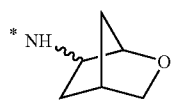 PPPPP
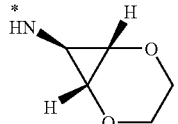 QQQQQ
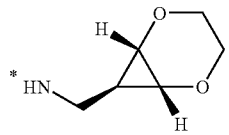 RRRRR
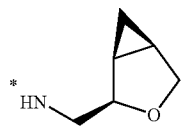 SSSSS
 TTTTT
 UUUUU
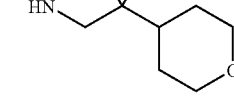 VVVVV
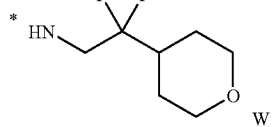 WWWWW
 XXXXX
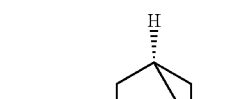 DDDDDD
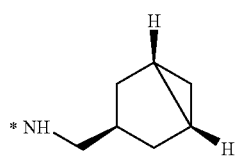 EEEEEE

FFFFF

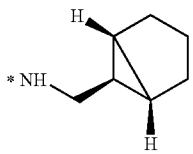

Building blocks NHR[5] whose preparation is not explicitly described are commercially available or can be prepared by methods known from the literature.

The amines R[5]NH$_2$ or their salts are prepared as follows:

TTT (cis)-1-Oxaspiro[2.5]oct-6-ylamine and UUU (trans)-1-Oxaspiro[2.5]oct-6-ylamine A solution of 3.55 mmol of benzyl (1-oxaspiro[2.5]-oct-6-yl)carbamate [142010-03-5] in 80 ml of methanol is hydrogenated in the presence of 0.13 mmol of Pd/C 10% (moist) at 0° C. for 1 hour. The reaction mixture is clarified by filtration, and the catalyst is washed with ethanol. The filtrate is evaporated. The title compounds are identified by means of the Rf from the residue by flash chromatography (SiO$_2$ 60 F).

VVV C-(Tetrahydropyran-2(R)-yl)methylamine

A solution of 2.62 mmol of 2(R)-azidomethyltetrahydropyran in 150 ml of methanol is hydrogenated in the presence of 0.03 mmol of Pd/C 10% (moist) until conversion is complete. The reaction mixture is clarified by filtration, and the catalyst is washed with ethanol. The filtrate is evaporated. The crude title compound is identified by means of the Rf from the residue.

The starting materials are prepared as follows:

a) 2(R)-Azidomethyltetrahydropyran

A solution of 5 mmol of tetrahydropyran-2(R)-yl methyl methanesulphonate and 55 mmol of sodium azide in 50 ml of dimethyl sulphoxide is stirred at room temperature for 20 hours. It is then diluted with water and tert-butyl methyl ether and washed with brine. The aqueous phase is extracted with tert-butyl methyl ether (2×). The combined organic-phases are dried with sodium sulphate and evaporated. The crude title compound is identified by means of the Rf from the residue.

b) Tetrahydropyran-2(R)-yl methyl methanesulphonate 50 mmol of triethylamine and 20 mmol of methanesulphonyl chloride are successively added to a solution of 10 mmol of (tetrahydropyran-2(R)-yl)methanol [70766-06-2] in 100 ml of dichloromethane at 0° C. The mixture is stirred at 0° C. for 1 hour, diluted with dichloromethane and washed with 1M HCl. The organic phase is dried with sodium sulphate and evaporated. The crude title compound is identified by means of the Rf from the residue.

WWW C-(Tetrahydropyran-2(S)-yl)methylamine

The title compound is prepared in analogy to building block VVV from (tetrahydropyran-2(S)-yl)methanol [51450-44-3].

BBBB (exo)-C-[1-(3-Oxabicyclo[3.1.0]hex-6-yl] methylamine 65.3 g of lithium aluminium hydride (pellets) are added in portions to a stirred mixture of 70 g of (exo)-3-oxabicyclo [3.1.0]-hexane-6-carboxamide and 1.1 l of tetrahydrofuran at 0° C. The reaction mixture is stirred at room temperature for 19 hours. The resulting mixture is cooled to 0° C. and successively 100 ml of water, 100 ml of 1M NaOH and 300 ml of water are added dropwise. The resulting suspension is clarified by filtration through Hyflo, and the filtrate is evaporated. The title compound is obtained as a colourless liquid from the residue by distillation. B.p. 65-75° C. under 15 mbar.

The starting material is prepared as follows:

a) (exo)-3-Oxabicyclo[3.1.0]hexane-6-carboxamide

A mixture of 95.0 g ethyl (exo)-3-oxabicyclo[3.1.0]-hexane-6-carboxylate [81056-11-3] and 500 ml of aqueous 30% strength ammonia solution is stirred at room temperature for 3 days. The resulting emulsion is evaporated to dryness, and the residue is dried in vacuo. The crude title compound is obtained as a brown solid.

CCCC C-(2(exo,endo)-Oxabicyclo[3.1.0]hex-6-yl)-methylamine

The title compound is prepared in analogy to building block BBBB from (exo,endo)-2-oxabicyclo[3.1.0]-hexane-6-carboxamide [89598-52-7].

Alternatively, the title compound can be prepared in analogy to building block VVV from ((exo,endo)-2-oxabicyclo [3.1.0]-hex-6-yl)methanol.

The starting material is prepared as follows:

a) ((exo,endo)-2-Oxabicyclo[3.1.0]hex-6-yl)methanol

A solution of 1.89 mmol of ethyl (exo,endo)-2-oxabicyclo [3.1.0]-hexane-6-carboxylate [202334-19-8], [213137-33-8] in 2 ml of tetrahydrofuran is added dropwise to a suspension of 3.68 mmol of lithium aluminium hydride in 4.5 ml of tetrahydrofuran at −10° C. The reaction mixture is stirred at 0° C. for 30 minutes. Then successively 144 µl of water, 144 µl of 5M NaOH and 432 µl of water are cautiously added, and the mixture is stirred at room temperature for 25 minutes. The reaction mixture is filtered through Hyflo and evaporated. The title compound is identified by means of the Rf from the residue by flash chromatography (SiO$_2$ 60 F).

DDDD (exo)-(3-Oxabicyclo[3.1.0]hex-6-yl)amine

A mixture of 7.0 g of tert-butyl (exo)-(3-oxabicyclo[3.1.0]-hex-6-yl)carbamate and 52 ml of 4M HCl (in dioxane) is stirred at 0° C. for 1 hour and then at room temperature for 2 hours. The resulting suspension is cooled in an ice bath and, after addition of 200 ml of tert-butyl methyl ether, the solid ((exo)-(3-oxabicyclo[3.1.0]-hex-6-yl)amine hydrochloride) is filtered off with suction.

The hydrochloride is added to a stirred mixture of 40 ml of 50% strength sodium hydroxide solution and 75 ml of tert-butyl methyl ether. The organic phase is separated off, dried with sodium hydroxide (solid), evaporated and distilled at 100 mbar/40° C. The title compound is obtained as a pale yellowish liquid.

The starting material is prepared as follows:

a) tert-Butyl (exo)-(3-oxabicyclo[3.1.0]hex-6-yl)carbamate

A solution of 50.2 g of (exo)-3-oxabicyclo[3.1.0]-hexane-6-carboxylic acid [CAS55780-88-6] and 450 ml of tert-butanol is heated to 30° C. Then, over the course of 30 minutes, 58.7 ml of triethylamine and 91.4 ml of diphenylphosphoryl azide are added dropwise in parallel. The reaction mixture is stirred at 70° C. for 18 hours. The resulting mixture is evaporated, and the residue is mixed with 1 l of 1M HCl and extracted with ethyl acetate (3×). The organic phases are washed with water (1×), 1M sodium bicarbonate solution and brine (1×), dried with sodium sulphate and filtered, and the filtrate is evaporated. The title compound is obtained in the form of white crystals from the residue by flash chromatography and crystallization from heptane. Rf=0.33 (EtOAc-heptane 1:1); M.p. 86-87° C.

EEEE (exo,endo)-2-Oxabicyclo[3.1.0]hex-6-ylamine

The starting material is prepared in analogy to building block DDDD from (exo,endo)-2-oxabicyclo[3.1.0]-hexane-6-carboxylic acid [99418-15-2].

FFFF (R)-(6-Oxaspiro[2.5]oct-1-yl)amine

A solution of 0.528 g of (R)-6-oxaspiro[2.5]-octane-1-carboxylic acid in 5 ml of tetrahydrofuran is mixed with 1.20 ml of triethylamine, and the solution is then cooled to 0° C. The solution is mixed with 0.657 ml of ethyl chloroformate, and the reaction mixture is stirred at 0° C. for 1 hour. A solution of 4.44 g of sodium azide in 5 ml of water is added and the reaction mixture is stirred at 0° C. for a further hour. The reaction mixture is diluted with water and extracted with tert-butyl methyl ether. The combined extracts are washed with brine, dried with sodium sulphate and evaporated. The residue is taken up in 5 ml of benzene, and the solution is heated to reflux for 2 hours and then evaporated. The residue is dissolved in 5 ml of tetrahydrofuran, and 5 ml of water and 0.347 g of lithium hydroxide are added. The reaction mixture is stirred at room temperature for 3 hours and then adjusted to pH 2 with 4M HCl. The tetrahydrofuran is distilled off, and the aqueous residue is adjusted to pH 12 with 2M NaOH. The aqueous phase is extracted with dichloromethane, and the combined organic extracts are dried over sodium sulphate and evaporated. The title compound is obtained as a yellow oil which is employed without further purification in the next stage. Rf=0.26 (dichloro-methane-methanol-conc. ammonia 25% 200:20:1).

The starting materials are prepared as follows:

a) (R)-6-Oxaspiro[2.5]octane-1-carboxylic acid

A solution of 3.700 g of (R)-4-benzyl-3-((R)-6-oxaspiro [2.5]-octane-1-carbonyl)oxazolidin-2-one in 20 ml of tetrahydrofuran/water 3:1 is cooled to 0° C. 0.608 g of lithium hydroxide and 1.95 ml of hydrogen peroxide (30% in water) are added to the solution, which is stirred at room temperature for 6 hours. Saturated aqueous sodium thiosulphate solution is added to the reaction mixture, which is then extracted with tert-butyl methyl ether. The aqueous phase is adjusted to pH 2 with 4M HCl and extracted with dichloromethane. The combined extracts are washed with brine, dried with sodium sulphate and evaporated. The title compound is obtained as a colourless liquid and is employed without further purification for the next stage. Rf=0.55 (dichloromethane-methanol-water-acetic acid 150:54:10:1); Rt=2.10 (Gradient I).

b) (R)-4-Benzyl-3-((R)-6-oxaspiro[2.5]octane-1-carbonyl)oxazolidin-2-one and (R)-4-Benzyl-3-((S)-6-oxaspiro[2.5]octane-1-carbonyl)oxazolidin-2-one A solution of 118.81 g of (R)-4-benzyloxazolidin-2-one [102029-44-7] in 90 ml of anhydrous tetrahydrofuran is cooled to −75° C. under argon. A solution of n-butyllithium (1.6M in hexane) is added at −75°-60° C. over the course of 2 hours. The reaction mixture is stirred at −75° C. for 10 minutes, and a solution of 110.37 g of 6-oxaspiro[2.5]-octane-1-carbonyl chloride in 100 ml of tetrahydrofuran is added dropwise at −75°--60° C. The reaction mixture is then slowly warmed to 20° C. and saturated aqueous ammonium chloride solution is added. The mixture is extracted with tert-butyl methyl ether, and the combined extracts are washed with brine, dried with sodium sulphate and evaporated. The title compounds are obtained as white solids from the residue by column chromatography (SiO$_2$ 60 F), Rf (diastereomer 1)=0.25 (EtOAc-heptane 1:2); Rt (diastereomer 1)=4.20 (Gradient I); Rf (diastereomer 2)=0.21 (EtOAc-heptane 1:2); Rt (diastereomer 2)=4.27 (Gradient I).

c) 6-Oxaspiro[2.5]octane-1-carbonyl chloride 60.0 ml of oxalyl chloride are added to a solution of 98.73 g of 6-oxaspiro[2.5]-octane-1-carboxylic acid in 500 ml of dichloromethane at 0° C. One drop of N,N-dimethylformamide is added, and the reaction solution is stirred at room temperature for 1 hour. The reaction solution is then evaporated, and the crude product is employed directly for the next stage.

d) 6-Oxaspiro[2.5]octane-1-carboxylic acid

A solution of 120.50 g of ethyl 6-oxaspiro[2.5]-octane-1-carboxylate in 700 ml of ethanol/water 3.5:1 is mixed with 55.20 g of potassium hydroxide. The reaction mixture is heated at 60° C. for 4 hours, the ethanol is distilled off and the aqueous residue is diluted with water and extracted with tert-butyl methyl ether. The aqueous phase is adjusted to pH 2 with 4M hydrochloric acid and extracted with tert-butyl methyl ether. The combined organic extracts are washed with brine, dried with sodium sulphate and evaporated. The title compound is obtained as a yellowish oil and is employed without further purification for the next stage. Rt=2.13 (Gradient I).

e) Ethyl 6-oxaspiro[2.5]octane-1-carboxylate 51.93 g of sodium hydride (60% dispersion in oil) is taken up in 1100 ml of dry dimethyl sulphoxide under argon. 272 g of trimethylsulphoxonium iodide are added in portions over 20 minutes at room temperature, and the reaction mixture is then stirred at room temperature for 1.5 hours. 170.00 g of ethyl (tetrahydropyran-4-ylidene)acetate [130312-00-4] are added dropwise, and the reaction mixture is stirred at room temperature for 18 hours. The mixture is poured into ice and extracted with tert-butyl methyl ether. The combined organic extracts are washed with brine, dried with sodium sulphate and evaporated. The title compound is obtained as a colourless oil from the residue by vacuum distillation (68-70° C., 0.09 mbar). Rt=3.49 (Gradient I).

GGGG (S)—(6-Oxaspiro[2.5]oct-1-yl)amine

The title compound is prepared in analogy to building block FFFF and FFFFa from (R)-4-benzyl-3-((S)-6-oxaspiro [2.5]-octane-1-carbonyl)oxazolidin-2-one (building block FFFFb).

HHHH C—[(S)-1-(6-Oxaspiro[2.5]oct-1-yl)]methylamine 10.60 g of lithium aluminium hydride is taken up in 160 ml of dry tetrahydrofuran under argon. The suspension is cooled to 0° C., and a solution of 10.75 g of (S)-6-oxaspiro[2.5]-octane-1-carboxamide in 60 ml of tetrahydrofuran is added dropwise. The reaction mixture is stirred at 0° C. for 4 hours and then 7.80 ml of water, followed by 34 ml of 3M NaOH and 30 ml of water, are added. The solid is filtered off through Hyflo, and the filtrate is washed with brine, dried with sodium sulphate and evaporated. The title compound is obtained as a yellowish oil and is employed without further purification for the next stage.

The starting material is prepared as follows:

a) (S)-6-Oxaspiro[2.5]octane-1-carboxamide 18.85 g of carbonyldiimidazole are added to a solution of 17.66 g of (S)-6-oxaspiro[2.5]-octane-1-carboxylic acid (prepared in analogy to building block FFFFa from (R)-4-benzyl-3-((S)-6-oxaspiro[2.5]-octane-1-carbonyl)oxazolidin-2-one (building block FFFFb)) in 330 ml of ethyl acetate. The reaction solution is left to stand at room temperature for 6 hours and then 330 ml of 25% ammonium hydroxide solution are added. The reaction mixture is stirred at room temperature for 16 hours, the phases are separated, and the aqueous phase is extracted with ethyl acetate. The combined organic phases are washed with water until neutral, dried with sodium sulphate and evaporated. The title compound is obtained from the residue by flash chromatography ($SiO_2$ 60 F) as a yellowish oil which may crystallize if sufficiently pure. Rf=0.28 (dichloromethane-methanol-conc. ammonia 25% 200:20:1).

IIII C-(6-Oxaspiro[2.5]oct-1(R)-yl)methylamine

The title compound is obtained in analogy to building block HHHH from (R)-6-oxaspiro[2.5]octane-1-carboxylic acid (building block FFFFa).

JJJJ C—((Z)-2-Oxabicyclo[3.1.0]hex-1-yl)methylamine

The title compound is prepared in analogy to building block VVV from ((Z)-2-oxabicyclo[3.1.0]-hex-1-yl)methanol.

The starting materials are prepared as follows:

a) ((Z)-2-Oxabicyclo[3.1.0]hex-1-yl)methanol 2 mmol of a solution of borane-tetrahydrofuran complex (1M in tetrahydrofuran) are added to a solution of 1.0 mmol of (Z)-2-oxabicyclo[3.1.0]-hexane-1-carbaldehyde in 10 ml of tetra-hydrofuran at room temperature. The reaction mixture is stirred at room temperature for 2 hours and, after addition of 10 ml of methanol, concentrated. The title compound is identified by means of the Rf from the residue by flash chromatography ($SiO_2$ 60 F).

b) (Z)-2-Oxabicyclo[3.1.0]hexane-1-carbaldehyde

A solution of 0.66 mmol of 1(Z)-propenyl-(Z)-2-oxabicyclo[3.1.0]hexane [164118-97-2] and 0.80 mmol of N-methylmorpholine N-oxide hydrate in 20 ml of tetrahydrofuran-water-tert-butanol 4:4:1 is stirred at room temperature for 30 minutes. A solution of osmiumtetroxide (4% strength in water, 4 mol %) is added, the reaction mixture is stirred at room temperature for 16 hours and then quenched with 2M sodium thiosulphate solution and ethyl acetate. The mixture is stirred at room temperature for 3 hours, the phases are separated, and the organic phase is washed with brine and evaporated. The residue is dissolved in 20 ml of ethyl acetate, and 1.0 mmol of lead tetraacetate is added. The suspension is stirred at room temperature for 10 minutes, filtered through a little $SiO_2$ 60 F and evaporated. The title compound is identified by means of the Rf from the residue by flash chromatography ($SiO_2$ 60 F).

KKKK C—((Z)-3-Oxabicyclo[3.1.0]hex-1-yl)methylamine

The title compound is prepared in analogy to building block VVV from ((Z)-3-oxabicyclo[3.1.0]-hex-1-yl)methanol.

The starting materials are prepared as follows:

a) ((Z)-3-Oxabicyclo[3.1.0]hex-1-yl)methanol 1.5 mmol of tetrabutylammonium fluoride solution (1M in tetrahydrofuran) are added to a solution of 1 mmol of tert-butyldimethyl-((Z)-3-oxabicyclo[3.1.0]-hex-1-ylmethoxy)silane in 10 ml of tetrahydrofuran at 0° C. The reaction mixture is stirred at room temperature for 2 hours, poured into 1M sodium bicarbonate solution and extracted with tert-butyl methyl ether (2×). The combined organic phases are washed with brine, dried with sodium sulphate and evaporated. The title compound is identified by means of the Rf from the residue by means of flash chromatography ($SiO_2$ 60 F).

b) tert-Butyldimethyl-((Z)-3-oxabicyclo[3.1.0]hex-1-ylmethoxy)silane 5.07 mmol of diethyl zinc and 10.02 mmol of chloroiodomethane are successively added dropwise to a solution of 2.52 mmol of tert-butyl-(2,5-dihydrofuran-3-ylmethoxy)dimethyl-silane [144186-63-0] in 12.5 ml of dichloroethane at 0° C. The reaction mixture is stirred at 0° C. for 20 minutes and then cautiously quenched with saturated ammonium chloride solution at 0° C. The mixture is warmed to room temperature and stirred vigorously for 10 minutes. It is extracted with tert-butyl methyl ether (3×), and the combined organic phases are washed with water and brine, dried with sodium sulphate and evaporated. The title compound is identified by means of the Rf from the residue by flash chromatography ($SiO_2$ 60 F).

LLLL C-((exo,endo)-2-Oxabicyclo[4.1.0]hept-7-yl)methylamine

The title compound is prepared in analogy to building block VVV from ((exo,endo)-2-oxabicyclo[4.1.0]hept-7-yl)methanol [51197-04-7], [51144-35-5].

MMMM (exo,endo)-2-Oxabicyclo[4.1.0]hept-7-ylamine

The title compound is prepared in analogy to building block DDDD from (exo,endo)-2-oxabicyclo[4.1.0]-heptane-7-carboxylic acid.

a) (exo,endo)-2-Oxabicyclo[4.1.0]heptane-7-carboxylic acid

The title compound is prepared in analogy to building block FFFFa from ((exo,endo)-2-oxabicyclo[4.1.0]-hept-7-yl)methanol [51197-04-7], [51144-35-5].

NNNN (7,9trans,7exo)-7-Methoxy-3-oxabicyclo[3.3.1]non-9-ylamine

A solution of 1.8 mmol of hydroxylamine hydrochloride in 0.5 ml of water is added to a solution of 0.9 mmol of (7exo)-7-methoxy-3-oxabicyclo[3.3.1]-nonan-9-one in 5 ml of ethanol, and the mixture is heated to reflux overnight. The reaction mixture is concentrated and partitioned between saturated sodium carbonate solution and diethyl ether. The phases are separated, and the aqueous phase is extracted with diethyl ether (2×). The combined organic phases are dried with sodium sulphate and evaporated. The residue is dissolved in 5 ml of ethanol and, over the course of 2 hours, 12.8 mmol of zinc dust and 0.8 ml of glacial acetic acid are alternately added each in small portions. The internal temperature must not exceed 50° C. during the addition. The reaction mixture is stirred at room temperature for 12 hours and filtered through Hyflo, and the filter cake is washed with cold ethanol. The solution is evaporated, and the residue is partitioned between 4M NaOH and diethyl ether. The phases are separated and the aqueous phase is extracted with diethyl ether (2×). The combined organic phases are dried with sodium sulphate and evaporated. The title compound is identified by means of the Rf from the residue by flash chromatography (SiO$_2$ 60 F).

The starting materials are prepared as follows:

a)
(7exo)-7-Methoxy-3-oxabicyclo[3.3.1]nonan-9-one

A solution of 1 mmol of (7exo)-7,9,9-trimethoxy-3-oxabicyclo[3.3.1]-nonane in 10 ml of methanol is mixed with 10 ml of 2M HCl and heated to reflux for 3 hours. It is cooled to room temperature and concentrated. The residue is extracted with chloroform (3×). The combined organic phases are washed with sodium bicarbonate solution, dried with sodium sulphate and evaporated. The title compound is identified by means of the Rf from the residue by flash chromatography (SiO$_2$ 60 F).

b)
(7exo)-7,9,9-Trimethoxy-3-oxabicyclo[3.3.1]nonane

A solution of 1.3 mmol of (7exo)-9,9-dimethoxy-3-oxabicyclo[3.3.1]-nonan-7-ol in 10 ml of dimethylformamide is mixed with 5.2 mmol of methyl iodide and cooled to 0° C. 1.9 mmol of sodium hydride (60% dispersion in oil) are added in portions, and the mixture is stirred at 0° C. for 1 hour. Saturated sodium bicarbonate solution is added, and the mixture is extracted with tert-butyl methyl ether (2×). The combined organic phases are washed with water and brine, dried with sodium sulphate and evaporated. The title compound is identified by means of the Rf from the residue by flash chromatography (SiO$_2$ 60 F).

c)
(7exo)-9,9-Dimethoxy-3-oxabicyclo[3.3.1]nonan-7-ol 5.4 mmol of benzoic acid and 5.4 mmol of triphenylphosphine are added to a solution of 4.5 mmol of (7endo)-9,9-dimethoxy-3-oxabicyclo[3.3.1]-nonan-7-ol in 100 ml of tetrahydro-furan. Then 4.5 mmol of diisopropyl azodicarboxylate are added dropwise, and the mixture is stirred at room temperature for 5 hours. Saturated sodium bicarbonate solution is added, the phases are separated, and the aqueous phase is extracted with dichloromethane (2×). The combined organic phases are dried with sodium sulphate and evaporated. The residue is dissolved in 35 ml of methanol and, after addition of 17 mmol of potassium carbonate, stirred at room temperature for 5 hours. The reaction mixture is evaporated and the residue is taken up in dichloromethane. Saturated ammonium chloride solution is added, the phases are separated, and the aqueous phase is extracted with dichloromethane (2×). The combined organic phases are dried with sodium sulphate and evaporated. The title compound is identified by means of the Rf from the residue by flash chromatography (SiO$_2$ 60 F).

d) (7endo)-9,9-Dimethoxy-3-oxabicyclo[3.3.1]nonan-7-ol

A solution of 1.89 mmol of 9,9-dimethoxy-3-oxabicyclo[3.3.1]-nonan-7-one in 2 ml of tetra-hydrofuran is added dropwise to a suspension of 3.68 mmol of lithium aluminium hydride in 4.5 ml of tetrahydrofuran at −20° C. The reaction mixture is stirred at −20° C. for 40 hours. Then, successively, 144 µl of water, 144 µl of 5M NaOH and 432 µl of water are cautiously added, and the mixture is stirred at room temperature for 25 minutes. The reaction mixture is filtered through Hyflo and evaporated. The title compound is identified by means of Rf from the residue by flash chromatography (SiO$_2$ 60 F).

e) 9,9-Dimethoxy-3-oxabicyclo[3.3.1]nonan-7-one 6 mmol of (7endo)-(9,9-dimethoxy-3-oxabicyclo[3.3.1]-non-7-yl)phenylmethanone are added to a mixture of 6.7 mmol of potassium tert-butoxide in 25 ml of tert-butanol and 100 ml of hexamethylphosphoric triamide under an oxygen atmosphere. The reaction mixture is stirred at room temperature for 30 minutes and poured into ice-water. It is extracted with benzene/tetrahydrofuran (3×). The combined organic phases are washed with brine, dried with sodium sulphate and evaporated. The title compound is identified by means of the Rf from the residue by flash chromatography (SiO$_2$ 60 F).

f) (7endo)-(9,9-Dimethoxy-3-oxabicyclo[3.3.1]non-7-yl)phenylmethanone

A solution of 1 mmol of (7endo)-7-benzoyl-3-oxabicyclo [3.3.1]-nonan-9-one in 20 ml of methanol is mixed with 1 ml of conc. H$_2$SO$_4$ and refluxed in a Dean-Stark apparatus for 3 hours. The reaction solution is cooled to room temperature and concentrated. The residue is extracted with chloroform (3×). The combined organic phases are washed with sodium bicarbonate solution, dried with sodium sulphate and evaporated. The title compound is identified by means of the Rf from the residue by flash chromatography (SiO$_2$ 60 F).

g)
(7endo)-7-Benzoyl-3-oxabicyclo[3.3.1]nonan-9-one 140 mg of tosyl chloride are added to a solution of 50 mmol of tetrahydropyran-4-one [29943-42-8] and 11 ml of pyrrolidine in 50 ml of benzene, and the reaction mixture is refluxed in a Dean-Stark apparatus for 3 hours. The reaction solution is cooled to room temperature and evaporated. The residue is dissolved in 200 ml of acetonitrile and 60 mmol of triethylamine and, after addition of a solution of 50 mmol of 2-benzoyl-1,3-dichloropropane [39192-57-9] in 100 ml of acetonitrile, stirred at room temperature for 2 hours. The reaction mixture is quenched with water, stirred for 1 hour and evaporated. The residue is mixed with water and extracted with chloroform (2×). The combined organic phases are washed with 2M HCl and 1M sodium bicarbonate solution, dried with sodium sulphate and evaporated. The title compound is identified by means of the Rf from the residue by flash chromatography (SiO$_2$ 60 F).

OOOO (7,9cis,7endo)-7-Methoxy-3-oxabicyclo[3.3.1]non-9-ylamine

The title compound is prepared in analogy to building block NNNN from (7endo)-9,9-dimethoxy-3-oxabicyclo[3.3.1]-nonan-7-ol (building block NNNN d).

RRRR C-(Tetrahydrofuran-3-yl)methylamine

The title compound is prepared in analogy to building block VVV from (tetrahydrofuran-3(S)-yl)methanol [124391-75-9].

SSSS C-(Tetrahydrofuran-3(R)-yl)methylamine

The title compound is prepared in analogy to building block VVV from (tetrahydrofuran-3-yl)methanol [124506-31-6].

TTTT C-(Tetrahydropyran-3(R)-yl)methylamine

The title compound is prepared in analogy to building block NNNN from tetrahydropyran-3(S)-carbaldehyde [141822-85-7].

UUUU C-(Tetrahydropyran-3(S)-yl)methylamine

The title compound is prepared in analogy to building block NNNN from tetrahydropyran-3(R)-carbaldehyde [143810-10-0].

XXXX (cis)-5-Methoxytetrahydropyran-3-ylamine

The title compound is prepared in analogy to building block DDDD from (cis)-5-methoxy-tetrahydropyran-3-carboxylic acid.

The starting materials are prepared as follows:

a) (cis)-5-Methoxytetrahydropyran-3-carboxylic acid

A solution of 10.55 mmol of methyl (cis)-5-methoxytetrahydropyran-3-carboxylate in 45 ml of methanol is mixed with 45 ml of 1M LiOH and stirred at room temperature for one hour. The reaction mixture is evaporated, and the residue is taken up in dichloromethane. The pH is adjusted to 2 with 2M HCl, the phases are separated, and the aqueous phase is extracted with dichloromethane (2×). The combined organic phases are dried with sodium sulphate and evaporated. The crude title compound is identified by means of the Rf from the residue.

b) Methyl (cis)-5-methoxytetrahydropyran-3-carboxylate 15 ml of 50% NaOH, 367 mg of benzyltriethylammonium bromide and 0.95 ml of dimethyl sulphate are added to a solution of 1.05 g of methyl (cis)-5-hydroxytetrahydropyran-3-carboxylate in 30 ml of toluene. The two-phase mixture is stirred at room temperature for 18 hours. A further 1 ml of dimethyl sulphate is added. The mixture is stirred at room temperature for a further 6 hours, then diluted with water and ethyl acetate, and stirred at room temperature for 20 minutes. The phases are separated, and the aqueous phase is extracted with ethyl acetate. The combined organic phases are washed with brine, dried with sodium sulphate and evaporated. The crude title compound is identified. by means of the Rf from the residue.

c) Methyl (cis)-5-hydroxytetrahydropyran-3-carboxylate

A solution of diazomethane in diethyl ether (approx. 0.4 M) is added in excess to a solution of 23 mmol of (cis)-5-hydroxytetrahydropyran-3-carboxylic acid in 300 ml of methanol at 0° C. The mixture is stirred at 0° C. for 2 hours and then quenched with magnesium sulphate, filtered and evaporated. The crude title compound is identified by means of the Rf.

d) (cis)-5-Hydroxytetrahydropyran-3-carboxylic acid

A solution of 25.5 mmol of (cis)-3,6-dioxabicyclo[3.2.1]-octan-7-one in 500 ml of methanol is adjusted to pH 9 with 0.1M NaOH. The solution is stirred at constant pH until conversion is complete, and is adjusted to pH 6.5 with 0.1 M HCl before the methanol is evaporated off. The title compound is identified from the aqueous solution by means of the Rf by ion exchange chromatography (Amberlite XAD-2 resin).

e) (cis)-3,6-Dioxabicyclo[3.2.1]octan-7-one and methyl (trans)-5-hydroxytetrahydropyran-3-carboxylate A solution of 39 mmol of methyl 5-oxotetrahydropyran-3-carboxylate [127956-19-8] in. 500 ml of methanol is cooled to 0° C., and 50 mmol of sodium borohydride are added in portions. The solution is stirred at 0° C. for 3 hours and quenched with water. It is neutralized with acetic acid, and water and tert-butyl methyl ether are added. The phases are separated, and the aqueous phase is extracted with tert-butyl methyl ether (2×). The combined organic phases are washed with brine, dried with sodium sulphate and evaporated. The title compound is identified by means of the Rf from the residue by flash chromatography ($SiO_2$ 60 F).

YYYY (trans)-5-Methoxytetrahydropyran-3-ylamine

The title compound is prepared in analogy to building block DDDD from (trans)-5-methoxy-tetrahydropyran-3-carboxylic acid.

The starting materials are prepared as follows:

a) (trans)-5-Methoxytetrahydropyran-3-carboxylic acid

The title compound is prepared in analogy to building block XXXXa from methyl (trans)-5-methoxytetrahydropyran-3-carboxylate.

b) Methyl (trans)-5-methoxytetrahydropyran-3-carboxylate

The title compound is prepared in analogy to building block XXXXb from methyl (trans)-5-hydroxytetrahydropyran-3-carboxylate (building block XXXXe).

ZZZZ (cis)-C-(5-Methoxytetrahydropyran-3-yl)methylamine

The title compound is prepared in analogy to building block VVV from (cis)-(5-methoxytetra-hydropyran-3-yl)methanol.

The starting material is prepared as follows:

a) (cis)-(5-Methoxytetrahydropyran-3-yl)methanol

The title compound is prepared in analogy to building block FFFFb from methyl (cis)-5-methoxytetrahydropyran-3-carboxylate (building block)(XXXb)).

AAAAA (trans)-C-(5-Methoxytetrahydropyran-3-yl)methylamine

The title compound is prepared in analogy to building block ZZZZ from methyl (trans)-5-methoxytetrahydropyran-3-carboxylate (building block YYYYb).

BBBBB (cis)-5-Methoxyoxepan-3-ylamine

The title compound is prepared in analogy to building block XXXX from methyl (cis)-5-methoxyoxepane-3-carboxylate.

The starting materials are prepared as follows:

a) Methyl (cis)-5-methoxyoxepane-3-carboxylate

The title compound is prepared in analogy to building block XXXX b-d from (cis)-3,7-dioxabicyclo[4.2.1]-nonan-8-one.

b) (cis)-3,7-Dioxabicyclo[4.2.1]nonan-8-one and methyl (trans)-5-hydroxyoxepane-3-carboxylate The title compounds are prepared in analogy to building block XXXX e from methyl 5-oxooxepane-3-carboxylate [12756-13-2].

CCCCC (trans)-5-Methoxyoxepan-3-ylamine

The title compound is prepared in analogy to building block YYYY from methyl (trans)-5-methoxyoxepane-3-carboxylate.
The starting material is prepared as follows:

a) Methyl (trans)-5-methoxyoxepane-3-carboxylate

The title compound is prepared in analogy to building block XXXX b from methyl (trans)-5-hydroxyoxepane-3-carboxylate (building block BBBBB b).

DDDDD
(cis)-C-(5-Methoxyoxepan-3-yl)methylamine

The title compound is prepared in analogy to building block ZZZZ from methyl (cis)-5-methoxyoxepane-3-carboxylate (building block BBBBB a).

FFFFF 6(R)-Methoxyoxepan-4-ylamine 2.8 mmol of sodium cyanoborohydride, 2.8 mmol of ammonium acetate and 530 mg of 4 Å molecular sieves are added to a solution of 2.8 mmol of 6(R)-methoxyoxepan-4-one in 11 ml of methanol. The reaction mixture is stirred for 18 hours and conc. HCl is added until the pH falls below 3 and a white precipitate becomes visible. The mixture is concentrated and, after addition of water, extracted with dichloromethane (1×). The aqueous phase is adjusted to pH 12 with 6M NaOH and extracted with dichloromethane (3×). The combined organic phases are washed with water, dried with sodium sulphate and evaporated. The title compound is identified by means of the Rf from the residue by flash chromatography (SiO$_2$ 60 F).
The starting materials are prepared as follows:

a) 6(R)-Methoxyoxepan-4-one

The title compound is prepared in analogy to building block JJJJ b from 3(R)-methoxy-5-methyleneoxepane.

b) 3(R)-Methoxy-5-methyleneoxepane

The title compound is prepared in analogy to building block XXXX b from 3-hydroxy-5-methyleneoxepane [138907-09-2].

GGGGG 6-Methoxyoxepan-3-ylamine

The title compound is prepared in analogy to building block FFFFF from 6-hydroxyoxepan-3-one [120741-87-9].

HHHHH
C-(4(R)-Methoxytetrahydrofuran-2(R)-yl)methylamine

The title compound is prepared in analogy to building block VVV from (4(R)-methoxytetra-hydrofuran-2(R)-yl) methanol.
The starting materials are prepared as follows:

a) (4(R)-Methoxytetrahydrofuran-2(R)-yl)methanol

The title compound is prepared in analogy to building block CCCC a from methyl 4(R)-methoxytetrahydrofuran-2(R)-carboxylate.

b) Methyl 4(R)-methoxytetrahydrofuran-2(R)-carboxylate

The title compound is prepared in analogy to building block XXXX b from methyl 4(R)-hydroxytetrahydrofuran-2(R)-carboxylate.

c) Methyl 4(R)-hydroxytetrahydrofuran-2(R)-carboxylate

The title compound is prepared in analogy to building block NNNN c from methyl 4(S)-hydroxytetrahydrofuran-2(R)-carboxylate [2208-93-7].

IIIII
C-(4(S)-Methoxytetrahydrofuran-2(R)-yl)methylamine

The title compound is prepared in analogy to building block HHHHH from methyl 4(S)-hydroxytetrahydrofuran-2(R)-carboxylate [2208-93-7].

JJJJJ
C-(4(R)-Methoxytetrahydrofuran-2(S)-yl)methylamine

The title compound is prepared in analogy to building block HHHHH from methyl 4(R)-hydroxytetrahydrofuran-2(S)-carboxylate [2209-10-1].

KKKKK
C-(4(S)-Methoxytetrahydrofuran-2(S)-yl)methylamine

The title compound is prepared in analogy to building block HHHHH from methyl 4(S)-hydroxytetrahydrofuran-2(S)-carboxylate [2209-09-08].

LLLLL
(1S,2R,4S)-7-Oxabicyclo[2.2.1]hept-2-ylamine

The title compound is prepared in analogy to building block DDDD from (1S,2R,4S)-7-oxabicyclo[2.2.1]-heptane-2-carboxylic acid.
The starting material is prepared as follows:

a)
(1S,2R,4S)-7-Oxabicyclo[2.2.1]heptane-2-carboxylic acid

A solution of 1 mmol of (1S,2R,4S)-7-oxabicyclo[2.2.1]-hept-5-ene-2-carboxylic acid [185840-15-7] in 30 ml of ethanol is hydrogenated in the presence of 0.150 g of Pd/C 10% at room temperature until conversion is complete. The reaction mixture is clarified by filtration, and the filtrate is evaporated. The title compound is obtained from the residue by flash chromatography (SiO$_2$ 60 F).

MMMMM
(1R,2S,4R)-7-Oxabicyclo[2.2.1]hept-2-ylamine

The title compound is prepared in analogy to building block LLLLL from (1R,2S,4R)-7-oxabicyclo[2.2.1]-hept-5-ene-2-carboxylic acid.

The starting material is prepared as follows:

a) (1R,2S,4R)-7-Oxabicyclo[2.2.1]hept-5-ene-2-carboxylic acid

A solution of 1 mmol of (1R,2R)-2-(naphthalene-2-sulphonyl)cyclohexyl ester (exo)-(1R,2S,4R)-7-oxabicyclo[2.2.1]-hept-5-ene-2-carboxylate in 5 ml of N,N-dimethylformamide is mixed with 2 mmol of potassium hydroxide and stirred at 60° C. for 17 hours. The reaction mixture is cooled to room temperature and, after addition of 1M citric acid solution, extracted with tert-butyl methyl ether (3×). The combined organic phases are washed with cold water and cold brine, dried with sodium sulphate and evaporated at room temperature. The title compound is identified by means of the Rf from the residue by flash chromatography (SiO$_2$ 60 F).

NNNNN
(1R,2R,4R)-7-Oxabicyclo[2.2.1]hept-2-ylamine

The title compound is prepared in analogy to building block LLLLL from (1R,2R,4R)-7-oxabicyclo[2.2.1]-hept-5-ene-2-carboxylic acid [90760-55-7].

OOOOO
(1S,2S,4S)-7-Oxabicyclo[2.2.1]hept-2-ylamine

The title compound is prepared in analogy to building block LLLLL from (1S,2S,4S)-7-oxabicyclo[2.2.1]-hept-5-ene-2-carboxylic acid [90760-56-8].

PPPPP 2-Oxabicyclo[2.2.1]hept-6-ylamine

The title compound is prepared in analogy to building block NNNN from 2-oxabicyclo[2.2.1]-heptan-6-one [34108-25-3].

QQQQQ
(exo)-(2,5-Dioxabicyclo[4.1.0]hept-7-yl)amine

The title compound is prepared in analogy to building block DDDD from (exo)-2,5-dioxabicyclo[4.1.0]-heptane-7-carboxylic acid [60170-70-9].

RRRRR (exo)-(2,5-Dioxabicyclo[4.1.0]hept-7-ylmethyl)amine

The title compound is prepared in analogy to building block BBBB from ethyl (exo)-2,5-dioxabicyclo[4.1.0]-heptane-7-carboxylate [60170-67-4].

SSSSS C-[(cis)-1-(3-Oxabicyclo[3.1.0]hex-2-yl)]methylamine

The title compound is prepared in analogy to the processes described for building blocks BBBB and MMMM from methyl (cis)-3-oxabicyclo[3.1.0]-hexane-2-carboxylate.

The starting materials are prepared as follows:

a) Methyl (cis)-3-oxabicyclo[3.1.0]hexane-2-carboxylate

The title compound is prepared in analogy to building block XXXXc from (cis)-3-oxa-bicyclo[3.1.0]-hexane-2-carboxylic acid.

b) (cis)-3-Oxabicyclo[3.1.0]hexane-2-carboxylic acid

The title compound is prepared in analogy to building block FFFF a from (cis)-3-oxa-bicyclo[3.1.0]-hexane-2-methanol [85194-16-7].

TTTTT
C-[1-(Tetrahydropyran-4-yl)cyclopropyl]methylamine

The title compound is prepared in analogy to building block DDDD from 1-(tetrahydropyran-4-yl)cyclopropane carboxylic acid.

The starting materials are prepared as follows:

a) 1-(Tetrahydropyran-4-yl)cyclopropanecarboxylic acid

The title compound is prepared in analogy to building block FFFFd from ethyl 1-(tetra-hydropyran-4-yl)cyclopropanecarboxylate.

b) Ethyl 1-(tetrahydropyran-4-yl)cyclopropanecarboxylate 6.83 mmol of lithium diisopropylamide (2M in tetrahydrofuran) are added dropwise to a solution of 5.69 mmol of ethyl tetrahydropyranylacetate [103260-44-2] in 10 ml of tetrahydrofuran at −78° C. The mixture is stirred at −78° C. for 15 minutes and 7.39 mmol of dibromoethane are added. The reaction mixture is warmed to 0° C. over 15 minutes and then cooled again to −78° C. 6.83 mmol of lithium diisopropylamide (2M in tetrahydrofuran) are again added dropwise to the reaction mixture. It is warmed to room temperature over 2 hours and quenched with 1M HCl. The phases are separated and the aqueous phase is extracted with tert-butyl methyl ether (2×). The combined organic phases are washed with brine, dried with sodium sulphate and evaporated. The title compound is identified by means of the Rf from the residue by flash chromatography (SiO$_2$ 60 F).

UUUUU
C-[1-(Tetrahydropyran-4-yl)cyclopropyl]methylamine

The title compound is prepared in analogy to building block BBBB from ethyl 1-(tetrahydropyran-4-yl)cyclopropanecarboxylate (building block TTTTTb).

VVVVV
2-Methyl-2-(tetrahydropyran-4-yl)propylamine

The title compound is prepared in analogy to building block BBBB from ethyl 2-methyl-2-(tetrahydropyran-4-yl)propionate [865156-84-9].

WWWWW
2,2-Difluoro-2-(tetrahydropyran-4-yl)ethylamine

The title compound is prepared in analogy to building block BBBB from methyl difluoro(tetrahydropyran-4-yl)acetate.

The starting materials are prepared as follows:

a) Methyl difluoro(tetrahydropyran-4-yl)acetate

The title compound is prepared in analogy to building block XXXX c from difluoro(tetrahydropyran-4-yl)acetic acid.

b) Difluoro(tetrahydropyran-4-yl)acetic acid

A solution of 0.774 mmol of 2-[1,1-dichloro-2,2-difluoro-2-(tetrahydropyran-4-yl)ethylsulphanyl]pyridine in 4 ml of tetrahydrofuran is mixed with 3.096 mmol of silver nitrate solution (in 4 ml of water). The cloudy mixture is heated to reflux for 3 hours. The reaction mixture is cooled to room temperature and filtered through Hyflow. The filtrate is adjusted to pH 9-10 with 50% strength sodium bicarbonate solution and washed with diethyl ether. The aqueous phase is subsequently adjusted to pH 1 with 50% strength $H_2SO_4$ and extracted with dichloromethane. The combined organic phases are dried with sodium sulphate and evaporated. The title compound is obtained as a yellow solid from the residue.

c) 2-[1,1-Dichloro-2,2-difluoro-2-(tetrahydropyran-4-yl)ethylsulphanyl]pyridine 2.422 mmol of N,N'-dicyclohexylcarbodiimide are added to a solution of 2.422 mmol of tetrahydropyran-4-carboxylic acid [5337-03-1] and 2.422 mmol of hydroxythiopyrimidone [1121-31-9] in 5 ml of dichloromethane at room temperature with exclusion of light. The reaction mixture is stirred at room temperature for 3 hours. It is filtered through Hyflow, and the filtrate is evaporated with exclusion of light. The yellow residue is dissolved in 4 ml of acetonitrile, the solution is cooled to 0° C., and 24.22 mmol of 1,1-dichloro-2,2-difluoroethylene [79-35-6] are added. The reaction mixture is stirred under the influence of light (300 W sunlamp) at −10° C. for 2.5 hours. It is evaporated. The title compound is obtained as a pale yellow oil from the residue by flash chromatography ($SiO_2$ 60 F). Rf=0.26 (EtOAc/heptane1:1); Rt=4.25 (gradient I).

XXXXX (syn/anti, exo)-3-Methoxybicyclo[3.1.0]hex-6-ylamine

The title compound is prepared in analogy to the methods described for the building blocks under XXXX e, NNNN b and for building block BBBB from methyl (exo)-(1R,5S,6R)-3-oxo-bicyclo[3.1.0]-hexane-6-carboxylate [24137-53-9].

Exemplary compounds 1ZZ to 1PPPPP correspond to the formula

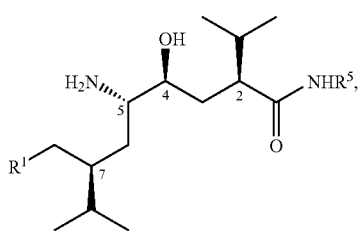

(II)

in which $R^1$ corresponds to the radical 1 indicated above, and $NHR^5$ in each exemplary compound 1ZZ to 1FFFFFF corresponds to one of the abovementioned radicals ZZ to FFFFFF. The atoms identified by * are bonding positions. The further examples 2ZZ to 55FFFFFF are accordingly exemplary compounds of the formula (II) where the radical $NHR^5$ can assume all the abovementioned definitions (ZZ to FFFFFF) for a given radical $R^1$ (abovementioned definitions 1-55). Consequently, Example 49VFFF corresponds to the compound 5-amino-4-hydroxy-2-isopropyl-7-[3-(3-methoxypropyl)-7-methylimidazo[1,2-a]pyridin-6-ylmethyl]-8-methyl-thyl-N—[(S)-1-(tetrahydrofuran-2-yl)methyl]nonanamide. The remaining compounds 1ZZ to 55FFFFFF are obtained in analogy to the preparation processes described below in detail.

Example 49FFF

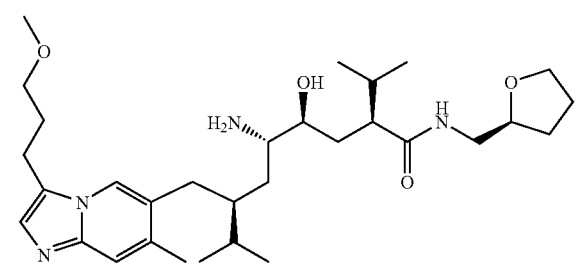

5-Amino-4-hydroxy-2-isopropyl-7-[3-(3-methoxypropyl)-7-methylimidazo[1,2-a]pyridin-6-ylmethyl]-8-methyl-N—[(S)-1-(tetrahydrofuran-2-yl)methyl]nonanamide In analogy to method F, the title compound is identified by means of the Rf from 0.510 g of 4-azido-5-hydroxy-2-isopropyl-1-[3-(3-methoxypropyl)-7-methylimidazo[1,2-a]pyridin-6-yl]-8-methyl-7-{[(S)-1-(tetrahydrofuran-2-yl)methyl]carbamoyl}nonyl tert-butyl carbonate.

The starting materials are prepared as follows:

a) 4-Azido-5-hydroxy-2-isopropyl-1-[3-(3-methoxypropyl)-7-methylimidazo[1,2-a]pyridin-6-yl]-8-methyl-7-{[(S)-1-(tetrahydrofuran-2-yl)methyl]carbamoyl}nonyl tert-butyl carbonate The title compound is obtained as a beige foam in analogy to method B from 0.500 g of 2-[2-azido-2-(4-isopropyl-5-oxotetrahydrofuran-2-yl)ethyl]-1-[3-(3-methoxypropyl)-7-methylimidazo[1,2-a]pyridin-6-yl]-3-methylbutyl tert-butyl carbonate and 0.3456 g of C—[(S)-1-(tetrahydrofuran-2-yl)]methylamine (Example FFF). Rf=0.51 (dichloromethane-methanol-conc. ammonia 25% 200:20:1); Rt=4.28 (Gradient I).

b) 2-[2-Azido-2-(4-isopropyl-5-oxotetrahydrofuran-2-yl)ethyl]-1-[3-(3-methoxypropyl)-7-methylimidazo[1,2-a]pyridin-6-yl]-3-methylbutyl tert-butyl carbonate The title compound is obtained as a yellow foam in analogy to method A from 2.0 g of 5-(1-azido-3-{hydroxy-[3-(3-methoxypropyl)-7-methylimidazo[1,2-a]pyridim-6-yl]methyl}-4-methylpentyl)-3-isopropyldihydrofuran-2-one. Rf=0.28 (dichloromethane-methanol-conc. ammonia 25% 200:10:1); Rt=4.93 (Gradient I).

c) 5-(1-Azido-3-{hydroxy-[3-(3-methoxypropyl)-7-methylimidazo[1,2-a]pyridin-6-yl]methyl}-4-methylpentyl)-3-isopropyldihydrofuran-2-one The title compound is obtained as a yellow resin in analogy to method I from 10 g of 6-bromo-3-(3-methoxypropyl)-7- methylimidazo[1,2-a]pyridine (building block 49). Rf=0.06 (dichloromethane-methanol-conc. ammonia 25% 200:10:1); Rt=4.10 (Gradient I).

Example 48FFFF

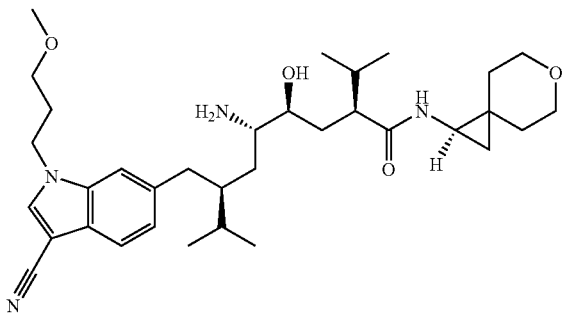

5-Amino-7-[3-cyano-1-(3-methoxypropyl)-1H-indol-6-ylmethyl]-4-hydroxy-2-isopropyl-8-methyl-N—(R)-(6-oxaspiro[2.5]oct-1-yl)nonanamide The title compound is identified by means of the Rf in analogy to method E from 0.5 mmol of tert-butyl [1-{2-[3-cyano-1-(3-methoxypropyl)-1H-indol-6-ylmethyl]-3-methylbutyl}-4-(R)-(6-oxaspiro[2.5]-oct-1-yl)carbamoyl)-2-hydroxy-5-methylhexyl]carbamate.

The starting materials are prepared as follows:

a) tert-Butyl [1-{2-[3-cyano-1-(3-methoxypropyl)-1H-indol-6-ylmethyl]-3-methylbutyl}-4-((R)-(6-oxaspiro[2.5]oct-1-yl)carbamoyl)-2-hydroxy-5-methylhexyl]carbamate A solution of 1 mmol of tert-butyl (4-((R)-(6-oxaspiro[2.5]-oct-1-yl)carbamoyl)-2-hydroxy-1-(2-[1-(3-methoxypropyl)-1H-indol-6-ylmethyl]-3-methylbutyl)-5-methylhexyl)carbamate in 15 ml of dichloromethane is mixed with 1.5 mmol of chlorosulphonyl isocyanate and stirred at room temperature for 16 hours. 2 ml of N,N-dimethylformamide are added, and the reaction mixture is again stirred for 2 hours. It is quenched with water, and the suspension is vigorously stirred for 10 minutes. It is poured into 1M sodium bicarbonate solution and extracted with ethyl acetate (3×). The combined organic phases are washed with brine, dried with sodium sulphate and evaporated. The title compound is identified by means of the Rf from the residue by flash chromatography (SiO$_2$ 60 F).

b) tert-Butyl (4-((R)-(6-oxaspiro[2.5]oct-1-yl)carbamoyl)-2-hydroxy-1-{2-[1-(3-methoxypropyl)-1H-indol-6-ylmethyl]-3-methylbutyl}-5-methylhexyl) carbamate The title compound is identified by means of the Rf in analogy to method B from 0.6 mmol of tert-butyl {1-(4-isopropyl-5-oxotetrahydrofuran-2-yl)-3-[1-(3-methoxypropyl)-1H-indol-6-ylmethyl]-4-methylpentyl}carbamate and 12 mmol of (R)-(6-oxaspiro[2.5]-oct-1-yl)amine (Example FFFF).

c) tert-Butyl 1-(4-isopropyl-5-oxotetrahydrofuran-2-yl)-3-[1-(3-methoxypropyl)-1H-indol-6-ylmethyl]-4-methylpentyl}carbamate The title compound is identified by means of the Rf in analogy to method D from 2.5 mmol of 5-{1-amino-3-[1-(3-methoxypropyl)-1H-indol-6-ylmethyl]-4-methylpentyl}-3-isopropyldihydrofuran-2-one.

d) 5-{1-Amino-3-[1-(3-methoxypropyl)-1H-indol-6-ylmethyl]-4-methylpentyl}-3-isopropyldihydrofuran-2-one 6.27 g of 2-[2-azido-2-(4-isopropyl-5-oxotetrahydrofuran-2-yl)ethyl]-1-[1-(3-methoxypropyl)-1H-indol-6-yl]-3-methylbutyl methyl carbonate are reacted in analogy to method F. The title compound is obtained as a yellow oil; Rt=4.39 (Gradient I).

e) 2-[2-Azido-2-(4-isopropyl-5-oxotetrahydrofuran-2-yl)ethyl]-1-[1-(3-methoxypropyl)-1H-indol-6-yl]-3-methylbutyl methyl carbonate The title compound is obtained as a yellow oil in analogy to method G from 7.1 g of 5-(1-azido-3-{hydroxy-[1-(3-methoxypropyl)-1H-indol-6-yl]methyl}-4-methylpentyl)-3-isopropyl-dihydrofuran-2-one. Rf=0.24 (EtOAc-heptane 1:1); Rt=24.20 (Gradient II).

f) 5-(1-Azido-3-{hydroxy-[1-(3-methoxypropyl)-1H-indol-6-yl]methyl}-4-methylpentyl)-3-isopropyldihydrofuran-2-one The title compound is obtained as a yellow oil in analogy to method H from 1.49 g of 6-bromo-1-(3-methoxypropyl)-1H-indole (building block 5). Rf=0.35 (EtOAc-heptane 1:1); Rt=23.06 (Gradient II).

Example 46BBBB

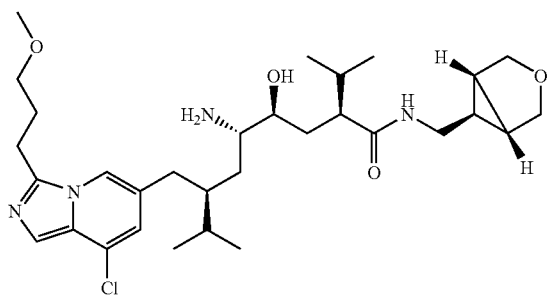

5-Amino-7-[8-chloro-3-(3-methoxypropyl)imidazo[1,5-a]pyridin-6-ylmethyl]-4-hydroxy-2-isopropyl-8-methyl-N-((exo)-C-[1-(3-oxabicyclo[3.1.0]hex-6-yl)]methyl)nonanamide 0.3 mmol of tert-butyl [1-{2-[8-chloro-3-(3-methoxypropyl)imidazo[1,5-a]pyridin-6-ylmethyl]-3-methylbutyl}-2-hydroxy-5-methyl-4-((exo)-C-[1-(3-oxabicyclo[3.1.0]-hex- 6-yl)]methyl-carbamoyl)hexyl]carbamate is reacted in analogy to method E. The title compound is identified by means of its Rf.

The starting materials are prepared as follows:

a) tert-Butyl [1-{2-[8-chloro-3-(3-methoxypropyl)imidazo[1,5-a]pyridin-6-ylmethyl]-3-methylbutyl}-2-hydroxy-5-methyl-4-((exo)-C-[1-(3-oxabicyclo[3.1.0]hex-6-yl)]methylcarbamoyl)hexyl]carbamate The title compound is identified by means of the Rf in analogy to method B from 0.6 mmol of tert-butyl [3-[8-chloro-3-(3-methoxypropyl)imidazo[1,5-a]pyridin-6-ylmethyl]-1-(4-isopropyl-5-oxotetrahydrofuran-2-yl)-4-methylpentyl]carbamate and 3.0 mmol of (exo)-C-[1-(3-oxabicyclo[3.1.0]-hex-6-yl)]methylamine (Example BBBB).

b) tert-Butyl [3-[8-chloro-3-(3-methoxypropyl)imidazo[1,5-a]pyridin-6-ylmethyl]-1-(4-isopropyl-5-oxotetrahydrofuran-2-yl)-4-methylpentyl]carbamate Tributyl tin hydride (1.32 mmol) is added to a degassed solution of 1.015 mmol of O-{2-[2-tert-butoxycarbonylamino-2-(4-isopropyl-5-oxotetrahydrofuran-2-yl)ethyl]-1-[8-chloro-3-(3-methoxypropyl)imidazo[1,5-a]pyridin-6-yl]-3-methylbutyl}imidazole-1-carbothioate and 0.162 mmol of 2,2'-azoisobutyronitrile in 15 ml of toluene. The flask is placed in an oil bath preheated to 120°, and the reaction solution is stirred under reflux for 3 hours. The reaction mixture is then cooled to room temperature, diluted with ethyl acetate and washed with 0.1M HCl and brine, dried with sodium sulphate and evaporated. The title compound is identified by means of the Rf from the residue by flash chromatography (SiO$_2$ 60 F).

c) O-{2-[2-tert-Butoxycarbonylamino-2-(4-isopropyl-5-oxotetrahydrofuran-2-yl)ethyl]-1-[8-chloro-3-(3-methoxypropyl)imidazo[1,5-a]pyridin-6-yl]-3-methylbutyl}imidazole-1-carbothioate A solution of 1.52 mmol of tert-butyl [3-{[8-chloro-3-(3-methoxypropyl)imidazo[1,5-a]pyridin-6-yl]hydroxymethyl}-1-(4-isopropyl-5-oxotetrahydrofuran-2-yl)-4-methylpentyl]carbamate, 5.41 mmol of 1,1'-thiocarbonyldiimidazole and 0.15 mmol of 4-dimethylaminopyridine in 5 ml of tetrahydrofuran is heated to reflux for 3 hours. A further portion of 1,1'-thiocarbonyldiimidazole (1.6 mmol) is added, and the mixture is then heated to reflux for a further 3 hours. The reaction mixture is cooled to room temperature, diluted with ethyl acetate, washed with brine, dried with sodium sulphate and evaporated. The title compound is identified by means of the Rf from the residue by flash chromatography (SiO$_2$ 60 F).

d) tert Butyl [3-{[8-chloro-3-(3-methoxypropyl)imidazo[1,5-a]pyridin-6-yl]hydroxymethyl}-1-(4-isopropyl-5-oxotetrahydrofuran-2-yl)-4-methylpentyl]carbamate A solution of 2.72 mmol of 5-(1-azido-3-{[8-chloro-3-(3-methoxypropyl)imidazo[1,5-a]pyridin-6-yl]hydroxymethyl}-4-methylpentyl)-3-isopropyldihydrofuran-2-one in 15 ml of tetrahydrofuran is mixed with 3.264 mmol of triphenylphosphine and 0.064 ml of water. The reaction solution is stirred at room temperature for 16 hours. Water (0.40 ml) is added, and the reaction mixture is then heated to reflux for 8 hours. The reaction mixture is cooled to room temperature, diluted with tert-butyl methyl ether (100 Ml) and washed with brine (50 ml), dried with sodium sulphate and evaporated. The residue is dissolved in 20 ml of tetrahydrofuran, mixed with 4.08 mmol of Hünig's base and 3.264 mmol of tert-butyl dicarbonate and left to stand at room temperature for 12 hours. The reaction solution is diluted with tert-butyl methyl ether (50 ml) and washed with 0.1M HCl and brine, dried with sodium sulphate and evaporated. The title compound is identified by means of the Rf from the residue by flash chromatography (SiO$_2$ 60 F).

e) 5-(1-Azido-3-{[8-chloro-3-(3-methoxypropyl)imidazo[1,5-a]pyridin-6-yl]hydroxymethyl}-4-methylpentyl)-3-isopropyldihydrofuran-2-one 7.11 mmol of 6-bromo-8-chloro-3-(3-methoxypropyl)imidazo[1,2-a]pyridine (Example 46) are reacted in analogy to method I. The title compound is identified by means of the Rf.

Example 33JJJ

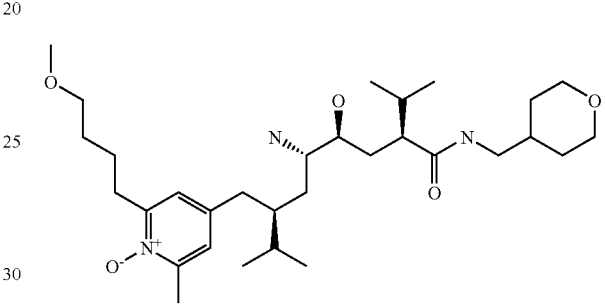

5-Amino-4-hydroxy-2-isopropyl-7-[2-(4-methoxybutyl-6-methyl-1-oxypyridin-4-ylmethyl]-8-methyl-N-(tetrahydropyran-4-ylmethyl)nonanamide The title compound is identified by means of the Rf in analogy to method E from 0.5 mmol of tert-butyl {2-hydroxy-1-{2-[2-(4-methoxybutyl)-6-methyl-1-oxypyridin-4-ylmethyl]-3-methyl-butyl}-5-methyl-4-[(tetrahydropyran-4-ylmethyl)carbamoyl]hexyl}carbamate.

The starting materials are prepared as follows:

a) tert-Butyl {2-hydroxy-1-{2-[2-(4-methoxybutyl)-6-methyl-1-oxypyridin-4-ylmethyl]-3-methylbutyl}-5-methyl-4-[(tetrahydropyran-4-ylmethyl)carbamoyl]hexyl}carbamate A solution of 1 mmol of tert-butyl {2-hydroxy-1-{2-[2-(4-methoxybutyl)-6-methylpyridin-4-ylmethyl]-3-methylbutyl}-5-methyl-4-[(tetrahydropyran-4-ylmethyl)carbamoyl]hexyl}carbamate in 30 ml of dichloromethane is mixed with 2 mmol of m-chloroperbenzoic acid and stirred at room temperature for 2 hours. It is poured into 1M NaOH and extracted with tert-butyl methyl ether (3×). The combined organic phases are washed with water and brine, dried with sodium sulphate and evaporated. The title compound is identified by means of the Rf from the residue by flash chromatography (SiO$_2$ 60 F).

b) tert-Butyl {2-hydroxy-1-{2-[2-(4-methoxybutyl)-6-methylpyridin-4-ylmethyl]-3-methylbutyl}-5-methyl-4-[(tetrahydropyran-4-ylmethyl)carbamoyl]hexyl}carbamate The title compound is identified by means of the Rf in analogy to method B from 0.6 mmol of tert-butyl {1-(4- isopropyl-5-oxotetrahydrofuran-2-yl)-3-[2-(4-methoxybutyl)-6-methylpyridin-4-ylmethy]-4-methylpentyl}carbamate and 60 mmol of tetrahydropyran-4-ylmethylamine (Example JJJ).

c) tert-Butyl {1-(4-isopropyl-5-oxotetrahydrofuran-2-yl)-3-[2-(4-methoxybutyl)-6-methylpyridin-4-ylmethyl]-4-methylpentyl}carbamate The title compound is identified by means of the Rf in analogy to method D from 2.5 mmol of 5-{1-amino-3-[2-(4-methoxybutyl)-6-methylpyridin-4-ylmethyl]-4-methylpentyl}-3-isopropyl-dihydrofuran-2-one.

d) 5-{1-Amino-3-[2-(4-methoxybutyl)-6-methylpyridin-4-ylmethyl]-4-methylpentyl}-3-isopropyldihydrofuran-2-one The title compound is identified by means of the Rf in analogy to method F from 3.1 mmol of 2-[2-azido-2-(4-isopropyl-5-oxotetrahydrofuran-2-yl)ethyl]-1-[2-(4-methoxybutyl)-6-methylpyridin-4-yl]-3-methylbutyl methoxy acetate.

e) 2-[2-Azido-2-(4-isopropyl-5-oxotetrahydrofuran-2-yl)ethyl]-1-[2-(4-methoxybutyl)-6-methylpyridin-4-yl]-3-methylbutyl methoxy acetate The title compound is identified by means of the Rf in analogy to method G from 3.5 mmol of 5-(1-azido-3-{hydroxy-[2-(4-methoxybutyl)-6-methylpyridin-4-yl]methyl}-4-methylpentyl)-3-isopropyldihydrofuran-2-one.

f) 5-(1-Azido-3-{hydroxy-[2-(4-methoxybutyl)-6-methylpyridin-4-yl]methyl}-4-methylpentyl)-3-isopropyldihydrofuran-2-one The title compound is identified by means of the Rf in analogy to method I from 26 mmol of 4-bromo-2-(4-methoxybutyl)-6-methylpyridine (building block 32).

The invention claimed is:
1. A compound of the formula

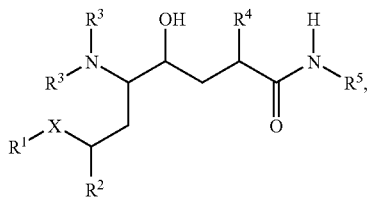

(I)

or its salt, or a compound of formula (I), in which one or more atoms are replaced by their stable, nonradioactive isotopes; wherein X is —$CH_2$—;

$R^1$ is a mono- to tetrasubstituted, mono- or bicyclic, unsaturated heterocyclic radical having 1 to 4 nitrogen atoms, where the substituents of the said radicals are selected independently of one another from the group consisting of acetamidinyl-$C_{1-6}$alkyl, 3-acetamidomethylpyrrolidinyl, acyl-$C_{1-6}$alkoxy-$C_{1-6}$alkyl, (N-acyl)-$C_{1-6}$alkoxy-$C_{1-6}$alkylamino, $C_{1-6}$alkanoyl, $C_{1-6}$alkanoyloxy, $C_{2-6}$alkenyl, $C_{2-6}$alkenyloxy, $C_{2-6}$alkenyloxy-$C_{1-6}$alkyl, $C_{1-6}$alkoxy, $C_{1-6}$alkoxy-$C_{1-6}$alkoxy, $C_{1-6}$alkoxy-$C_{1-6}$alkoxy-$C_{1-6}$alkyl, $C_{1-6}$alkoxy-$C_{1-6}$alkyl, (N—$C_{1-6}$alkoxy)-$C_{1-6}$alkylaminocarbonyl-$C_{1-6}$alkoxy, (N—$C_{1-6}$alkoxy)-$C_{1-6}$alkylaminocarbonyl-$C_{1-6}$alkyl, $C_{1-6}$alkoxy-$C_{1-6}$alkylcarbamoyl, $C_{1-6}$alkoxy-$C_{1-6}$alkylcarbonyl, $C_{1-6}$alkoxy-$C_{1-6}$alkylcarbonylamino, 1-$C_{1-6}$alkoxy-$C_{1-6}$alkylimidazol-2-yl, 2-$C_{1-6}$alkoxy-$C_{1-6}$alkyl-4-oxoimidazol-1-yl, 3-$C_{1-6}$alkoxy-$C_{1-6}$ alkylpyrrolidinyl, 1-$C_{1-6}$alkoxy-$C_{1-6}$alkyltetrazol-5-yl, 5-$C_{1-6}$alkoxy-$C_{1-6}$alkyltetrazol-1-yl, $C_{1-6}$alkoxyaminocarbonyl-$C_{1-6}$alkoxy, $C_{1-6}$alkoxyaminocarbonyl-$C_{1-6}$ alkyl, $C_{1-6}$alkoxycarbonyl, $C_{1-6}$alkoxycarbonyl-$C_{1-6}$ alkoxy, $C_{1-6}$alkoxycarbonyl-$C_{1-6}$alkyl, $C_{1-6}$alkoxycarbonylamino, $C_{1-6}$alkoxycarbonylamino-$C_{1-6}$alkoxy, $C_{1-6}$alkoxycarbonylamino-$C_{1-6}$alkyl, $C_{1-6}$alkyl, (N—$C_{1-6}$alkyl)-$C_{1-6}$alkoxy-$C_{1-6}$alkylcarbamoyl, (N—$C_{1-6}$alkyl)-$C_{1-6}$alkoxy-$C_{1-6}$alkylcarbonylamino, (N—$C_{1-6}$alkyl)-$C_{1-6}$alkoxycarbonylamino, (N—$C_{1-6}$alkyl)-$C_{0-6}$alkylcarbonylamino-$C_{1-6}$alkoxy, (N—$C_{1-6}$alkyl)-$C_{0-6}$alkylcarbonylamino-$C_{1-6}$alkyl, (N—$C_{1-6}$alkyl)-$C_{1-6}$alkylsulphonylamino-$C_{1-6}$alkoxy, (N—$C_{1-6}$alkyl)-$C_{1-6}$alkylsulphonylamino-$C_{1-6}$alkyl, $C_{1-6}$alkylamidinyl, $C_{1-6}$alkylamino, di-$C_{1-6}$alkylamino, $C_{1-6}$alkylamino-$C_{2-6}$alkoxy, di-$C_{1-6}$alkylamino-$C_{2-6}$ alkoxy, $C_{1-6}$alkylamino-$C_{1-6}$alkyl, $C_{1-6}$alkylaminocarbonyl, $C_{1-6}$alkylaminocarbonyl-$C_{1-6}$alkoxy, di-$C_{1-6}$ alkylaminocarbonyl-$C_{1-6}$alkoxy, $C_{1-6}$alkylaminocarbonyl-$C_{1-6}$ alkoxy-$C_{1-6}$alkyl, $C_{1-6}$alkylaminocarbonyl-$C_{1-6}$ alkyl, $C_{1-6}$alkylaminocarbonylamino-$C_{1-6}$alkoxy, $C_{1-6}$alkylaminocarbonylamino-$C_{1-6}$alkyl, di-$C_{1-6}$alkylaminocarbonyl-$C_{1-6}$ alkyl, di-$C_{1-6}$alkylamino-$C_{1-6}$ alkyl, $C_{1-6}$alkylcarbamoyl, di-$C_{1-6}$alkylcarbamoyl, $C_{0-6}$alkylcarbonylamino, $C_{0-6}$alkylcarbonylamino-$C_{1-6}$ alkoxy, $C_{0-6}$alkylcarbonylamino-$C_{1-6}$alkyl, $C_{1-6}$alkylcarbonyloxy-$C_{1-6}$alkoxy, $C_{1-6}$alkylcarbonyloxy-$C_{1-6}$ alkyl, $C_{1-6}$alkylenedioxy, $C_{1-6}$alkylsulphonyl, $C_{1-6}$alkylsulphonyl-$C_{1-6}$alkoxy, $C_{1-6}$alkylsulphonyl-$C_{1-6}$alkyl, $C_{1-6}$alkylsulphonylamino-$C_{1-6}$alkoxy, $C_{1-6}$alkylsulphonylamino-$C_{1-6}$alkyl, amino, amino-$C_{2-7}$alkoxy, amino-$C_{1-6}$alkyl, aryl-$C_{1-6}$alkanoyl, benzoyloxy-$C_{2-6}$ alkoxy, carbamoyl, carbamoyl-$C_{1-6}$alkoxy, carbamoyl-$C_{1-6}$ alkyl, carboxy, carboxy-$C_{1-6}$alkoxy, carboxy-$C_{1-6}$ alkoxy-$C_{1-6}$alkyl, carboxy-$C_{1-6}$alkyl, cyano, cyano-$C_{1-6}$ alkoxy, cyano-$C_{1-6}$alkyl, $C_{3-8}$cycloalkyl-$C_{1-6}$alkanoyl, $C_{3-8}$cycloalkyl-$C_{0-6}$alkoxy, $C_{3-8}$cycloalkyl-$C_{0-6}$alkyl, $C_{3-8}$cycloalkylcarbonylamino, $C_{3-8}$cycloalkylcarbonylamino-$C_{1-6}$alkoxy, $C_{3-8}$cycloalkylcarbonylamino-$C_{1-6}$ alkyl, 3,4-dihydroxypyrrolidinyl, O,N-dimethylhydroxylamino-$C_{1-6}$alkyl, 2,6-dimethylmorpholinyl, 3,5-dimethylmorpholinyl, dioxanyl, dioxolanyl, dioxolanyl-$C_{1-6}$alkoxy, 4,4-dioxothiomorpholinyl, dithianyl, dithiolanyl, optionally $C_{1-6}$alkoxy-, $C_{1-6}$alkyl-, dihydroxy-$C_{1-6}$alkylaminocarbonyl- or halogen-substituted furyl, furyl-$C_{1-6}$alkoxy, furyl-$C_{1-6}$ alkyl, pyridyl, pyridyl-$C_{1-6}$alkoxy, pyridyl-$C_{1-6}$alkyl, pyridylamino, pyridyloxy, pyridylthio, pyrimidinyl, pyrimidinyl-$C_{1-6}$ alkoxy, pyrimidinyl-$C_{1-6}$alkyl, pyrimidinylamino, pyrimidinyloxy, pyrimidinylthio, thienyl, thienyl-$C_{1-6}$ alkoxy or thienyl-$C_{1-6}$alkyl, halogen, heterocyclyl-$C_{1-6}$ alkanoyl, hydroxy, hydroxy-$C_{2-6}$alkoxy, hydroxy-$C_{2-6}$ alkoxy-$C_{1-6}$alkoxy, hydroxy-$C_{2-6}$alkoxy-$C_{1-6}$alkyl, hydroxy-$C_{1-6}$alkyl, (N-hydroxy)-$C_{1-6}$alkylaminocarbonyl-$C_{1-6}$alkoxy, (N-hydroxy)-$C_{1-6}$alkylaminocarbonyl-$C_{1-6}$alkyl, (N-hydroxy)aminocarbonyl-$C_{1-6}$alkoxy, (N-hydroxy)aminocarbonyl-$C_{1-6}$alkyl, hydroxybenzyloxy, 2-hydroxymethylpyrrolidinyl, 4-hydroxypiperidinyl, 3-hydroxypyrrolidinyl, imidazolyl-$C_{1-6}$alkoxy, imidazolyl-$C_{1-6}$alkyl, methoxybenzyloxy, methylenedioxybenzyloxy, 2-methylimidazolyl-$C_{1-6}$alkoxy, 2-methylimidazolyl-$C_{1-6}$alkyl, 3-methyl-[1,2,4]-oxadiazol-5-yl-$C_{1-6}$alkoxy, 5-methyl-[1,2,4]-oxadiazol-3-yl-$C_{1-6}$ alkoxy, 3-methyl-[1,2,4]-oxadiazol-5-yl-$C_{1-6}$ alkyl, 5-methyl-[1,2,4]-oxadiazol-3-yl-$C_{1-6}$alkyl, O-methyloximyl-$C_{1-6}$alkyl, 4-methylpiperazinyl, N-methylpiperazino-$C_{1-6}$alkoxy, N-methylpiperazino-$C_{1-6}$alkoxy-$C_{1-6}$alkyl, N-methylpiperazino-$C_{1-6}$alkyl, 5-methyltetrazol-1-yl-$C_{1-6}$alkoxy, 5-methyltetrazol-1-yl-$C_{1-6}$alkyl, morpholinyl, morpholino-$C_{1-6}$alkoxy, morpholino-$C_{1-6}$alkoxy-$C_{1-6}$alkyl, morpholino-$C_{1-6}$alkyl, nitro, [1,2,4]-oxadiazol-5-yl-$C_{1-6}$alkoxy, [1,2,4]-oxadiazol-5-yl-$C_{1-6}$alkyl, oxazol-4-yl-$C_{1-6}$alkoxy, oxazol-4-yl-$C_{1-6}$alkyl, oxide, oxo, 2-oxoimidazolidinyl, 2-oxo-[1,3]oxazinyl, 2-oxooxazolidinyl, 2-oxooxazolidinyl-$C_{1-6}$alkoxy, 2-oxooxazolidinyl-$C_{1-6}$alkyl, 4-oxopiperidinyl, 2-oxopyrrolidinyl, 2-oxopyrrolidinyl-$C_{1-6}$alkoxy, 2-oxopyrrolidinyl-$C_{1-6}$alkyl, 2-oxotetrahydropyrimidinyl, 4-oxothiomorpholinyl, optionally $C_{1-6}$alkoxy-, $C_{1-6}$alkoxycarbonyl-, $C_{1-6}$alkyl-, $C_{1-6}$alkylamino-, di-$C_{16}$alkylamino-, halogen-, hydroxyl-, hydroxy-$C_{1-6}$alkyl- or trifluoromethyl-substituted phenoxy, phenyl, phenyl-$C_{1-6}$alkoxy, phenyl-$C_{1-6}$alkyl or phenylthio, piperazinyl, piperazino-$C_{1-6}$ alkoxy, piperazino-$C_{1-6}$alkoxy-$C_{1-6}$alkyl, piperazino-$C_{1-6}$alkyl, piperidinyl, piperidino-$C_{1-6}$alkoxy, piperidino-$C_{1-6}$alkoxy-$C_{1-6}$alkyl, polyhalogen-$C_{1-6}$ alkoxy, polyhalogen-$C_{1-6}$ alkyl, pyridylcarbamoyloxy-$C_{1-6}$alkoxy, pyridylcarbonylamino-$C_{1-6}$alkoxy, pyrrolidinyl, pyrrolyl, tetrazol-1-yl-$C_{1-6}$alkoxy, tetrazol-2-yl-$C_{1-6}$ alkoxy, tetrazol-5-yl-$C_{1-6}$alkoxy, tetrazol-1-yl-$C_{1-6}$ alkyl, tetrazol-2-yl-$C_{1-6}$alkyl, tetrazol-5-yl-$C_{1-6}$alkyl, thiazol-4-yl-$C_{1-6}$alkoxy, thiazol-4-yl-$C_{1-6}$alkyl, thiomorpholinyl, [1,2,4]-triazol-1-yl-$C_{1-6}$alkoxy, [1,2,4]-triazol-4-yl-$C_{1-6}$alkoxy, [1,2,4]-triazol-1-yl-$C_{1-6}$alkyl, [1,2,4]-triazol-4-yl-$C_{1-6}$alkyl and the radical —O—$CH_2CH(OH)CH_2NRx$, where NRx is a mono- or di-$C_{1-6}$alkylamino, N-methylpiperazino, morpholino, piperazino or piperidino radical, and where in the case where $R^1$ is a bicyclic heterocyclic ring system, at least the ring not directly bonded to X is substituted as indicated;

$R^2$ is $C_{1-6}$alkyl or $C_{3-6}$cycloalkyl;

$R^3$ is independently of one another H, $C_{1-6}$alkyl, $C_{1-6}$alkoxycarbonyl or $C_{1-6}$alkanoyl;

$R^4$ is $C_{2-6}$alkenyl, $C_{1-6}$alkyl, unsubstituted or substituted aryl-$C_{1-6}$alkyl or $C_{3-8}$cycloalkyl;

$R^5$ is -$L_m$-$R^6$;

L is $C_{1-6}$alkylene which is unsubstituted or substituted by 1-4 halogen, or a linker:

n=0, 1 or 2;

m=0 or 1;

$R^6$ is a radical composed of 2 cyclic systems selected from bicyclo[x.y.z]alkyl, spiro[o.p]alkyl, mono- or bioxabicyclo[x.y.z]alkyl or mono- or bioxaspiro[o.p]alkyl, all of which may be substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino, or if m=1: is also saturated $C_{3-8}$heterocyclyl which comprises 1-2 oxygen atoms, unsubstituted or substituted by 1-3 substituents selected from $C_{1-6}$alkyl, $C_{1-6}$alkoxy, cyano, halogen, $C_{1-6}$-alkoxy-$C_{1-6}$alkyl, hydroxy-$C_{1-6}$alkyl or dialkylamino;

o=2, 3, 4, 5 or 6 p=2, 3, 4, 5 or 6 x=1, 2, 3, 4 or 5;

y=1, 2, 3, 4 or 5; and z=0, 1, 2, 3, 4 or 5; where x≧y≧z.

2. A pharmaceutically acceptable salt of a compound according to claim 1.

3. A compound according to claim 1 of the formula (IA)

or its salt or a compound of formula (IA), in which one or more atoms are replaced by their stable, nonradioactive isotopes; wherein $R^1$, $R^2$, $R^3$, $R^4$, $R^5$ and X have the meaning indicated for the compounds of the formula (I) in claim 1.

4. A pharmaceutically acceptable salt of a compound according to claim 3.

5. A compound according to claim 1, wherein $R^2$ is $C_{1-6}$alkyl, and $R^4$ is $C_{1-6}$alkyl.

6. A compound according to claim 3, wherein $R^2$ is $C_{1-6}$alkyl, and $R^4$ is $C_{1-6}$alkyl.

7. A compound according to claim 1, wherein $R^3$ is H, and $R^6$ is a radical composed of 2 cyclic systems and selected from bicyclo[x.y.z]alkyl, spiro[o.p]alkyl, mono- or bioxabicyclo[x.y.z]alkyl or mono- or bioxaspiro[o.p]alkyl, all of which may be substituted by 1-3 substituents selected from $C_{1-6}$alkyl, $C_{1-6}$alkoxy, cyano, halogen, $C_{1-6}$alkoxy-$C_{1-6}$alkyl, hydroxy-$C_{1-6}$alkyl or dialkylamino.

8. A compound according to claim 1, wherein $R^1$ is a radical selected from the group comprising benzoimidazolyl, quinazolinyl, quinolyl, quinoxalinyl, imidazolyl, imidazo[1,5-a]pyridinyl, imidazo[1,2-a]pyrimidinyl, indazolyl, indolyl, isoquinolyl, pyrimidinyl, pyridinyl, pyrrolo[2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a]pyridinyl and [1,2,4]triazolo[4,3-a]pyridinyl, which are substituted by one to four radicals independently of one another selected from acetamidinyl-$C_{1-6}$alkyl, 3-acetamidomethylpyrrolidinyl, acyl-$C_{1-6}$ alkoxy-$C_{1-6}$alkyl, (N-acyl)-$C_{1-6}$alkoxy-$C_{1-6}$alkylamino, $C_{1-6}$alkanoyl, $C_{1-6}$alkanoyloxy, $C_{2-6}$alkenyl, $C_{2-6}$alkenyloxy, $C_{2-6}$alkenyloxy-$C_{1-6}$alkyl, $C_{1-6}$alkoxy, $C_{1-6}$alkoxy-$C_{1-6}$ alkoxy, $C_{1-6}$alkoxy-$C_{1-6}$alkoxy-$C_{1-6}$alkyl, $C_{1-6}$alkoxy-$C_{1-6}$ alkyl, (N—$C_{1-6}$alkoxy)-$C_{1-6}$alkylaminocarbonyl-$C_{1-6}$ alkoxy, (N—$C_{1-6}$alkoxy)-$C_{1-6}$alkylaminocarbonyl-$C_{1-6}$ alkyl, $C_{1-6}$alkoxy-$C_{1-6}$alkylcarbamoyl, $C_{1-6}$alkoxy-$C_{1-6}$ alkylcarbonyl, $C_{1-6}$alkoxy-$C_{1-6}$alkylcarbonylamino, 1-$C_{1-6}$ alkoxy-$C_{1-6}$alkylimidazol-2-yl, 2-$C_{1-6}$alkoxy-$C_{1-6}$alkyl-4-oxoimidazol-1-yl, 3-$C_{1-6}$alkoxy-$C_{1-6}$alkylpyrrolidinyl, 1-$C_{1-6}$ alkoxy-$C_{1-6}$alkyltetrazol-5-yl, 5-$C_{1-6}$alkoxy-$C_{1-6}$alkyltetrazol-1-yl, $C_{1-6}$alkoxyaminocarbonyl-$C_{1-6}$alkoxy, $C_{1-6}$alkoxyaminocarbonyl-$C_{1-6}$alkyl, $C_{1-6}$alkoxycarbonyl, $C_{1-6}$alkoxycarbonyl-$C_{1-6}$alkoxy, $C_{1-6}$alkoxycarbonyl-$C_{1-6}$alkyl, $C_{1-6}$alkoxycarbonylamino, $C_{1-6}$alkoxycarbonylamino-$C_{1-6}$alkoxy, $C_{1-6}$alkoxycarbonylamino-$C_{1-6}$alkyl, $C_{1-6}$alkyl, (N—$C_{1-6}$alkyl)-$C_{1-6}$alkoxy-$C_{1-6}$alkylcarbamoyl, (N—$C_{1-6}$alkyl)-$C_{1-6}$alkoxy-$C_{1-6}$alkylcarbonylamino, (N—$C_{1-6}$alkyl)-$C_{1-6}$alkoxycarbonylamino, (N—$C_{1-6}$alkyl)-$C_{0-6}$alkylcarbonylamino-$C_{1-6}$alkoxy, (N—$C_{1-6}$alkyl)-$C_{0-6}$ alkylcarbonylamino-$C_{1-6}$alkyl, (N—$C_{1-6}$alkyl)-$C_{1-6}$alkylsulphonylamino-$C_{1-6}$alkoxy, (N—$C_{1-6}$alkyl)-$C_{1-6}$alkylsulphonylamino-$C_{1-6}$alkyl, $C_{1-6}$alkylamidinyl, $C_{1-6}$alkylamino, di-$C_{1-6}$alkylamino, $C_{1-6}$alkylamino-$C_{2-6}$alkoxy, di-$C_{1-6}$alkylamino-$C_{2-6}$alkoxy, $C_{1-6}$alkylamino-$C_{1-6}$alkyl, $C_{1-6}$alkylaminocarbonyl, $C_{1-6}$alkylaminocarbonyl-$C_{1-6}$ alkoxy, di-$C_{1-6}$ alkylaminocarbonyl-$C_{1-6}$alkoxy, $C_{1-6}$alkylaminocarbonyl-$C_{1-6}$alkoxy-$C_{1-6}$alkyl, $C_{1-6}$alkylaminocarbonyl-$C_{1-6}$alkyl, $C_{1-6}$alkylaminocarbonylamino-$C_{1-6}$alkoxy, $C_{1-6}$alkylaminocarbonylamino-$C_{1-6}$alkyl, di-$C_{1-6}$ alkylaminocarbonyl-$C_{1-6}$ alkyl, di-$C_{1-6}$alkylamino-$C_{1-6}$ alkyl, $C_{1-6}$alkylcarbamoyl, di-$C_{1-6}$alkylcarbamoyl, $C_{0-6}$alkylcarbonylamino, $C_{0-6}$alkylcarbonylamino-$C_{1-6}$alkoxy, $C_{0-6}$alkylcarbonylamino-$C_{1-6}$ alkyl, $C_{1-6}$alkylcarbonyloxy-$C_{1-6}$ alkoxy, $C_{1-6}$alkylcarbonyloxy-$C_{1-6}$alkyl, $C_{1-6}$alkylenedioxy, $C_{1-6}$alkylsulphonyl, $C_{1-6}$alkylsulphonyl-$C_{1-6}$alkoxy, $C_{1-6}$alkylsulphonyl-$C_{1-6}$ alkyl, $C_{1-6}$alkylsulphonylamino-$C_{1-6}$alkoxy, $C_{1-6}$alkylsulphonylamino-$C_{1-6}$alkyl, amino, amino-$C_{2-7}$alkoxy, amino-$C_{1-6}$alkyl, aryl-$C_{1-6}$alkanoyl, benzoyloxy-$C_{2-6}$alkoxy, carbamoyl, carbamoyl-$C_{1-6}$ alkoxy, carbamoyl-$C_{1-6}$alkyl, carboxy, carboxy-$C_{1-6}$alkoxy, carboxy-$C_{1-6}$alkoxy-$C_{1-6}$ alkyl, carboxy-$C_{1-6}$alkyl, cyano, cyano-$C_{1-6}$alkoxy, cyano-$C_{1-6}$alkyl, $C_{3-8}$cycloalkyl-$C_{1-6}$alkanoyl, $C_{3-8}$cycloalkyl-$C_{0-6}$ alkoxy, $C_{3-8}$cycloalkyl-$C_{0-6}$ alkyl, $C_{3-8}$cycloalkylcarbonylamino, $C_{3-8}$cycloalkylcarbonylamino-$C_{1-6}$alkoxy, $C_{3-8}$cycloalkylcarbonylamino-$C_{1-6}$ alkyl, 3,4-dihydroxypyrrolidinyl, O,N-dimethylhydroxylamino-$C_{1-6}$alkyl, 2,6-dimethylmorpholinyl, 3,5-dimethylmorpholinyl, dioxanyl, dioxolanyl, dioxolanyl-$C_{1-6}$alkoxy, 4,4-dioxothiomorpholinyl, dithianyl, dithiolanyl, optionally $C_{1-6}$alkoxy-, $C_{1-6}$alkyl-, dihydroxy-$C_{1-6}$alkylaminocarbonyl- or halogen-substituted furyl, furyl-$C_{1-6}$alkoxy, furyl-$C_{1-6}$ alkyl, pyridyl, pyridyl-$C_{1-6}$ alkoxy, pyridyl-$C_{1-6}$alkyl, pyridylamino, pyridyloxy, pyridylthio, pyrimidinyl, pyrimidinyl-$C_{1-6}$alkoxy, pyrimidinyl-$C_{1-6}$alkyl, pyrimidinylamino, pyrimidinyloxy, pyrimidinylthio, thienyl, thienyl-$C_{1-6}$alkoxy or thienyl-$C_{1-6}$alkyl, halogen, heterocyclyl-$C_{1-6}$alkanoyl, hydroxy, hydroxy-$C_{2-6}$ alkoxy, hydroxy-$C_{2-6}$alkoxy-$C_{1-6}$ alkoxy, hydroxy-$C_{2-6}$ alkoxy-$C_{1-6}$alkyl, hydroxy-$C_{1-6}$alkyl, (N-hydroxy)-$C_{1-6}$ alkylaminocarbonyl-$C_{1-6}$alkoxy, (N-hydroxy)-$C_{1-6}$ alkylaminocarbonyl-$C_{1-6}$alkyl, (N-hydroxy)aminocarbonyl-$C_{1-6}$alkoxy, (N-hydroxy)aminocarbonyl-$C_{1-6}$ alkyl, hydroxylbenzyloxy, 2-hydroxymethylpyrrolidinyl, 4-hydroxypiperidinyl, 3-hydroxypyrrolidinyl, imidazolyl-$C_{1-6}$alkoxy, imidazolyl-$C_{1-6}$alkyl, methoxybenzyloxy, methylenedioxybenzyloxy, 2-methylimidazolyl-$C_{1-6}$alkoxy, 2-methylimidazolyl-$C_{1-6}$alkyl, 3-methyl-[1,2,4]-oxadiazol-5-yl-$C_{1-6}$alkoxy, 5-methyl-[1,2,4]-oxadiazol-3-yl-$C_{1-6}$ alkoxy, 3-methyl-[1,2,4]-oxadiazol-5-yl-$C_{1-6}$alkyl, 5-methyl-[1,2,4]-oxadiazol-3-yl-$C_{1-6}$alkyl, O-methyloximyl-$C_{1-6}$ alkyl, 4-methylpiperazinyl, N-methylpiperazino-$C_{1-6}$ alkoxy, N-methylpiperazino-$C_{1-6}$ alkoxy-$C_{1-6}$alkyl, N-methylpiperazino-$C_{1-6}$alkyl, 5-methyltetrazol-1-yl-$C_{1-6}$ alkoxy, 5-methyltetrazol-1-yl-$C_{1-6}$alkyl, morpholinyl, morpholino-$C_{1-6}$alkoxy, morpholino-$C_{1-6}$ alkoxy-$C_{1-6}$alkyl, morpholino-$C_{1-6}$alkyl, nitro, [1,2,4]-oxadiazol-5-yl-$C_{1-6}$alkoxy, [1,2,4]-oxadiazol-5-yl-$C_{1-6}$alkyl, oxazol-4-yl-$C_{1-6}$alkoxy, oxazol-4-yl-$C_{1-6}$alkyl, oxide, oxo, 2-oxoimidazolidinyl, 2-oxo-[1,3]oxazinyl, 2-oxooxazolidinyl, 2-oxooxazolidinyl-$C_{1-6}$alkoxy, 2-oxooxazolidinyl-$C_{1-6}$ alkyl, 4-oxopiperidinyl, 2-oxopyrrolidinyl, 2-oxopyrrolidinyl-$C_{1-6}$alkoxy, 2-oxopyrrolidinyl-$C_{1-6}$alkyl, 2-oxotetrahydropyrimidinyl, 4-oxothiomorpholinyl, optionally $C_{1-6}$alkoxy-, $C_{1-6}$alkoxycarbonyl-, $C_{1-6}$alkyl-, $C_{1-6}$alkylamino-, di-$C_{1-6}$alkylamino-, halogen-, hydroxyl-, hydroxy-$C_{1-6}$alkyl- or trifluoromethyl-substituted phenoxy, phenyl, phenyl-$C_{1-6}$alkoxy, phenyl-$C_{1-6}$alkyl or phenylthio, piperazinyl, piperazino-$C_{1-6}$alkoxy, piperazino-$C_{1-6}$alkoxy-$C_{1-6}$ alkyl, piperazino-$C_{1-6}$alkyl, piperidinyl, piperidino-$C_{1-6}$ alkoxy, piperidino-$C_{1-6}$alkoxy-$C_{1-6}$alkyl, polyhalogen-$C_{1-6}$ alkoxy, polyhalogen-$C_{1-6}$alkyl, pyridylcarbamoyloxy-$C_{1-6}$ alkoxy, pyridylcarbonylamino-$C_{1-6}$alkyl, pyrrolidinyl, pyrrolyl, tetrazol-1-yl-$C_{1-6}$alkoxy, tetrazol-2-yl-$C_{1-6}$alkoxy, tetrazol-5-yl-$C_{1-6}$alkoxy, tetrazol-1-yl-$C_{1-6}$alkyl, tetrazol-2-yl-$C_{1-6}$alkyl, tetrazol-5-yl-$C_{1-6}$alkyl, thiazol-4-yl-$C_{1-6}$ alkoxy, thiazol-4-yl-$C_{1-6}$alkyl, thiomorpholinyl, [1,2,4]-triazol-1-yl-$C_{1-6}$alkoxy, [1,2,4]-triazol-4-yl-$C_{1-6}$alkoxy, [1,2,4]-triazol-1-yl-$C_{1-6}$alkyl, [1,2,4]-triazol-4-yl-$C_{1-6}$alkyl and the radical —O—$CH_2CH(OH)CH_2NRx$, where NRx is a mono- or di-$C_{1-6}$alkylamino, N-methylpiperazino, morpholino, piperazino or piperidino radical, and where in the case where $R^1$ is a bicyclic heterocyclic ring system, at least the ring not bonded to X is substituted as indicated.

9. A compound according to claim 1, wherein $R^1$ is a radical selected from the group comprising benzoimidazolyl, imidazo[1,2-a]pyrimidinyl, imidazo[1,2-a]pyridinyl, imidazo[1,5-a]pyridinyl, indazolyl, indolyl, pyridinyl, pyrrolo [2,3-b]pyridinyl, pyrrolo[3,2-c]pyridinyl, pyrrolo[2,3-c]pyridinyl, pyrrolo[3,2-b]pyridinyl, [1,2,3]triazolo[1,5-a] pyridinyl and [1,2,4]triazolo[4,3-a]pyridinyl, where the said radicals are substituted by one to four radicals independently of one another selected from $C_{1-6}$alkanoyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino-$C_{1-6}$alkoxy, $C_{1-6}$alkoxycarbonylamino-$C_{1-6}$ alkyl, $C_{1-6}$alkyl, $C_{0-6}$alkylcarbonylamino-$C_{1-6}$alkoxy, $C_{0-6}$alkylcarbonylamino-$C_{1-6}$alkyl, carbamoyl, carboxyl, cyano, halogen, hydroxy, hydroxy-$C_{2-6}$alkoxy, hydroxy-$C_{1-6}$ alkyl, oxide, polyhalo-$C_{1-6}$alkoxy, polyhalo-$C_{1-6}$alkyl and trifluoromethyl, where in the case where $R^1$ is a bicyclic heterocyclic ring system, at least the ring not bonded to X is substituted as indicated.

10. A pharmaceutical composition, comprising a compound of the formula (I) or a compound in which one or more atoms are replaced by their stable, nonradioactive isotopes, or its pharmaceutically acceptable salt, according to claim 1, and a pharmaceutically inert excipient.

11. A pharmaceutical combination in the form of a product or of a kit composed of individual components consisting a) of a compound of the formula (I) or a compound of formula (I), in which one or more atoms are replaced by their stable, nonradioactive isotopes, or its pharmaceutically acceptable salt, according to claim 1, and b) at least one pharmaceutical active ingredient that has a cardiovascular activity.

* * * * *